United States Patent [19]
Brown et al.

[11] Patent Number: 5,919,793
[45] Date of Patent: *Jul. 6, 1999

[54] HETEROCYCLIC DERIVATIVES

[75] Inventors: George Robert Brown, Wilmslow; Paul Robert Owen Whittamore, Macclesfield; David Robert Brittain, Bamford, all of United Kingdom

[73] Assignee: Zeneca Limited, London, United Kingdom

[*] Notice: This patent is subject to a terminal disclaimer.

[21] Appl. No.: 08/537,827

[22] PCT Filed: Apr. 28, 1994

[86] PCT No.: PCT/GB94/00910

§ 371 Date: Oct. 26, 1995

§ 102(e) Date: Oct. 26, 1995

[87] PCT Pub. No.: WO94/25459

PCT Pub. Date: Nov. 10, 1994

[30] Foreign Application Priority Data

Apr. 29, 1993 [GB] United Kingdom ............... 9308842
Dec. 3, 1993 [GB] United Kingdom ............... 9324813
Feb. 4, 1994 [GB] United Kingdom ............... 9402127

[51] Int. Cl.$^6$ ..................... A61K 31/435; C07D 435/02
[52] U.S. Cl. ......................... 514/305; 546/133; 546/137
[58] Field of Search ................... 546/133, 137; 514/305

[56] References Cited

U.S. PATENT DOCUMENTS

| | | | |
|---|---|---|---|
| 5,104,867 | 4/1992 | Kawamoto | 514/210 |
| 5,385,912 | 1/1995 | Neuenschwander | 514/305 |
| 5,691,349 | 11/1997 | Mallion | 514/305 |

FOREIGN PATENT DOCUMENTS

| | | |
|---|---|---|
| 458 214 | 11/1991 | European Pat. Off. |
| 92 15579 | 9/1992 | WIPO |
| 93 13096 | 7/1993 | WIPO |
| 93 15073 | 8/1993 | WIPO |
| 93 21184 | 10/1993 | WIPO |
| 94 03451 | 2/1994 | WIPO |
| 94 05660 | 3/1994 | WIPO |

OTHER PUBLICATIONS

Delgado, JN and Remers, WA. Textbook of Organic Medicinal and Pharmaceutical Chemistry. Ninth Edition. JB Lippincott Company. Philadelphia. Pp. 30–31, 1991.

Primary Examiner—Evelyn Huang
Attorney, Agent, or Firm—Cushman Darby & Cushman Intellectual Property Group of Pillsbury Madison & Sutro, LLP

[57] ABSTRACT

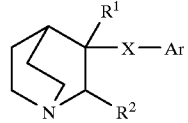

Compounds of formula (I) wherein $R^1$ is hydrogen or hydroxy; $R^2$ is hydrogen; or $R^1$ and $R^2$ are joined together so that $CR^1 14 CR^2$ is a double bond; X is selected from $-CH_2CH_2-$, $-C=CH-$, $-C\equiv C-$, $-CH_2O-$, $-OCH_2$, $CH_2NH-$, $-NHCH_2-$, $-CH_2CO-$, $-COCH_2-$, $-CH_2S(O)_n-$ and $-S(O)_nCH_2-$ (wherein n is 0, 1 or 2); Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C) alkylcarbamoyl, di-[(1-6C)alkyl]carbamoyl, (1-6C)alkenyl and oxime derivatives thereof and O—(1-6C)alkyl ethers of said oximes (1-6C)alkylthio, (1-6C)alkylsulphinyl and (1-6C)alkylsulphonyl when substituted by one or more groups selected from (1-6C)alkoxycarbonyl, (1-6C)alkanoyl and oxime derivatives thereof and O-(1-6C)alkyl ethers of said oxime derivatives, (1-6C)alkanoylamimo, (1-6C)alkanoyloxy, (1-6C)alkanoyloxy(1-6)alkyl, carbamoyl, N-(1-6C)alkylcarbamoyl, N,N-di[(1-6C)alkyl]carbamoyl, amino, (1-6C)alkylamino, di-[(1-6C)alkyl]amino, (1-6C)alkoxy, (2-6C)alkenyloxy, (1-6C)alkylthio, (1-6C)alkylsulphinyl, (1-6C)alkylsulphonyl, halogeno(1-6C)alkyl (2-6C)alkenyl, (2-6C)alkynyl, phenyl, phenoxy, cyano, nitro, hydroxy and carboxy; and wherein Ar may bear further substituents; and their pharmaceutically acceptable salts inhibit squalene synthese and are hence useful in lowering cholesterol levels in blood plasma Processes for preparing compounds of formula (I) are also referred to as well as pharmaceutical compositions containing them and their use in medicine.

20 Claims, No Drawings

HETEROCYCLIC DERIVATIVES

This application is the national phase of international application PCT/GB94/00910, filed Apr. 28, 1994, published as WO 94/25459 on Nov. 10, 1994.

This invention concerns heterocyclic derivatives which are useful in inhibiting squalene synthase, processes for their preparation and pharmaceutical compositions containing them. The present invention is also concerned with methods of using such heterocyclic derivatives in treating diseases and medical conditions where inhibition of squalene synthase is desirable, for example in treating diseases or medical conditions such as hypercholesterolemia and atherosclerosis.

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol, which results in an upregulation of the heptatic LDL receptor and thus in a lowering of circulating blood cholesterol levels.

Squalene synthase (also referred to in the art as squalene synthetase) is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovacsular disease. Thus, an agent which inhibits squalene synthase should be useful in treating diseases and medical conditions in which a reduction in the levels of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

The present invention is based on the discovery that certain heterocyclic derivatives are inhibitors of squalene synthase, and are hence useful in treating diseases and medical conditions in which inhibition of squalene synthase is desirable.

According to the present invention there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkanoyl and oxime derivatives thereof and O-(1-6C)alkyl ethers of said oximes, (1-6C)alkylthio, (1-6C)alkylsulphinyl and (1-6C)alkylsulphonyl when substituted by one or more groups selected from (1-6C)alkoxycarbonyl, (1-6C)alkanoyl and oxime derivatives thereof and O-(1-6C)alkyl ethers of said oxime derivatives, (1-6C)alkanoylamino, (1-6C)alkanoyloxy, (1-6C)alkanoyloxy(1-6C)alkyl, carbamoyl, N-(1-6C)alkylcarbamoyl, N,N-di[(1-6C)alkylcarbamoyl, amino, (1-6C)alkylamino, di-[(1-6C)alkyl]amino, (1-6C)alkoxy, (2-6C)alkenyloxy, (1-6C)alkylthio, (1-6C)alkylsulphinyl, (1-6C)alkylsulphonyl, halogeno(1-6C)alkyl, (2-6C)alkenyl, (2-6C)alkynyl, phenyl, phenoxy, cyano, nitro, hydroxy and carboxy; and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno(1-6C)alkyl, (1-6C)alkanoylamino, (1-4C)alkylenedioxy, (1-6C)alkanoyl and oxime derivatives thereof and O-(1-6C)alkyl ethers of said oxime derivatives; provided that when X is —$OCH_2$—, —$NHCH_2$— or —$S(O)_nCH_2$— (wherein n is 0,1 or 2), then $R^1$ is not hydroxy; and provided that when a substituent on Ar includes a phenyl moiety, X is —$OCH_2$—, then $R^1$ and $R^2$ are not both hydrogen, or joined together so that $CR^1$–$CR^2$ is a double bond.

In particular, according to the present invention there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-

[(1-6C)alkyl]carbamoyl, (1-6C)alkanoyl and oxime derivatives thereof and O-(1-6C)alkyl ethers of said oximes, (1-6C)alkylthio, (1-6C)alkylsulphinyl and (1-6C)alkylsulphonyl when substituted by one or more groups selected from (1-6C)alkoxycarbonyl, phenoxycarbonyl, (1-6C)alkanoyl, and oxime derivatives thereof and O-(1-6C)alkyl ethers of said oxime derivatives, (1-6C)alkanoylamino, (1-6C)alkanoyloxy, (1-6C)alkanoyloxy(1-6C)alkyl, N-(1-6C)alkylcarbamoyl, N,N-di[(1-6C)alkylcarbamoyl, amino, (1-6C)alkylamino, di-[(1-6C)alkyl]amino, (1-6C)alkoxy, (2-6C)alkenyloxy, (1-6C)alkylthio, (1-6C)alkylsulphinyl, (1-6C)alkylsulphonyl, halogeno(1-6C)alkyl, (2-6C)alkenyl, (2-6C)alkynyl, (2-6C)alkenyl, (2-6C)alkynyl, phenyl, phenoxy, cyano, nitro, hydroxy and carboxy; and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno(1-6C)alkyl, (1-6C)alkanoylamino, (1-4C)alkylenedioxy, (1-6C)alkanoyl and oxime derivatives thereof and O-(1-6C)alkyl ethers of said oxime derivatives; provided that when X is —OCH$_2$—, —NHCH$_2$— or —S(O)$_n$CH$_2$— (wherein n is 0,1 or 2), then R$^1$ is not hydroxy; and provided that when a substituent on Ar includes a phenyl moiety, then R$^1$ is hydroxy.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It will also be understood that, insofar as certain of the compounds of the formula I may exist as geometric isomers the present invention includes any such isomer which possesses the beneficial pharmacological effect of inhibiting squalene synthase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will be appreciated that when R and R$^2$ are joined so that CR$^1$–CR$^2$ is a double bond, the heterocyclic ring in formula I will comprise the 2,3-dehydroquinuclidine moiety shown in formula Ia.

A particular value for a group which may be present on Ar is, for example,

| | |
|---|---|
| for alkyl; | (1–4C)alkyl, such as methyl, ethyl, propyl, isopropyl, butyl, isobutyl or sec-butyl; |
| for alkenyl; | (2–4C)alkenyl, such as allyl, prop-2-enyl, but-2-enyl or 2-methyl-2-propenyl; |
| for alkynyl; | (2–4C)alkynyl, such as prop-2-ynyl or but-2-ynyl; |
| for alkoxy; | (1–4C)alkoxy, such as methoxy, ethoxy, propoxy, isopropoxy or butoxy; |
| for alkylamino; | (1–4C)alkylamino, such as methylamino, ethylamino, propylamino or butylamino; |
| for di-alkylamino; | di-[(1–4C)alkylamino, such as dimethylamino, diethylamino, methylpropylamino or dipropylamino; |
| for alkylcarbamoyl; | N-methylcarbamoyl, N-ethylcarbamoyl or N-propylcarbamoyl; |
| for di-alkylcarbamoyl; | N,N-dimethylcarbamoyl or N,N-diethylcarbamoyl; |
| for alkoxycarbonyl; | methoxycarbonyl, ethoxycarbonyl or propoxycarbonyl; |
| for alkoxycarbonyl-alkyl | methoxycarbonylmethyl, methoxycarbonylethyl, ethoxycarbonylethyl or ethoxycarbonylmethyl; |
| for alkylthio; | methylthio, ethylthio, propylthio, isopropylthio or butylthio; |
| for alkylsulphinyl; | methylsulphinyl, ethylsulphinyl, propylsulphinyl, isopropylsulphinyl or butylsulphinyl; |
| for alkylsulphonyl; | methylsulphonyl, ethylsulphonyl, propylsulphonyl, isoproylsulphonyl or butylsulphonyl; |
| for halogeno; | fluoro, chloro, bromo or iodo; |
| for halogenoalkyl; | halogenoalkyl containing one, two or three halo groups selected from fluoro, chloro, bromo and iodo and an alkyl group selected from methyl, ethyl, propyl, iso-propyl, butyl, iso-butyl and sec-butyl, (in particular fluoromethyl, difluoromethyl or trifluoromethyl); |
| for alkanoyl; | formyl, acetyl, propionyl and butyryl; |
| for O-(1–6C)alkyl ethers of alkanoyl oximes | methyl, ethyl, propyl, isopropyl and butyl ethers of said oximes; |
| for alkenyloxy; | allyloxy and propenyloxy; and |
| for (1–4C)alkylenedioxy | methylenedioxy, ethylenedioxy and trimethylenedioxy |
| for alkanoylamino; | foramido, acetamido, propionamido, iso-propionamido, butyramido or iso-butyramido; |
| for alkoxyalkoxy; | methoxyethoxy, ethoxymethoxy, ethoxyethoxy and methoxymethoxy; |
| for alkanoyloxy; | acetyloxy and propionyloxy; and |
| for alkanoyloxyalkyl; | acetyloxyziethyl, acetyloxyethyl, propionyloxymethyl and propionyloxy ethyl |

In particular Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-[(1-6C)alkoxy(1-6C)alkyl](1-6C)alkoxy, phenoxy(1-6C)alkoxy, (1-6C)alkoxy(1-6C)alkoxycarbonyl, di-[(1-6C)alkoxy](1-6C)alkyl, (1-6C)alkylamino(1-6C)alkyl, di-[(1-6C)alkyl]amino(1-6C)alkyl, (1-6C)alkylcarbonylamino(1-6C)alkyl, (3-6C)cycloalkyl(1-6C)alkoxy, (2-6C)alkenyloxy(1-6C)alkyl, carbamoyl(1-6C)alkyl, N-(1-6C)alkylcarbamoyl(1-6C)alkyl, phenyl(1-6C)alkyl, N,N-di[(1-6C)alkyl]carbamoyl(1-6C)alkyl; (1-6C)alkoxycarbonyl(2-6C)alkenyl, (1-6C)alkoxycarbonyl(2-6C)alkynyl, cyano(1-6C)alkoxy, cyano(1-6C)alkoxy(1-6C)alkyl, nitro(1-6C)alkoxy, nitro(1-6C)alkoxy(1-6C)alkyl, (1-6C)alkoxycarbonyl(1-6C)alkylthio, (1-6C)alkoxycarbonyl(1-6C)alkoxycarbonyl(1-6C)alkyl, (1-6C)alkoxy(1-6C)alkoxycarbonyl(1-6C)alkyl, (1-6C)alkylthio (1-6C)alkoxy, (1-6C)alkoxy(1-6C)alkyl, (1-6C)alkoxycarbonyl(1-6C)alkylcarbamoyl, (1-6C)alkoxy(1-6C)alkylcarbamoyl, (1-6C)alkanoyloxy(1-6C)alkyl, cyano(1-6C)alkyl, carboxy(1-6C)alkyl, hydroxy(1-6C)alkyl (1-6C)alkylamino(1-6C)alkyl, di-[(1-6C)alkyl]amino(1-6C)alkyl, (1-6C)alkylamino(1-6C)alkoxycarbonyl(1-6C)alkyl, di-[(1-6C)alkyl]amino(1-6C)alkoxycarbonyl(1-6C)alkyl, (1-6C)

alkylcarbamoyl(1-6C)alkoxycarbonyl, di-[(1-6C)alkyl] carbamoyl(1-6C)alkoxycarbonyl, carbamoyl(1-6C) alkoxycarbonyl, (1-6C)alkoxycarbonyl(1-6C)alkoxy(1-6C) alkyl, di-[(1-6C)alkyl]amino(1-6C)alkoxycarbonyl, (1-6C) alkoxycarbonyl(1-6C)alkanoyl, (1-6C)alkoxy(1-6C)alkoxy (1-6C)alkanoyl, (1-6C)alkylthio(1-6C)alkyl, (2-6C)alkenyl (1-6C)alkoxy(1-6C)alkyl, (2-6C)alkynyl(1-6C)alkoxy(1-6C)alkyl, halogeno(1-6C)alkyl(1-6C)alkoxycarbonyl, phenoxycarbonyl, di-[(1-6C)alkoxycarbonyl]alkyl, (1-6c) alkoxycarbonyl(1-6C)alkanoyloxy(1-6C)alkyl, (1-6C) alkoxy(1-6c)alkanoyloxy(1-6C)alkyl, (1-6C)alkoxy(1-6C) alkoxycarbonyl(1-6C)alkyl, hydroxy(1-6C)alkoxy, di-hydroxy(1-6C)alkyl, hydroxy(2-6C)alkenyl, hydoxy(2-6C)alkynyl, (1-6C)alkanoyl(1-6C)alkyl and oxime derivatives thereof and O-(1-6C)alkyl ethers of said oxime derivatives; and, in addition, optionally bears one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

More particularly, Ar is phenyl which bears one or more substituents independently selected from (1-6C) alkoxycarbonyl(1-6C)alkyl, (1-6C)alkoxycarbonyl(-6C) alkoxy, (1-6C)alkoxy(1-6C)alkoxy, (1-6C)alkoxy(1-6C) alkoxy(1-6C)alkyl, di-[(1-6C)alkoxy](1-6C)alkoxy, phenoxy(1-6C)alkoxy, (1-6C)alkoxycarbonyl(2-6C)alkenyl, (1- 6C)alkoxycarbonyl(1-6C)alkoxycarbonyl(1-6C)alkyl, (1-6C)alkoxy(1-6C)alkoxycarbonyl(1-6C)alkyl, (1-6C) alkoxy(1-6C)alkoxycarbonyl, (1-6C)alkylthio(1-6C)alkoxy, (1-6C)alkoxy(1-6C)alkyl, (1-6C)alkoxycarbonyl(1-6C) alkylcarbamoyl, (1-6C)alkoxy(1-6C)alkylcarbamoyl, (1-6C)alkanoyloxy(1-6C)alkyl, cyano(1-6C)alkoxy, carboxy(1-6C)alkyl, cyano(1-6C)alkyl, phenyl(1-6C)alkyl, hydroxy(1-6C)alkyl, (1-6C)alkoxycarbonyl(1-6C)alkanoyl, (1-6C)alkylthio(1-6C)alkyl, (2-6C)alkenyl(1-6C)alkoxy(1-6C)alkyl, and (1-6C)alkanoyl(1-6C)alkyl and oxime derivatives thereof and O-(1-6C)alkyl ethers of said oxime derivatives; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl] amino N-(1-6C)alkylcarbamoyl, di-N,N-[(1-6C)alkyl] carbamoyl, (1-6C)alkoxycarbonyl, (1-6C)alkylthio, (1-6C) alkylsulphinyl, (1-6C)alkylsulphonyl, halogeno (1-6C) alkyl, (1-6C)alkanoylamino, (1-4C)alkylenedioxy, (1-6C) alkanoyl and oxime derivatives thereof and O-(1-6C)alkyl ethers of said oxime derivatives.

In general, it is preferred that Ar is phenyl which bears one or more substituents selected from (1-6C)alkoxycarbonyl(1-6C)alkyl, (1-6C)alkoxy(1-6C)alkoxy, (1-6C)alkoxy(1-6C)alkoxy(1-6C)alkyl, (1-6C)alkylthio(1-6C)alkoxy, (1-6C) alkoxy(1-6C)alkyl, (1-6C)alkoxy(1-6C)alkoxycarbonyl(1-6C)alkyl, (1-6C)alkoxycarbonyl(1-6C)alkoxy, hydroxy(1-6C)alkyl, (1-6C)alkanoyl(1-6C)alkyl, (1-6C) alkoxycarbonyl(1-6C)alkanoyl and carboxy(1-6C)alkyl; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C) alkylsulphinyl, (1-6C)alkylsulphonyl, halogeno (1-6C) alkyl, (1-6C)alkanoylamino, (1-4C)alkylenedioxy, (1-6C) alkanoyl and oxime derivatives thereof and O-(1-6C)alkyl ethers of said oxime derivatives.

More preferably, Ar is phenyl which bears a substituent selected from (1-6C)alkoxycarbonyl(1-6C)alkyl and carboxy(1-6C)alkyl, and which optionally bears one or more substituents selected from the optional substituents defined in the preceding paragraph. (especially (2-6C)alkenyl such as allyl).

In general, for example, it is preferred that Ar bears one, two, three or four substituents.

In particular, X is selected from —C≡C—, —CH=CH, —CH$_2$CH$_2$—, —CH$_2$O—, —CH$_2$S(O)$_n$— (n=0,1 or 2), —CH$_2$NH—, —CH$_2$CO— and —COCH$_2$; more particularly from —C≡C—, —CH=CH—, —CH$_2$CH$_2$—, —CH$_2$O—, —CH$_2$S— and —CH$_2$NH—.

In general it is preferred, for example, that R$^1$ is hydroxy and R$^2$ is hydrogen.

In general it is preferred, for example, that X is —C≡C—, —CH$_2$CH$_2$—, —CH$_2$O or —CH—CH—, especially —C≡C—.

In general, it is preferred, for example, that Ar is phenyl which bears one or more (1-6C)alkoxycarbonyl(1-6C)alkyl substituents and which, in addition, optionally bears one or more substituents selected from the optional substituents defined above.

Specific values of interest for X include, for example, —C≡C—, —CH=CH—, —CH$_2$CH$_2$— and —CH$_2$O—.

Specific values for R$^1$ and R$^2$ include, for example, R$^1$ is hydroxy and R$^2$ is hydrogen.

Specific values for Ar include, for example, phenyl which bears one or more (particularly one or two) substituents selected from (1-6C)alkoxy(1-6C)alkoxycarbonyl(1-6C) alkyl (such as methoxyethoxycarbonylethyl), (1-6C)alkoxy (1-6C)alkyl (such as methoxypropyl), (1-6C) alkoxycarbonyl(1-6C)alkyl (such as ethoxycarbonylethyl, methoxycarbonylethyl, methoxycarbonylpropyl, methoxycarbonylbutyl, iso-butoxycarbonylethyl, hexyloxycarbonylethyl, methoxycarbonylpropyl, methoxycarbonylpentyl), (1-6C)alkoxycarbonyl(1-6C) alkoxy (such as methoxycarbonylmethoxy), (1-6C)alkoxy (1-6C)alkoxy (such as methoxyethoxy), (1-6C)alkoxy(1-6C)alkoxy(1-6C)alkyl (such as methoxyethoxymethyl, methoxyethoxyethyl), carboxy(1-6C)alkyl (such as carboxyethyl, carboxypropyl), hydroxyalkyl (such as hydroxymethyl), (1-6C)alkanoyl(1-6C)alkyl (such as ethanoylethyl) and oxime derivatives thereof and O-(1-6C) alkyl ethers of said oximes, and (1-6C)alkoxycarbonyl(1-6C)alkanoyl (such as ethoxycarbonylethanoyl, ethoxycarbonylpropanoyl); and optionally one or more substituents selected from the optional substituents mentioned above and in particular one or two substituents selected from (1-6C)alkyl (such as methyl), (2-6C)alkenyl (such as allyl), halogeno (such as fluoro), (1-6C)alkoxy (such as methoxy) and (1-6C)alkanoyl (such as formyl).

Values of Ar of particular interest include those in which Ar is phenyl which bears a substituent at the 4-position selected from (1-6C)alkoxycarbonyl(1-6C)alkyl, (1-6C) alkoxy(1-6C)alkoxy, (1-6C)alkoxy(1-6C)alkoxy(1-6C) alkyl, (1-6C)alkylthio(1-6C)alkoxy, (1-6C)alkoxy(1-6C) alkyl, (1-6C)alkoxy(1-6C)alkoxycarbonyl(1-6C)alkyl, (1-6C)alkoxycarbonyl(1-6C)alkoxy, hydroxy(1-6C)alkyl, (1-6C)alkanoyl(1-6C)alkyl, (1-6C)alkoxycarbonyl(1-6C) alkanoyl and carboxy(1-6C)alkyl; and which optionally bears a substituent at the 2-position selected from the optional substituents defined in the preceding paragraph (especially (2-6C)alkenyl such as allyl).

In one embodiment of the present invention, $R^1$ and $R^2$ are both hydrogen; and X and Ar have any of the meanings defined above.

In a further embodiment of the present invention, $R^1$ and $R^2$ are joined together so that $CR^1$–$CR^2$ is a double bond; and X and Ar have any of the meanings defined above.

In a further embodiment of the present invention $R^1$ is hydroxy, $R^2$ is hydrogen; and X and Ar have any of the meanings defined above.

In a further embodiment there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C)alkenyl, (2-6C)alkynyl, (1-6C)alkoxy, (1-6C) alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkanoyl and oxime derivatives thereof and O-(1-6C)alkyl ethers of said oximes, (1-6C)alkylthio, (1-6C)alkylsulphinyl and (1-6C)alkylsulphonyl when substituted by one or more groups selected from (1-6C)alkoxycarbonyl, (1-6C) alkanoyl and oxime derivatives thereof and O-(1-6C) alkyl ethers of said oxime derivatives, (1-6C) alkanoylamino, (1-6C)alkanoyloxy, (1-6C)alkanoyloxy (1-6C)alkyl, carbamoyl, N-(1-6C)alkylcarbamoyl, N,N-di[(1-6C)alkylcarbamoyl, amino, (1-6C) alkylamino, di-[(1-6C)alkyl]amino, (1-6C)alkoxy, (2-6C)alkenyloxy, (1-6C)alkylthio, (1-6C) alkylsulphinyl, (1-6C)alkylsulphonyl, halogeno(1-6C) alkyl, (2-6C)alkenyl, (2-6C)alkynyl, cyano, nitro, hydroxy and carboxy;

and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl] amino N-(1-6C)alkylcarbamoyl, di-N,N-[(1-6C)alkyl] carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C) alkylenedioxy, (1-6C)alkanoyl and oxime derivatives thereof and O-(1-6C)alkyl ethers of said oxime derivatives. provided that when X is —$OCH_2$—, —$NHCH_2$— or —$S(O)_nCH_2$— (wherein n is 0,1 or 2), then $R^1$ is not hydroxy.

In a prefered embodiment of the present invention $R^1$ is hydroxy, $R^2$ is hydrogen, X is selected from —$CH_2CH_2$—, —CH=CH—, —C≡C— and —$CH_2O$— (especially —C≡C—); Ar is phenyl which bears one or more substituents independently selected from (1-6C)alkoxycarbonyl(1-6C)alkyl, (1-6C)alkoxycarbonyl(1-6C)alkoxy, (1-6C)alkoxy (1-6C)alkoxy, (1-6C)alkoxy(1-6C)alkoxy(1-6C)alkyl, di-[(1-6C)alkoxy](1-6C)alkoxy, (1-6C)alkoxycarbonyl(2-6C) alkenyl, (1-6C)alkoxycarbonyl(1-6C)alkoxycarbonyl(1-6C) alkyl, (1-6C)alkoxy(1-6C)alkoxycarbonyl(1-6C)alkyl, (1-6C)alkoxy(1-6C)alkoxycarbonyl, (1-6C)alkylthio(1-6C) alkoxy, (1-6C)alkoxy(1-6C)alkyl, (1-6C)alkoxycarbonyl(1-6C)alkylcarbamoyl, (1-6C)alkoxy(1-6C)alkylcarbamoyl, (1-6C)alkanoyloxy(1-6C)alkyl, cyano(1-6C)alkoxy, carboxy(1-6C)alkyl, cyano(1-6C)alkyl, hydroxy(1-6C) alkyl, (1-6C)alkoxycarbonyl(1-6C)alkanoyl, (1-6C) alkylthio(1-6C)alkyl, (2-6C)alkenyl(1-6C)alkoxy(1-6C) alkyl, and (1-6C)alkanoyl(1-6C)alkyl and oxime derivatives thereof and O-(1-6C)alkyl ethers of said oxime derivatives; and wherein Ar may optionally bear one or more substituents independently selected from halogeno, hydroxy, amino, nitro, cyano, carboxy, carbamoyl, (1-6C)alkyl, (2-6C) alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C) alkylthio, (1-6C)alkylsulphinyl, (1-6C)alkylsulphonyl, halogeno(1-6C)alkyl, (1-6C)alkanoylamino, (1-4C) alkylenedioxy, (1-6C)alkanoyl and oxime derivatives thereof and O-(1-6C)alkyl ethers of said oxime derivatives.

Particular, preferred and specific values include the appropriate values mentioned above.

In a specific embodiment, $R^1$ is hydroxy, $R^2$ is hydrogen X is selected from —$CH_2CH_2$—, —CH=CH—, —C≡C— and —$CH_2O$ (especially —C≡C—); Ar is phenyl which bears one or more substituents selected from (1-6C)alkoxy (1-6C)alkoxycarbonyl(1-6C)alkyl, (1-6C)alkoxy(1-6C) alkyl, (1-6C)alkoxycarbonyl(1-6C)alkyl, (1-6C) alkoxycarbonyl(1-6C)alkoxy, (1-6C)alkoxy(1-6C)alkoxy, (1-6C)alkoxy(1-6C)alkoxy(1-6C)alkyl, carboxy(1-6C) alkyl, (1-6C)alkanoyl(1-6C)alkyl and oxime derivatives thereof and O-(1-6C)alkyl ethers of said oximes, (1-6C) alkoxycarbonyl(1-6C)alkanoyl; and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C) alkynyl, (1-6C)alkoxy, (1-6C)alkylamino, di-[(1-6C)alkyl] amino N-(1-6C)alkylcarbamoyl, di-N,N-[(1-6C)alkyl] carbamoyl, (1-6C)alkoxycarbonyl, (1-6C)alkylthio, (1-6C) alkylsulphinyl, (1-6C)alkylsulphonyl, halogeno(1-6C)alkyl, (1-6C)alkanoylamino, (1-4C)alkylenedioxy, (1-6C)alkanoyl and oxime derivatives thereof and O-(1-6C)alkyl ethers of said oxime derivatives.

In an embodiment of particular interest $R^1$ is hydroxy, $R^2$ is hydrogen, X is —C≡C—, Ar is phenyl which bears a substituent selected from (1-6C)alkoxycarbonyl(1-6C)alkyl and carboxy(1-6C)alkyl, and which optionally bears a further substituent of (2-6C)alkenyl (such as allyl).

In a further embodiment of the present invention there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C) alkenyl, (2-6C)alkynyl, (1-6C)alkoxy, (1-6C)alkoxy(1-6C)alkyl, (1-6C)alkylamino, di-[(1-6C)alkyl]amino, (1-6C)alkylthio, (1-6C)alkylsulphinyl and (1-6C) alkylsulphonyl when substituted by one or more groups selected from (1-6C)alkoxycarbonyl, phenoxycarbonyl, (1-6C)alkanoyl, (1-6C) alkanoylamino, (1-6C)alkanoyloxy, N-(1-6C) alkylcarbamoyl, N,N-di[(1-6C)alkylcarbamoyl, (1-6C) alkoxy, (2-6C)alkenyloxy, (1-6C)alkylthio, (1-6C) alkylsulphinyl, (1-6C)alkylsulphonyl, halogeno(1-6C) alkyl, phenyl, phenoxy, cyano, nitro, and hydroxy; and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl] amino N-(1-6C)alkylcarbamoyl, di-N,N-[(1-6C)alkyl] carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C) alkylenedioxy, (1-6C)alkanoyl and oxime derivatives thereof and O-(1-6C)alkyl ethers of said oxime derivatives; provided that when X is
—$OCH_2$—, —$NHCH_2$— or —$S(O)_nCH_2$— (wherein n is 0,1 or 2), then $R^1$ is not hydroxy; and provided that when a substituent on Ar includes a phenyl moiety, X is —$OCH_2$—, then $R^1$ and $R^2$ are not both hydrogen, or joined together so that $CR^1$–$CR^2$ is a double bond.

In a further embodiment there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH═CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C)alkenyl, (2-6C)alkynyl, (1-6C)alkoxy, (1-6C)alkoxy(1-6C)alkyl, (1-6C)alkylamino, di-[(1-6C)alkyl]amino, (1-6C)alkylthio, (1-6C)alkylsulphinyl and (1-6C) alkylsulphonyl when substituted by one or more groups selected from (1-6C)alkoxycarbonyl, phenoxycarbonyl, (1-6C)alkanoyl, (1-6C) alkanoylamino, (1-6C)alkanoyloxy, N-(1-6C) alkylcarbamoyl, N,N-di[(1-6C)alkylcarbamoyl, (1-6C) alkoxy, (2-6C)alkenyloxy, (1-6C)alkylthio, (1-6C) alkylsulphinyl, (1-6C)alkylsulphonyl, halogeno(1-6C) alkyl, phenyl, phenoxy, cyano, nitro, and hydroxy; and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl] amino N-(1-6C)alkylcarbamoyl, di-N,N-[(1-6C)alkyl] carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C) alkylenedioxy, (1-6C)alkanoyl and oxime derivatives thereof and O-(1-6C)alkyl ethers of said oxime derivatives; provided that when X is
—$OCH_2$—, —$NHCH_2$— or —$S(O)_nCH_2$— (wherein n is 0,1 or 2), then $R^1$ is not hydroxy; and provided that when a substituent on Ar includes a phenyl moiety, then $R^1$ is hydroxy.

Particular, preferred and specific values include the appropriate values mentioned above.

In particular Ar is phenyl which bears one or more substituents independently selected from (1-6C) alkoxycarbonyl(1-6C)alkyl, (1-6C)alkoxycarbonyl(1-6C) alkoxy, (1-6C)alkoxy(1-6C)alkoxy, (1-6C)alkoxy(1-6C) alkoxy(1-6C)alkyl, di-[(1-6C)alkoxy(1-6C)alkyl](1-6C) alkoxy, phenoxy(1-6C)alkoxy, (1-6C)alkoxy(1-6C) alkoxycarbonyl, di-[(1-6C)alkoxy](1-6C)alkyl, (1-6C) alkylamino(1-6C)alkyl, di-[(1-6C)alkyl]amino(1-6C)alkyl, (1-6C)alkylcarbonylamino(1-6C)alkyl, (3-6C)cycloalkyl(1-6C)alkoxy, (2-6C)alkenyloxy(1-6C)alkyl, carbamoyl(1-6C) alkyl, N-(1-6C)alkylcarbamoyl(1-6C)alkyl, phenyl(1-6C) alkyl, N,N-di-[(1-6C)alkyl]carbamoyl(1-6C)alkyl; (1-6C) alkoxycarbonyl(2-6C)alkenyl, (1-6C)alkoxycarbonyl(2-6C) alkynyl, cyano(1-6C)alkoxy, cyano(1-6C)alkoxy(1-6C) alkyl, nitro(1-6C)alkoxy, nitro(1-6C)alkoxy(1-6C)alkyl, and (1-6C)alkoxycarbonyl(1-6C)alkylthio; and, in addition, optionally bears one or more substituents independently selected from halogeno, hydroxy, amino, nitro, cyano, carboxy, carbamoyl, (1-6C)alkyl, (2-6C)alkenyl, (2-6C) alkynyl, (1-6C)alkoxy, (1-6C)alkylamino, di-[(1-6C)alkyl] amino N-(1-6C)alkylcarbamoyl, di-N,N-[(1-6C)alkyl] carbamoyl, (1-6C)alkoxycarbonyl, (1-6C)alkylthio, (1-6C) alkylsulphinyl, (1-6C)alkylsulphonyl, halogeno (1-6C) alkyl, (1-6C)alkanoylamino, (1-4C)alkylenedioxy, (1-6C) alkanoyl and oxime derivatives thereof and O-(1-6C)alkyl ethers of said oxime derivatives.

More particularly, Ar is phenyl which bears one or more substituents independently selected from (1-6C) alkoxycarbonyl(1-6C)alkyl, (1-6C)alkoxycarbonyl(1-6C) alkoxy, (1-6C)alkoxy(1-6C)alkoxy, (1-6C)alkoxy(1-6C) alkoxy(1-6C)alkyl, di-[1-6C)alkoxy(1-6C)alkyl](1-6C) alkoxy, phenyloxy(1-6C)alkoxy, phenyl(1-4C)alkyl and (1-6C)alkoxy(1-6C)alkoxycarbonyl; and optionally bears one or more further substituents selected from halogeno, hydroxy, amino, nitro, cyano, carboxy, carbamoyl, (1-6C) alkyl, (2-6C)alkenyl, (2-6C)alkynyl, (1-6C)alkoxy, (1-6C) alkylamino, di-[(1-6C)alkyl]amino N-(1-6C) alkylcarbamoyl, di-N,N-[(1-6C)alkyl]carbamoyl, (1-6C) alkoxycarbonyl, (1-6C)alkylthio, (1-6C)alkylsulphinyl, (1-6C)alkylsulphonyl, halogeno (1-6C)alkyl, (1-6C) alkanoylamino, (1-4C)alkylenedioxy, (1-6C)alkanoyl and oxime derivatives thereof and O-(1-6C)alkyl ethers of said oxime derivatives;

Specific values for Ar include, for example, phenyl which bears one or more (particularly one or two) substituent selected from (1-6C)alkoxycarbonyl(1-6C)alkyl (such as ethoxycarbonylmethyl, methoxycarbonylmethyl, ethoxycarbonylethyl), (1-6C)alkoxycarbonyl(1-6C)alkoxy (such as ethoxycarbonylmethoxy), (1-6C)alkoxy(1-6C) alkoxy(such as methoxyethoxy or methoxyethoxy), di-[1-6C)alkoxy(1-6C)alkyl](1-6C)alkoxy (such as 1-(methoxymethyl)-2-methoxyethoxy), (1-6C)alkoxy(1-6C) alkoxy(1-6C)alkyl (such as methoxyethoxymethyl), phenoxy(1-6C)alkoxy (such as phenoxyethoxy), (1-6C) alkoxy(1-6C)alkoxycarbonyl (such as methoxyethoxycarbonyl) and benzyl; and optionally one or more (in particular, one or two) substituents selected from halogeno (such as chloro), (1-6C)alkanoylamino (such as propionamido), (1-6C)alkyl (such as methyl) and (2-6C) alkenyl (such as allyl).

In a further embodiment of the present invention $R^1$ is hydroxy, $R^2$ is hydrogen, X is selected from —$CH_2CH_2$—, —CH═CH—, —C≡C— and —$CH_2O$— (especially —C≡C—);

Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-[(1-6C)alkoxy(1-6C)alkyl](1-6C)alkoxy, phenyloxy(1-6C)alkoxy, phenyl(1-4C)alkyl and (1-6C)alkoxy(1-6C)alkoxycarbonyl; and Ar optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

Particular, preferred and specific values include the appropriate values mentioned above.

In a specific embodiment, $R^1$ is hydroxy, $R^2$ is hydrogen X is selected from —$CH_2CH_2$—, —CH—CH—, —C≡C— and —$CH_2O$ (especially —C≡C—);

Ar is phenyl which bears a substituent selected from (1-6C)alkoxycarbonyl(1-6C)alkyl (such as ethoxycarbonylmethyl, methoxycarbonylmethyl, ethoxycarbonylethyl), (1-6C)alkoxycarbonyl(1-6C)alkoxy (such as ethoxycarbonylmethoxy), (1-6C)alkoxy(1-6C)alkoxy(such as methoxyethoxy or methoxyethoxy), di-[1-6C)alkoxy(1-6C)alkyl](1-6C)alkoxy (such as 1-(methoxymethyl)-2-methoxyethoxy), (1-6C)alkoxy(1-6C)alkoxy(1-6C)alkyl (such as methoxyethoxymethyl), phenoxy(1-6C)alkoxy (such as phenoxyethoxy), (1-6C)alkoxy(1-6C)alkoxycarbonyl (such as methoxyethoxycarbonyl) and benzyl; and optionally one or more (in particular, one or two) substituents selected from halogeno (such as chloro), (1-6C)alkanoylamino (such as propionamido), (1-6C)alkyl (such as methyl) and (2-6C)alkenyl (such as allyl).

In a further embodiment there is provided a compound of formula I (formula set out hereinafter together with the other chemical formulae referred to herein), or a pharmaceutically acceptable salt thereof, wherein:
$R^1$ is hydrogen or hydroxy;
$R^2$ is hydrogen; or
$R^1$ and $R^2$ are joined together so that $CR^1$–$CR^2$ is a double bond;
X is selected from —$CH_2CH_2$—, —CH═CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);
Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkylthio, (1-6C)alkylsulphinyl and (1-6C)alkylsulphonyl when substituted by one or more groups selected from (1-6C)alkoxycarbonyl, phenoxycarbonyl, (1-6C)alkanoyl, (1-6C)alkanoylamino, (1-6C)alkanoyloxy, N-(1-6C)alkylcarbamoyl, N,N-di[(1-6C)alkylcarbamoyl, (1-6C)alkoxy, (2-6C)alkenyloxy, (1-6C)alkylthio, (1-6C)alkylsulphinyl, (1-6C)alkylsulphonyl, halogeno(1-6C)alkyl, phenyl, phenoxy, cyano, nitro, hydroxy and carboxy;

and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives. provided that when X is
—$OCH_2$—, —$NHCH_2$— or —$S(O)_nCH_2$— (wherein n is 0,1 or 2), then $R^1$ is not hydroxy; and provided that when a substituent on Ar includes a phenyl moiety, X is —$OCH_2$—, then $R^1$ and $R^2$ are not both hydrogen, or joined together so that $CR^1$–$CR^2$ is a double bond.

In particular, according to the present invention there is provided a compound of formula I (formula set out hereinafter together with the other chemical formulae referred to herein), or a pharmaceutically acceptable salt thereof, wherein:
$R^1$ is hydrogen or hydroxy;
$R^2$ is hydrogen; or
$R^1$ and $R^2$ are joined together so that $CR^1$–$CR^2$ is a double bond;
X is selected from —$CH_2CH_2$—, —CH═CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);
Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkylthio, (1-6C)alkylsulphinyl and (1-6C)alkylsulphonyl when substituted by one or more groups selected from (1-6C)alkoxycarbonyl, phenoxycarbonyl, (1-6C)alkanoyl, (1-6C)alkanoylamino, (1-6C)alkanoyloxy, N-(1-6C)alkylcarbamoyl, N,N-di[(1-6C)alkylcarbamoyl, (1-6C)alkoxy, (2-6C)alkenyloxy, (1-6C)alkylthio, (1-6C)alkylsulphinyl, (1-6C)alkylsulphonyl, halogeno(1-6C)alkyl, phenyl, phenoxy, cyano, nitro, hydroxy and carboxy;
and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives; provided that when X is
—$OCH_2$—, $NRCH_2$— or —$S(O)_nCH_2$— (wherein n is 0,1 or 2), then $R^1$ is not hydroxy; and provided that when a substituent on Ar includes a phenyl moiety, then $R^1$ is hydroxy.

Particular, preferred and specific values include the appropriate values mentioned above.

In particular Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-[(1-6C)alkoxy(1-6C)alkyl](1-6C)alkoxy, phenoxy(1-6C)alkoxy, (1-6C)alkoxy(1-6C)alkoxycarbonyl, di-[(1-6C)alkoxy](1-6C)alkyl, (1-6C)alkylamino(1-6C)alkyl, di-[(1-6C)alkyl]amino(1-6C)alkyl, (1-6C)alkylcarbonylamino(1-6C)alkyl, (3-6C)cycloalkyl(1-6C)alkoxy, (2-6C)alkenyloxy(1-6C)alkyl, carbamoyl(1-6C)alkyl, N-(1-6C)alkylcarbamoyl(1-6C)alkyl, phenyl(1-6C)alkyl, N,N-di-[(1-6C)alkyl]carbamoyl(1-6C)alkyl; (1-6C)alkoxycarbonyl(2-6C)alkenyl, (1-6C)alkoxycarbonyl(2-6C)alkynyl, cyano(1-6C)alkoxy, cyano(1-6C)alkoxy(1-6C)alkyl, nitro(1-6C)alkoxy, nitro(1-6C)alkoxy(1-6C)alkyl, (1-6C)alkoxycarbonyl(1-6C)alkylthio, (1-6C)alkoxycarbonyl(1-6C)alkoxycarbonyl(1-6C)alkyl, (1-6C)alkoxy(1-6C)alkoxycarbonyl(1-6C)alkyl, (1-6C)alkylthio(1-6C)alkoxy, (1-6C)alkoxy(1-6C)alkyl, (1-6C)alkoxycarbonyl (1-6C)alkylcarbamoyl, (1-6C)alkoxy(1-6C)alkylcarbamoyl, (1-6C)alkanoyloxy(1-6C)alkyl, cyano(1-6C)alkyl, carboxy(1-6C)alkyl and hydroxy(1-6C)alkyl; and, in addition, optionally bears one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

More particularly, Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-[(1-6C)alkoxy](1-6C)alkoxy, phenoxy(1-6C)alkoxy, (1-6C)alkoxycarbonyl(2-6C)alkenyl, (1-6C)alkoxycarbonyl(1-6C)alkoxycarbonyl(1-6C)alkyl, (1-6C)alkoxy(1-6C)alkoxycarbonyl(1-6C)alkyl, (1-6C)alkoxy(1-6C)alkoxycarbonyl, (1-6C)alkylthio(1-6C)alkoxy, (1-6C)alkoxy(1-6C)alkyl, (1-6C)alkoxycarbonyl(1-6C)alkylcarbamoyl, (1-6C)alkoxy(1-6C)alkylcarbamoyl, (1-6C)alkanoyloxy(1-6C)alkyl, cyano(1-6C)alkoxy, carboxy(1-6C)alkyl, cyano(1-6C)alkyl, phenyl(1-6C)alkyl, hydroxy(1-6C)alkyl; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

In general, it is preferred that Ar is phenyl which bears one or more substituents selected from (1-6C)alkoxycarbonyl(1-6C)alkyl, (1-6C)alkoxy(1-6C)alkoxy, (1-6C)alkoxy(1-6C)alkoxy(1-6C)alkyl, (1-6C)alkylthio(1-6C)alkoxy, (1-6C)alkoxy(1-6C)alkyl and carboxy(1-6C)alkyl; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

In a further embodiment there is provided there is provided a compound of formula I (formula set out hereinafter together with the other chemical formulae referred to herein), or a pharmaceutically acceptable salt thereof, wherein:

R is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl carbamoyl, (1-6C)alkylthio, (1-6C)alkylsulphinyl and (1-6C)alkylsulphonyl when substituted by one or more groups selected from (1-6C)alkoxycarbonyl, (1-6C)alkanoyl and oxime derivatives thereof and O-(1-6C)alkyl ethers of said oxime derivatives, (1-6C)alkanoylamino, (1-6C)alkanoyloxy, N-(1-6C)alkylcarbamoyl, N,N-di[(1-6C)alkylcarbamoyl, amino, (1-6C)alkylamino, di-[(1-6C)alkylamino, (1-6C)alkoxy, (2-6C)alkenyloxy, (1-6C)alkylthio, (1-6C)alkylsulphinyl, (1-6C)alkylsulphonyl, halogeno(1-6C)alkyl, phenyl, phenoxy, cyano, nitro, hydroxy and carboxy;

and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives. provided that when X is
—$OCH_2$—, —$NHCH_2$— or —$S(O)_nCH_2$— (wherein n is 0,1 or 2), then $R^1$ is not hydroxy; and provided that when a substituent on Ar includes a phenyl moiety, X is —$OCH_2$—, then $R^1$ and $R^2$ are not both hydrogen, or joined together so that $CR^1$ –$CR^2$ is a double bond.

In particular, according to the present invention there is provided a compound of formula I (formula set out hereinafter together with the other chemical formulae referred to herein), or a pharmaceutically acceptable salt thereof, wherein:

$R^1$ is hydrogen or hydroxy;

$R^2$ is hydrogen; or $R^1$ and $R^2$ are joined together so that $CR^1$–$CR^2$ is a double bond;

X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);

Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkylthio, (1-6C)alkylsulphinyl and (1-6C)alkylsulphonyl when substituted by one or more groups selected from (1-6C)alkoxycarbonyl, phenoxycarbonyl, (1-6C)alkanoyl, and oxime derivatives thereof and O-(1-6C)alkyl ethers of said oxime derivatives, (1-6C)alkanoylamino, (1-6C)alkanoyloxy, N-(1-6C)alkylcarbamoyl, N,N-di[(1-6C)alkylcarbamoyl, amino, (1-6C)alkylamino, di-[(1-6C)alkyl]amino, (1-6C)alkoxy, (2-6C)alkenyloxy, (1-6C)alkylthio, (1-6C)alkylsulphinyl, (1-6C)alkylsulphonyl, halogeno(1-6C)alkyl, phenyl, phenoxy, cyano, nitro, hydroxy and carboxy;

and wherein Ar and/or a phenyl moiety in any of said groups mentioned above may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl] carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C) alkylenedioxy, (1-6C)alkanoyl and oxime derivatives thereof and O-(1-6C)alkyl ethers of said oxime derivatives; provided that when X is
—OCH$_2$—, —NHCH$_2$— or —S(O)$_n$— CH$_2$—
(wherein n is 0,1 or 2), then R$^1$ is not hydroxy; and provided that when a substituent on Ar includes a phenyl moiety, then R$^1$ is hydroxy.

In particular Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-[(1-6C)alkoxy](1-6C)alkoxy, phenoxy(1-6C)alkoxy, h(1-6C)alkoxy(1-6C)alkoxycarbonyl, di-[(1-6C)alkoxy](1-6C)alkyl, (1-6C)alkylamino(1-6C)alkyl, di-[(1-6C)alkyl]amino(1-6C)alkyl, (1-6C)alkylcarbonylamino(1-6C)alkyl, (3-6C)cycloalkyl(1-6C)alkoxy, (2-6C)alkenyloxy(1-6C)alkyl, carbamoyl(1-6C) alkyl, N-(1-6C)alkylcarbamoyl(1-6C)alkyl, phenyl(1-6C) alkyl, N,N-di-[(1-6C)alkyl]carbamoyl(1-6C)alkyl; (1-6C)alkoxycarbonyl(2-6C)alkenyl, (1-6C)alkoxycarbonyl(2-6C)alkynyl, cyano(1-6C)alkoxy, cyano(1-6C)alkoxy(1-6C)alkyl, nitro(1-6C)alkoxy, nitro(1-6C)alkoxy(1-6C)alkyl, (1-6C)alkoxycarbonyl(1-6C)alkylthio, (1-6C)alkoxycarbonyl(1-6C)alkoxycarbonyl(1-6C)alkyl, (1-6C)alkoxy(1-6C)alkoxycarbonyl(1-6C)alkyl, (1-6C)alkylthio(1-6C)alkoxy, (1-6C)alkoxy(1-6C)alkyl, (1-6C)alkoxycarbonyl(1-6C)alkylcarbamoyl, (1-6C)alkoxy(1-6C)alkylcarbamoyl, (1-6C)alkanoyloxy(1-6C)alkyl, cyano(1-6C)alkyl, carboxy(1-6C)alkyl, hydroxy(1-6C)alkyl (1-6C)alkylamino(1-6C)alkyl, di-[(1-6C)alkyl]amino(1-6C)alkyl, (1-6C)alkylamino(1-6C)alkoxycarbonyl(1-6C)alkyl, di-[(1-6C)alkyl]amino(1-6C)alkoxycarbonyl(1-6C)alkyl, (1-6C)alkylcarbamoyl(1-6C)alkoxycarbonyl, di-[(1-6C)alkyl]carbamoyl(1-6C)alkoxycarbonyl, carbamoyl(1-6C)alkoxycarbonyl, (1-6C)alkoxycarbonyl(1-6C)alkoxy(1-6C)alkyl, di-[(1-6C)alkyl]amino(1-6C)alkoxycarbonyl, (1-6C)alkoxycarbonyl(1-6C)alkanoyl, (1-6C)alkoxy(1-6C)alkoxy(1-6C)alkanoyl, (1-6C)alkylthio(1-6C)alkyl, (2-6C)alkenyl(1-6C)alkoxy(1-6C)alkyl, (2-6C)alkynyl(1-6C)alkoxy(1-6C)alkyl, halogeno(1-6C)alkyl(1-6C)alkoxycarbonyl, phenoxycarbonyl, (1-6C)alkanoyl(1-6C)alkyl and oxime derivatives thereof and O-(1-6C)alkyl ethers of said oxime derivatives; and, in addition, optionally bears one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkylamino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

More particularly, Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-[(1-6C)alkoxy](1-6C)alkoxy, phenoxy(1-6C)alkoxy, (1-6C)alkoxycarbonyl(2-6C)alkenyl, (1-6C)alkoxycarbonyl(1-6C)alkoxycarbonyl(1-6C)alkyl, (1-6C)alkoxy(1-6C)alkoxycarbonyl(1-6C)alkyl, (1-6C)alkoxy(1-6C)alkoxycarbonyl, (1-6C)alkylthio(1-6C)alkoxy, (1-6c)alkoxy(1-6C)alkyl, (1-6C)alkoxycarbonyl(1-6C)alkylcarbamoyl, (1-6C)alkoxy(1-6C)alkylcarbamoyl, (1-6C)alkanoyloxy(1-6C)alkyl, cyano(1-6C)alkoxy, carboxy(1-6C)alkyl, cyano(1-6C)alkyl, phenyl(1-6C)alkyl, hydroxy(1-6C)alkyl, (1-6C)alkoxycarbonyl(1-6C)alkanoyl, (1-6C)alkylthio(1-6C)alkyl, (2-6C)alkenyl(1-6C)alkoxy(1-6C)alkyl, and (1-6C)alkanoyl(1-6C)alkyl and oxime derivatives thereof and O-(1-6C)alkyl ethers of said oxime derivatives; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

In general, it is preferred that Ar is phenyl which bears one or more substituents selected from (1-6C)alkoxycarbonyl(1-6C)alkyl, (1-6C)alkoxy(1-6C)alkoxy, (1-6C)alkoxy(1-6C)alkoxy(1-6C)alkyl, (1-6C)alkylthio(1-6C)alkoxy, (1-6C)alkoxy(1-6C)alkyl (1-6C)alkoxy(1-6C)alkoxycarbonyl(1-6C)alkyl, (1-6C)alkoxycarbonyl(1-6C)alkoxy, hydroxy(1-6C)alkyl, (1-6C)alkanoyl(1-6C)alkyl, (1-6C)alkoxycarbonyl(1-6C)alkanoyl, and carboxy(1-6C)alkyl; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl and oxime derivatives thereof and O-(1-6C)alkyl ethers of said oxime derivatives.

Compounds of the invention which are of particular interest include the compounds described in the accompanying Examples (and their pharmaceutically-acceptable salts), and are hence provided as a further feature of the present invention. In particular, the present invention provides a compound as described in Example 1, 23, 26, 27, 28, 30, 35, 44, 55, 65, 66, 67, 68, 69, 83, 84, 85, 115 and 120 and their pharmaceutically acceptable salts.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy] those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example, $R^1$, $R^2$, X and Ar may take any of the meanings hereinbefore defined.

Thus, according to the present invention there is also provided a process for preparing a compound of formula I, or a pharmaceutically-acceptable salt thereof, which process comprises:

(a) For those compounds of formula I in which $R^1$ and $R^2$ are both hydrogen, reducing a compound of formula I in which $R^1$ and $R^2$ are joined together so that $CR^1$–$CR^2$ is a double bond.

The reduction may be carried out, for example, by catalytic hydrogenation, or by reaction with a suitable reducing agent. Suitable reaction conditions include, for example, catalytic hydrogenation using a catalyst which comprises a noble metal. Particular catalysts include palladium, platinum and nickel (especially when in the finely divided state known as raney nickel), and catalysts in which the noble metal is supported on an inert carrier such as carbon. A specific example of a supported catalyst is Pd/C. The reduction is conveniently carried out in a solvent of, for example, an alcohol (such as ethanol), and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example, 0–60° C. It may be preferable to cool the reaction below ambient temperature (eg. to about 0° C.) during the reduction. The borane generated may be hydrolysed by treatment with an organic acid such as acetic acid, which hydrolysis may be carried out at 0–60° C., and may be accelerated by heating (eg. refluxing).

(b) For compounds of formula I in which $R^1$ and $R^2$ are joined together so that $CR^1$–$CR^2$ is a double bond, dehydrating a compound of formula I in which $R^1$ is hydroxy and $R^2$ is hydrogen.

The dehydration may be carried out using an acid such as sulphuric acid (eg. concentrated sulphuric acid), or p-toluene sulphonic acid. The reaction is conveniently carried out with heating, and conveniently an inert solvent is employed. For example, the reaction may be carried out using sulphuric acid at temperatures of about 70–130° C.; or using p-toluene sulphonic acid in a hydrocarbon solvent of, for example, toluene or xylene at ambient temperature to reflux, and preferably at reflux. The dehydration may also be carried out using trifluoroacetic acid in an inert solvent such as dichloromethane (at ambient temperature to reflux temperature).

(c) For compounds of formula I in which $R^1$ and $R^2$ are joined together so that $CR^1$–$CR^2$ is a double bond, treating a compound of formula II in which Z is a leaving group with a base.

Suitable values for Z include, for example, halogen such as chloro, bromo, iodo, or a methylsulphonyloxy or toluenesulphonyloxy group. Suitable bases include hydroxide (such as potassium or sodium hydroxide), and alkoxide (such as potassium t-butoxide or sodium ethoxide).

The reaction is conveniently carried out in the presence of a solvent, preferably a polar organic solvent. Suitable solvents include, for example, an alcohol (such as ethanol), or an aprotic solvent such as dimethylformamide or N-methylpyrrolidone. The reaction may be carried out at ambient temperature or at an elevated temperature, such as at a temperature between ambient and the reflux temperature of the reaction mixture. This method is generally preferred over that described in (b) when X is —$OCH_2$— or —$SCH_2$—.

The compounds of formula II may be prepared from a compound of formula I in which $R^1$ is hydroxy. For example, where Z is halogen the compound of formula I in which $R^1$ is hydroxy and $R^2$ is hydrogen may be reacted with the appropriate phosphorous halide (eg. $PCl_5$, $PBr_3$ or $PI_3$), or where Z is chloro, by reaction with thionyl chloride. The compound of formula I in which $R^1$ is hydroxy may be reacted with mesyl chloride to the compound in which Z is methylsulphonyloxy; and with tosyl chloride to give Z is toluene sulphonyloxy.

(d) For those compounds of formula I in which X is —$CH_2CO$—, reacting an organometallic compound of formula III in which M is a metal atom or a derivative thereof, with a compound of formula IV.

Suitable values for M include, for example, magnesium and lithium. In the case where M is magnesium it is conveniently present in the form of a derivative of formula —MgX where X is a halogen atom such as iodo or bromo, so that the organometallic compound of formula III is in the form known as a Grignard Reagent. The reaction is generally carried out in an inert solvent such as dry diethyl ether or tetrahydrofuran. For example, the reaction may be carried out at a temperature between 0° C. and the reflux temperature of the reaction mixture.

The compounds of formula III may be prepared from the corresponding compound of formula Ar-"hal" in which "hal" is a halogen atom, such as iodo or bromo as is well known in the art.

e) For those compounds of formula I in which X is —$CH_2$—NH— or —$NHCH_2$—, reducing a compound of formula I in which X is —CH=N— or —N=CH— (as appropriate).

The reaction may be carried out using a chemical reducing agent such as a hydride in a solvent such as an alcohol at ambient temperature. Thus, in a particular example, the reduction may be carried out using sodium borohydride in a solvent such as methanol at ambient temperature. The reduction may also be carried out by selective catalytic hydrogenation using similar conditions to those described under (a) above.

It will be appreciated that the preferred method of reduction will depend upon the value of X. Thus, for example, where debenzylation is possible (eg. when X is —NHCH$_2$—), it is generally preferred that a chemical reducing agent is employed.

The compounds of formula I in which X is —CH═N— may be prepared by reaction of a compound of formula V with a compound of formula VI. The reaction is generally carried out in an inert hydrocarbon solvent such as toluene or benzene, with heating (eg. at reflux) and the reaction may be accelerated by removing water generated in the reaction by azeotropic distillation. Similarly, the compounds of formula I in which X is —N═CH— may be prepared by reaction of a compound of formula VII with a compound of formula VIII.

f) For those compounds of formula I in which X is —CH$_2$NH—, —CH$_2$O—, —CH$_2$S—, R$^1$ is hydroxy and R$^2$ is hydrogen, reacting a compound of formula IX in which Z is —NH$_2$, —OH or SH as appropriate with a compound of formula X.

The reaction is conveniently carried out in a solvent such an inert hydrocarbon eg. toluene with heating. The reaction may be facilitated by the presence of acid or base.

The compound of formula X is conveniently generated in situ, by, for example, treating quinuclidin-3-one with trimethylsulphoxonium iodide in the presence of a base of, for example, an alkali metal hydride such as sodium hydride and in a solvent such as dimethylformamide, or an alkali metal hydroxide such as sodium hydroxide in a solvent such as an aqueous solvent.

The compound of formula X may also be prepared from a "halohydrin" as is well known in the art. The halohydrin may be prepared, for example, by addition of HOCl to the corresponding olefin and the halohydrin treated with base (eg. NaOH) to give the compound of formula X.

g) For compounds of formula I in which X is —CH═CH—, reacting a compound of formula XI with a compound of formula V in the presence of a base.

Suitable bases include alkoxides, such as potassium t-butoxide, and the reaction is conveniently carried out in an inert solvent such as tetrahydrofuran with cooling below ambient temperature eg −40° C. to 0° C.); and metal hydrides such as sodium hydride in a solvent such as dimethyl formamide or dimethyl suphoxide. A particularly suitable base is, for example, sodium dimsyl which may conveniently be used in a solvent such as dimethyl sulphoxide.

The compounds of formula XI may be prepared by reaction of a compound of formula ArCH$_2$-hal in which "hal" is halogen, such as chloro, with triphenylphosphine as is well known in the art.

h) For those compounds of formula I in which X is —CH$_2$CH$_2$—, reducing a compound of formula I in which X is —CH═CH— or in which X is —C≡C—.

The reaction may conveniently be carried out by catalytic hydrogenation using conditions similar to those mentioned in (a) above.

In an alternative synthesis a compound of formula ArCH$_2$CH$_2$-hal wherein "hal" represents a halogen atom such as bromo, is reacted with quinuclidin-3-one in the presence of sec-butyl lithium, with cooling (eg −70° C.) in an inert solvent such as tetrahydrofuran.

i) For compounds of formula I in which X is —COCH$_2$—, reacting a compound of formula XII in which M is a metal atom or a derivative thereof, with a compound of formula XIII.

Suitable values for M and suitable reaction conditions are those mentioned in (d) above. The compounds of formula III may be prepared from the corresponding halogeno compound in a manner analogous to the preparation of compounds of formula III discussed in (d) above.

j) For those compounds of formula I in which X is —CH$_2$O— or —CH$_2$S—, reacting a compound of formula XIV with a compound of formula XV, in which Z$^1$ is a leaving group and Z$^2$ is —YM, or Z$^1$ is —YM and Z$^2$ is a leaving group, and wherein Y is oxygen or sulphur (as appropriate) and h is a metal atom.

Suitable leaving groups include, for example, halogen (such as chloro, bromo or iodo), methanesulphonyloxy, toluenesulphonyloxy or trifluoromethanesulphonyloxy; and suitable metals include, for example sodium and lithium.

The process is generally performed in the presence of a suitable solvent, for example, a hydrocarbon, such as toluene or xylene, or an ether such as dioxan or tetrahydrofuran, and at a temperature in the range, for example 20–150° C.

It may be desirable to protect the quinuclidine nitrogen atom during the reaction, especially when Z$^1$ is —YM, as described in (1) below. It may be desirable to protect R$^1$ when it represents a hydroxy group as, for example, a silyl ether.

k) For those compounds of formula I in which X is —OCH$_2$— or —SCH$_2$— and R$^1$ and R$^2$ are both hydrogen, reacting a compound of formula XVI in which Y is oxygen or sulphur as appropriate with a compound of formula XVII in which Z is a leaving group.

Suitable leaving groups include halogen, such as chloro, bromo or iodo, methanesulphonyloxy and toluenesulphonyloxy. The reaction is generally carried out in the presence of a base such as an alkali metal hydroxide, eg sodium or potassium hydroxide, and in a solvent such as dimethyl sulphoxide or dimethylformamide.

l) For compounds of formula I in which X is —OCH$_2$—, —SCH$_2$—, —CH2O—, or —CH$_2$S—, deprotecting a compound of formula XVIII in which Q is a protecting group.

Suitable values for Q include, for example, —BH$_3$— or an oxygen atom. When Q is —BH$_3$ the deprotection may be carried out by treatment with an acid such as hydrochloric acid in acetone. When Q is an oxygen atom deprotection may be carried out by reduction using a suitable reducing agent such as sulphur dioxide.

The compounds of formula XVIII in which X is —CH$_2$O— or —CH$_2$S— may be prepared by methods analogous to those described in (j), and in which X is —OCH$_2$— or —SCH$_2$— by methods analogous to those described in (k) above, but in which the starting material containing the quinuclidine moiety is protected by Q. A preferred way of preparing compounds of formula XVIII in which X is —CH$_2$O— or —CH$_2$S— and R$^1$ is hydroxy and R is hydrogen is by a procedure analogous to that described in (f) in which the compound of formula X is protected by Q. The quinuclidine moiety in the various starting materials may be protected using methodology well known in the art. Thus, for example, those in which Q is BR$_3$ may be prepared by reaction of the appropriate quinuclidine moiety with BH$_3$.THF, generally with cooling (for example at −70° C.); whilst those in which Q is an oxygen atom may be prepared by oxidation of the appropriate quinuclidine moiety with, for example, 30% hydrogen peroxide.

m) For those compounds of formula I in which X is —C≡C—, reacting a compound of formula I in which X is —CH═CH— with a halogen, followed by treatment with a base.

A suitable halogen is bromine and the reaction is conveniently carried out in an inert solvent such as carbon tetrachloride. Suitable bases include, for example, potasium t-butoxide. This treatment is conveniently carried out in a solvent such as THF, with. heating (eg. at a temperature between ambient and about 70° C.).

n) For those compounds of formula I in which $R^1$ is hydroxy, $R^2$ is hydrogen and X is —C≡C—, reacting a compound of formula XIX in which H is a metal atom, with quinuclidin-3-one.

A suitable metal is lithium and suitable reaction conditions include those mentioned in (d) above.

o) For those compounds in which $R^1$ and $R^2$ are hydrogen and X is —C≡C—, reacting a compound of formula XIX in which M is a metal atom with a compound of formula XV in which Z is a leaving group.

Suitable values for Z include, for example, halogen (such as chloro, bromo or iodo), methanesulphonyloxy, toluenesulphonyloxy or trifluoromethanesulphonyloxy; suitable values for M include, for example, lithium; and suitable reaction conditions include those mentioned under (d) above.

p) For those compounds in which X is —C≡C— and $R^1$ is hydrogen or hydroxy and $R^2$ is hydrogen, reacting a compound of formula XX with a compound of formula IX in which Z is a leaving group in the presence of a catalyst.

Suitable catalysts include, for example, transition metal complexes such as palladium or nickel complexes. Particular catalysts are palladium (II) complexes, a specific example of which is $Pd(PPh_3)_2Cl_2$. Suitable values for Z include, for example, halogen (such as chloro, bromo or iodo), methanesulphonyloxy, toluenesulphonyloxy and trifluoromethanesulphonyloxy. The reaction is generally carried out in the presence of a base, for example, an amine such as triethylamine and in a solvent such as dimethylformamide with heating (for example at 60 to 100° C.). The reaction is preferably carried out in the prersence of copper (I)iodide. Compounds of formula XX may be prepared according to Scheme 1a and 2b.

q) For those compounds in which X is —C≡C— and $R^1$ is hydrogen or hydroxy and $R^2$ is hydrogen, reacting a compound of formula XXI with a compound of formula IX in which Z is a leaving group in the presence of a catalyst.

Suitable reaction conditions are those mentioned under (p) above. Compounds of formula XXI may be prepared according to Scheme 1b and 2a.

r) For those compounds in which X is —CH=CH—, reducing a compound of formula I in which X is —C≡C—.

The reaction may be carried out by catalytic hydrogenation using conditions similar to those mentioned in (a) above. A particularly suitable catalyst is, for example, Lindlars catalyst (Pd on $BaSO_4$ poisoned with quinoline). The reaction may also be carried out using a reducing agent such as trhose mentioned under (a) above or lithium aluminium hydride in a suitable solvent such as diethylether at ambient temperature or with cooling.

s) For those compounds of formula I in which X is —CH=CH—, reacting a compound of formula XXII in which L is a suitable ligand with a compound of formula IX in which Z is a leaving group in the presence of a catalyst.

Suitable values for L include, for example, (1-6C)alkyl with butyl being preferred. Suitable values for Z, suitable catalysts and reaction conditions include those mentioned under (p) above. A particularly suitable catalyst is, for example, tris(dibenzylidine acetone)palladium [0].

The compounds of formula I in which X is —$SCH_2$— may be be oxidised to these in which the sulphur atom bears an oxygen atom (that is to a "sulphoxide") using, for example an appropriate quantity of sodium periodate. Further oxidation to the compound in which the sulphur atom bears two oxygen atoms (that is a "sulphone") may be carried out using a peracid such as peracetic acid or hydrogen peroxide. The oxidation of sulphur compounds to the corresponding sulphoxides and sulphones is well known in the chemical art. Compounds of formula I in which X is —$CH_2S$— may be oxidised to the corresponding sulphoxides or sulphones in the same way.

In some cases oxidation of compounds of formula I to give a sulphone may be accompanied by some oxidation of the nitrogen atom in the quinuclidine ring to the N-oxide. In such cases the quinuclidine N-oxide moiety may be reduced back to a quinuclidine moiety without affecting the sulphone using reducing agents well known in the art, such as sulphur dioxide.

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will be appreciated that the substituents on Ar may be reacted, using standard chemical methodology, to produce further groups. Thus, for example, ester groups may be hydrolysed to acid groups which may be reduced to give a hydroxy group. The hydroxy group may then be reacted with further reagents to give further groups.

In general, it is preferred that the substituents on Ar are introduced before Ar is coupled to the quinuclidine moiety but in some instances it may be appropriate to introduce substituents or modifiy substituents after such coupling. The various substituted phenyl derivatives used as starting materials may, as indicated above, be prepared by methods well known in the art. As particular examples starting materials in which Ar bears an alkoxy group which may be further substitututed as defined above may be prepared by alkylation of the appropriate phenol. Thus a compound of formula Hal—Ar—OH may be reacted with a compound of formula R—hal in the presence of a base and a suitable solvent (Hal are suitable halogen atoms and R represents remainder of the substituent to be introduced, thus, for example R will be alkoxyalkyl when an alkoxyalkoxy substituent is desired. Specific examples illustrating the generation of alkoxy substituents further substituted by other groups are shown in Scheme 3. Compounds in which Ar bears an alkylthio group which may be further substituted may be prepared in an analogous manner. Compounds in which Ar bears an alkoxycarbonylalkyl group may be prepared by esterification of a compound bearing a carboxyalkyl group using the appropriate alcohol and standard conditions such as acid catalysis (eg. sulphuric acid). An alkynyl group (which may be further substituted as defined above) may be introduced, for example, by reaction of an appropriate compound of formula Ar—Z in which Z is a suitable leaving group with a compound of formula HC≡C—R in which R represents the remainder of the substituent in a similar manner to that described in (p) above. In a similar manner compounds with an alkenyl substiuent (which may be further substituted) may be prepared from a compound of formula Ar—Z and R—CH=CH$_2$. Compounds having an alkenyl substituent such as allyl and an oxy substituent may be prepared from a compound of formula ArOH by reaction with, for example, allyl bromide followed by a Claisen rearrangement as illustrated in Scheme 3.

Compounds in which Ar bears a (CH$_2$)nCO$_2$R group in which n is 1 or greater than 1 and R is, for example, alkyl may be prepared, for example, by a Wittig reacgtion on the corresponding compound of formula Ar(CH$_2$)mCOR$^{11}$ (m=n−1, R$^{11}$=H or alkyl) as illustrated in Scheme 4. The product may then be further modified using stand reaction conditons to provide further desired groups eg. hydrolysed to the acid. Compounds having a (CH$_2$)nCO$_2$R group may also be prepared from compounds of formula Ar(CH$_2$) mCHO (m=n−1) as illustrated in Scheme 4. The acids provided may then be further modified by, for example, reduction or esterification to provide further groups or groups which can be reacted further.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.

(a) Inhibition of Squalene synthase

In this test, the ability of a compound to prevent the formation of squalene from a radioactive substrate (tritiated farnesyl pyrophosphate) is assessed.

The test compound is incubated at a concentration of 25 micromolar in 200 μl of a buffered solution containing potassium phosphate (50 mM), MgCl$_2$ (4.95 mM), KF (9.9 mM), NADPH (0.9 mM) and rat liver microsomal protein (20 μg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 μM, and stopped after 15 minutes reaction time with the addition of 50 μl of 4% KOH. The reaction products are separated from unreacted substrate after application to a C-18 octadecyl 1 ccBond column (Analytichem Int product No. 617101). An aqueous fraction is eluted with 250 μl of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The IC$_{50}$ (concentration which results in a 50% inhibition of squalene production), of the test compound can be determined by testing the compound at several, for example five, concentrations predicted from the two concentration results. The IC$_{50}$ can then be determined from a plot of percentage inhibition against concentration of test compound.

In general, compounds of formula I show significant inhibition in the above test at a concentration in the range of about 0.001 to 25 μM.

By way of illustration of the squalene synthase inhibitory properties of the compound of formula I, described in Example 16 below gave an inhibition of about 80% at 2.5 μM.

(b) Acute rat cholesterol synthesis assay.

This is an acute in vivo test in the rat to measure de novo hepatic cholesterol synthesis from exogenously administered $^{14}$C-acetate.

Female rats (35–55 g) are housed in reverse lighting conditions (red light from 0200 h–1400 h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 μCi [2-$^{14}$C]-acetate (NEN DUPONT. specific activity, 45–60 mCi/mmol NEC-085H, or AHERSHAM specific activity, 50–60 mCi/mmol CFA 14) in a volume of 0.25 ml saline (100 μCi/ml). After a further hour, rats are terminally anaesthetised with halothane and a blood sample obtained from the abdominal vena cava.

1 ml of plasma is lyophilised and then saponified in 2 ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. ED$_{50}$ values can be determined in the standard way.

In general, compounds of formula I show activity in the range of about 0.1 to 100 mg/kg.

By way of illustration, the compound of formula I described in Example 16 gave an ED50 of about 5.1 mg/kg.

No overt toxicity was detected when compounds of the formula I were administered at several multiples of their minimum inhibitory dose or concentration.

An alternative test to measure the ability of a compound to inhibit cholesterol synthesis in vivo uses $^3$H-mevalonolactone in place of $^{14}$C-acetate.

As mentioned above, the compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthase in a warm-blooded animals (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

The invention will now be illustrated by the following non-limiting Examples in which, unless otherwise stated:

(i) evaporations were carried out by rotary evaporation in vacuo;

(ii) operations were carried out at room temperature, that is in the range 18–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessarily the maximum attainable by diligent process development;

(v) proton NMR spectra were normally determined at 200 MHz in DMSO-d6 (unless stated otherwise) using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) all end-products were characterised by microanalysis, NMR and/or mass spectroscopy (molecular ions denoted by m/z values); and (vii) conventional abbreviations are used for individual radicals and recrystallisation solvents, for example, Me=methyl, Et=ethyl, Pr=Propyl, Pr$^i$=isopropyl, Bu=butyl, Bu$^i$=isobutyl, Ph=phenyl; EtOAc=ethyl acetate, Et$_2$O=ether, MeCN=acetonitrile, MeOH=methanol, EtOH=ethanol, Pr$^i$OH=2-propanol, H$_2$O=water.

EXAMPLE 1

Bis(triphenylphosphine)-palladium (II) chloride (85 mg) and copper (I) iodide (43 mg) were added to a solution of ethyl 3-(3-allyl-4-trifluoromethylsulphonyloxyphenyl) propionate (920 mg) and 3-ethynyl-3-hydroxyquinuclidine (375 mg) in dimethyl formamide (5 ml) at ambient temperature under an atmosphere of argon. Triethylamine (2.5 ml) was added. The mixture was then stirred for 6 hours at 75° C.

The reaction mixture was cooled to ambient temperature. Water (50 ml) and 2M aqueous sodium carbonate solution (25 ml) were added to the mixture and the aqueous phase was extracted with ethyl acetate (3×25 ml). The organic phase was filtered. The filtrate was washed with 2M aqueous sodium carbonate solution (1×25 ml) and then with saturated brine solution (1×50 ml). The organic phase was dried (MgSO$_4$) and evaporated to give an oil which was purified by column chromatography on alumina (Alumina 507 C) using a 19:1 (v/v) mixture of ethyl acetate and methanol as eluent to give an oil. The oil was triturated with hexane to give 3-[2-{2-allyl-4-(2-ethoxycarbonylethyl)-phenyl}ethynyl]quinuclidin-3-ol as a solid (270 mg), m.p.

55–6° C.; microanalysis, found: C, 74.6; H, 8.1; N, 3.70%, $C_{23}H_{29}NO_3.0.1 H_2O$ requires: C, 74.8; H, 8.0; N, 3.80%; NMR (CDCl$_3$): 1.22 (3H, t), 1.35–1.50 (1H, m), 1.58–1.80 (1H, m), 1.90–2.13 (3H, m), 2.38–2.57 (1H, m), 2.58 (2H, t), 2.72–2.95 (6H, m), 3.05 (1H, d), 3.30 (1H, d of d), 3.49 (2H, d), 4.12 (2H, q), 4.98–5.10 (2H, m), 5.85–6.03 (1H, m), 6.98–7.07 (2H, m) and 7.33 (1H, d); m/z 368 (M+H).

The ethyl 3-(3-allyl 4-trifluoromethylsulphonyloxyphenyl)propionate used as starting material was obtained as follows.

Allyl bromide (2.30 g) was added to a stirred suspension of ethyl 3-(4-hydroxyphenyl)propionate (3.49 g) and anhydrous potassium carbonate (2.76 g) in butan-2-one (30 ml). The reaction mixture was heated at reflux for 18 hours. The reaction mixture was allowed to cool to ambient temperature and the mixture was filtered. The filtrate was evaporated to give an oil which was purified by column chromatography on silica gel (Merck.Art. No. 9385) using a 4:1 (v/v) mixture of n-hexane and ethyl acetate as eluent to give ethyl 3-(4-allyloxyphenyl)propionate (4.09 g) as a colourless oil; NMR (CDCl$_3$): 1.22 (3H, t), 2.48 (2H, t), 2.88 (2H, t), 4.13 (2H, q), 4.51 (2H, m), 5.25–5.42 (2H, m), 5.95–6.15 (1H, m), 6.83 (2H, d) and 7.03 (2H, d); m/z 235 (M+H).

A solution of ethyl 3-(4-allyloxyphenyl)propionate (3 g) in diphenyl ether (24 ml) was heated at reflux for 12 minutes. The reaction mixture was allowed to cool to ambient temperature and the reaction mixture was filtered through a silica gel pad. Elution with a 4:1 (v/v) mixture of hexane and ethyl acetate gave slightly impure product. Further purification by medium pressure column chromatography on silica gel (Merck Art. No. 9385) using a 9:1 (v/v) mixture of n-hexane and ethyl acetate as eluent gave ethyl (3-allyl-4-hydroxyphenyl)propionate (2.86 g) as a yellow oil; microanalysis, found: C, 71.4; H, 7.5%; $C_{14}H_{18}O_3$ requires: C, 71.8; H, 7.74%; NMR (CDCl$_3$): 1.21 (3H, t), 2.58 (2H, m), 2.86 (2H, t), 3.37 (2H, d), 4.12 (2H, q), 5.02 (1H, s), 5.07–5.20 (2H, m), 5.90–6.10 (1H, m), 6.67–6.74 (1H, m), 6.90–6.98 (2H, m); m/z 234 (M).

Trifluoromethyl sulphonic anhydride (0.93 ml) was added dropwise over 5 minutes to a stirred solution of ethyl 3[(3-allyl 4-hydroxy)phenyl]propionate (1.17 g) in pyridine (5 ml) at 0° C. under an atmosphere of argon. The mixture was stirred at 0° C. for 16 hours and then added to ice (50 g). The aqueous mixture was extracted with ether (3×30 ml). The ether extracts were combined, washed with water (1×25 ml), 1M aqueous hydrochloric acid (3×25 ml) and saturated brine (2×25 ml). The organic phase was dried (MgSO$_4$) and evaporated to give ethyl 3-(3-allyl-4-trifluoromethylsulphonyloxyphenyl)propionate (1.72 g) as an oil; NMR (CDCl$_3$): 1.22 (3H, t), 2.61 (2H, t), 2.95 (2H, t), 3.45 (2H, d), 4.12 (2H, q), 5.06–5.20 (2H, m), 5.83–5.90 (1H, m) and 7.05–7.20 (3H, m); m/z 367 (M+H).

The 3-ethynyl-3-hydroxyquinuclidine used as starting material was obtained as follows:

A solution of n-butyl lithium (100 ml of a 2M solution in pentane) was added portion-vise over a period of 20 minutes to a stirred solution of ethynyltrimethylsilane (19.6 g) in dry tetrahydrofuran (400 ml) at −70° C. The mixture was stirred for 1 hour at −70° C. A solution of 3-quinuclidinone (2.4 g) in dry tetrahydrofuran (100 ml) was then added to the mixture and the mixture stirred for 1 hour at −70° C. Methanol (1 ml) was then added to the mixture and the mixture allowed to warm to room temperature. The solvents were removed by evaporation. Methanol (500 ml) and potassium carbonate (40 g) were added to the residue and the mixture was stirred for 1 hour. The solvent was removed by evaporation. The residue was triturated with water (500 ml) and then dried in vacuo to give 3-ethynyl-3-hydroxyquinuclidine as a solid, m.p. 193–197° C.; NMR (DMSO-d$_6$): 1.5–1.3(1H, m), 1.4–1.6(1H, m), 1.7–1.95(3H, m), 2.55–2.8(5H, m), 2.95(1H, d), 3.3(1H, d) and 5.4(1H, s); m/z 152 (M+H).

EXAMPLE 2

Using the method described in Example 1, but with ethyl 3-(3-allyl-4-trifluoromethylsulphonyloxyphenyl)acetate in place of ethyl 3-(3-allyl-4-trifluoromethylsulphonyloxyphenyl)propionate, there was thus obtained 3-[2-(2-allyl-4-ethoxycarbonylmethylphenyl) ethynyl]quinuclidin-3-ol as a solid, mp 84–6° C.; microanalysis, found: C, 72.8; H, 7.60; N, 3.40%; $C_{22}H_{27}NO_3$ 0.5 $H_2O$ requires C, 72.9; H, 7.60; N, 3.80%; NMR (CDCl$_3$) 1.25 (3H, t), 1.38–1.55 (1H, m), 1.60–1.78 (1H, m), 1.90–2.18 (3H, m), 2.20–2.50 (1H, m), 2.73–3.00 (4H, m), 3.08 (1H, d), 3.35 (1H, d), 3.51 (2H, d), 3.58 (2H, s), 4.14 (2H, q), 5.0–5.10 (2H, m), 5.85–6.05 (1H, m), 7.07 (2H, m) and 7.35 (1H, d); m/z 354 (M+H).

The ethyl 3-(3-allyl 4-trifluromethylsulphonyloxyphenyl) acetate used as starting material was prepared from ethyl (2-allyl-4-hydroxyphenyl)acetate using the method described in Example 1 for the preparation of ethyl-3-[(3-allyl-4-hydroxy)phenyl]-propionate. There was thus obtained ethyl-3-(3-allyl-4-trifluoromethylsulphonyloxyphenyl)acetate as an oil; NMR (CDCl$_3$): 1.25 (3H, t), 3.45 (2H, d), 3.61 (2H, s), 4.15 (2H, q), 5.08–5.18 (2H, m), 5.82–5.97 (1H, m) and 7.25 (3H, m); m/z 353 (M+H).

The ethyl (3-allyl-4-hydroxyphenyl)acetate was obtained using the method in Rec. Trav. Pays Bas, 1952, 71, 879).

EXAMPLE 3

Using the method described in Example 1, but with ethyl (3-allyl-4-trifluoromethylsulphonyloxyphenyl)oxyacetate in place of ethyl 3-(3-allyl-4-trifluoromethylsulphonyloxyphenyl)propionate, there was thus obtained 3-[2-(2-allyl-4-ethoxycarbonylmethyloxyphenyl)-ethynyl]quinuclidin-3-ol as a solid, mp 98–99° C.; microanalysis, found: C, 69.9; H, 7.30; N, 3.80%; $C_{22}H_{27}NO_4$ 0.5 $H_2O$ requires C, 70.0; H, 7.40; N, 3.70%; NMR (CDCl$_3$): 1.30 (3H, t), 1.35–1.52 (1H, m), 1.60–1.75 (1H, m), 1.92–2.15 (3H, m), 2.15–2.45 (1H, m), 2.70–2.95 (4H, m), 3.07 (1H, d), 3.32 (1H, d of d), 3.51 (2H, d), 4.26 (2H, q), 4.60 (2H, s), 5.0–5.12 (2H, m), 5.86–6.02 (1H, m), 6.65–6.75 (2H, m) and 7.35 (1H, d); m/z 370 (M+H).

The ethyl (3-allyl-4-trifluoromethylsulphonyloxyphenyl) oxyacetate used as starting material, was prepared as follows.

Allyl bromide (3.37 g) was added to a stirred suspension of ethyl 4-hydroxyphenoxyacetate (5.14 g) [prepared by method of Moser, J.A.C.S., (1950), 72, 1413) and potassium carbonate (3.90 g) in butan-2-one (50 ml). The reaction mixture was heated at reflux for 12 hours. The reaction mixture was cooled to ambient temperature and then filtered. The filtrate was evaporated to give an oil which was purified by column chromatography on silica gel (Merck. Art. No. 7734) using a 4:1 (v/v) mixture of hexane and ethylacetate as eluent to give ethyl 4-allyloxyphenoxyacetate (6.41 g) as a colourless oil; microanalysis, found: C, 65.8; H, 7.20%; $C_{13}H_{16}O_4$ requires C, 66.1; H, 6.83%; NMR (CDCl$_3$): 1.28 (3H, t), 4.25 (2H, q), 4.48 (2H, m), 4.57 (2H, s), 5.22–5.44 (2H, m), 5.92–6.12 (1H, m) and 6.84 (4H, s).

A solution of ethyl 4-allyloxyphenoxyacetate (2.0 g) in diphenylether (15 ml) was heated at reflux for 12 minutes. The reaction mixture was allowed to cool to ambient temperature and the reaction mixture was poured onto a silica gel pad (Merck Art. No. 9385). Elution with hexane followed by a 4:1 (v/v) mixture of hexane and ethyl acetate gave ethyl 3-allyl-4-hydroxyphenoxyacetate (1.62 g) as a solid, mp 52.8° C.; microanalysis, found: C, 66.3; H, 7.20%; $C_{13}H_{16}O_4$ requires: C, 66:1; H, 6.83%; NMR ($CDCl_3$): 1.28 (3H, t), 3.35 (2H, d), 4.25 (2H, q), 4.55 (2H, s), 4.73 (1H, s), 5.07–5.20 (2H, m), 5.88–6.10 (1H, m) and 6.62–6.78 (3H, m); m/z 237 (M+H).

The method described in Example 1 for the preparation of ethyl 3-(3-allyl-4-trifluoromethylsulphonyloxyphenyl) propionate was used to convert ethyl 3-allyl-4-hydroxyphenoxyacetate to ethyl (3-allyl-4-trifluoromethylsulphonyloxyphenyl)oxyacetate as a colourless oil, NMR ($CDCl_3$) 1.27 (3H, t), 3.42 (2H, d), 4.25 (2H, q), 4.60 (2H, s), 5.07–5.20 (2H, m), 5.80–5.97 (1H, m), 6.72–6.85 (2H, m) and 7.15 (1H, d); m/z 368 (M).

EXAMPLE 4

A mixture of ethyl 2-allyl-4-bromophenoxyacetate (912 mg), 3-ethynyl-3-hydroxyquinuclidine (453 mg), bis(triphenylphosphine)-palladium (II) chloride (106 mg), copper (I) iodide (53 mg), triethylamine (3 ml) and dimethylformamide (6 ml) was stirred at 80° C. under an atmosphere of argon for 8 hours. The reaction mixture was cooled to ambient temperature and water (100 ml) was added. The mixture was extracted with ethyl acetate (3×50 ml). The ethyl acetate extracts were combined and filtered. The filtrate was washed with saturated brine solution (3×50 ml), dried ($MgSO_4$) and evaporated. The residue was purified by column chromatography on Alumina (Fluka 507C) using ethyl acetate containing 2.5% methanol as eluent to give 3-[2-(3-allyl-4-ethoxycarbonylmethyloxyphenyl)ethynyl] quinuclidin-3-ol (220 mg) as a solid, mp 95.9° C.; microanalysis, found: C, 70.7; H, 7.30; N, 3.50%; $C_{22}H_{27}NO_4.0.25\ H_2O$ requires: C, 70.6; H, 7.35; H, 3.72%; NMR ($CDCl_3$): 1.28 (3H, t), 1.34–1.47 (1H, m), 1.52–1.72 (1H, m), 1.90–2.25 (3H, m), 2.25–2.60 (1H, m), 2.62–2.92 (4H, m), 2.97–3.09 (IH, d), 3.25–3.35 (1H, d of d), 3.42 (2H, d), 4.26 (2H, q), 4.62 (2H, s), 5.02–5.15 (2H, m), 5.88–6.08 (1H, m), 6.60–6.68 (1H, m) and 7.17–7.27 (2H, m); m/z 370 (M+H).

The ethyl 2-allyl-4-bromophenoxyacetate was prepared as follows.

Ethyl bromoacetate (1.68 g) was added to a stirred suspension of 2-allyl-4-bromophenol (2.13 g) and potassium carbonate (1.50 g) in butan-2-one (15 ml). The mixture was heated at reflux for 16 hours. The reaction mixture was cooled to ambient temperature and filtered. Water (100 ml) was added to the filtrate and the aqueous phase was extracted with ethyl acetate (3×50 ml). The ethyl acetate extracts were combined, washed with brine (2×25 ml), dried ($MgSO_4$) and evaporated to give a solid which crystallised from hexane to give ethyl 2-allyl-4-bromophenoxyacetate (2.10 g), mp 70.5° C.; microanalysis, found: C, 52.0; H, 5.10%; $C_{13}H_{15}BrO_3$ requires: C, 52.2; H, 5.05%; NMR ($CDCl_3$) 1.29 (3H, t), 3.42 (2H, d), 4.25 (2H, q), 4.58 (2H, s), 5.07–5.17 (2H, m), 5.88–6.18 (1H, m), 6.60 (1H, d) and 7.20–7.27 (2H, m); m/z 300 (M+H).

The 2-allyl-4-bromophenol was prepared by the method of Claisen and Eisleb, Annalen, 401, 1913, 38.

EXAMPLE 5

Using the method described in Example 4, but with ethyl 4-bromophenoxyacetate in place of ethyl 2-allyl-4-bromophenoxyacetate, there was thus obtained 3-[2-(4-ethoxycarbonylmethyloxyphenyl)ethynyl]quinuclidin-3-ol as a solid, mp 137.1° C.; microanalysis, found: C, 69.6; H, 7.40; N, 4.1%; $C_{19}H_{23}NO_4$ requires: C, 69.3; H, 7.04; N, 4.25%; NMR ($CDCl_3$): 1.27 (3H, t), 1.33–1.52 (1H, m), 1.54–1.77 (1H, m), 1.90–2.18 (3H, m), 2.20–2.70 (1H, m), 2.72–2.97 (4H, m), 3.03 (1H, d), 3.31 (1H, d of d), 4.21 (2H, q), 4.60 (2H, s), 6.78–6.88 (2H, d) and 7.30–7.40 (2H, d); m/z 330 (M+H).

The starting ethyl 4-bromophenoxyacetate was prepared by the method of Adams and Powell, J.A.C.S. 42, 1920, 656.

EXAMPLE 6

Using the method described in Example 4, but with ethyl 4-bromophenyl acetate in place of ethyl-2-allyl-4-bromophenoxyacetate, there was thus obtained 3-[2-(4-ethoxycarbonylmethylphenyl)ethynyl]quinuclidin-3-ol as a solid, mp 132.5° C.; microanalysis: C, 72.6; H, 7.60; N, 4.30%; $C_{19}H_{23}NO_3$ requires: C 72.8; H 7.40; N, 4.47%; NMR ($[CD_3]_2SO$): 1.18 (3H, t), 1.30 (1H, m), 1.59 (1H, m), 1.75–2.00 (3H, m), 2.67 (4H, t), 2.81 (1H, d), 3.07 (1H, d), 3.68 (2H, s), 4.08 (2H, q), 5.55 (1H, s) and 7.20–7.40 (4H, q); m/z 314 (M+H).

EXAMPLE 7

A mixture of 4-(2-methoxyethoxy)-iodobenzene (13.9 g), 3-ethynyl-3-hydroxyquinuclidine (7.55 g), bis(triphenylphosphine)palladium (II) chloride (1.75 g), copper (I) iodide (875 mg), triethylamine (25 ml) and dimethylformamide (50 ml) was stirred under an atmosphere of argon when an initial exothermic reaction ensued, the reaction temperature rising to 50° C. The reaction mixture was then stirred at ambient temperature for a further 16 hours. The triethylamine and dimethylformamide were removed by evaporation. The residue was dissolved in dichloromethane (500 ml) and washed with a 2M aqueous sodium hydroxide solution (2×50 ml), water (50 ml), dried ($MgSO_4$) and evaporated. The residue was purified by flash column chromatography on silica gel (Merck Art. No. 9385) using a gradient of 5% methanol in dichloromethane containing 1% 0.880 ammonia to 10% methanol in dichloromethane containing 1% 0.880 ammonia as eluent to give a solid (15 g). This solid was further purified by crystallisation from acetonitrile to give 3-[2-{4-(2-methoxyethoxy)phenyl}ethynyl] quinuclidin-3-ol (7.2 g) as a solid mp 148°–149° C.; microanalysis; found C 71.9; H 7.9; N 4.6%; $C_{18}H_{23}NO_3$ requires: C 71.7; H 7.69; N 4.65%; NMR ($[CD_3]_2SO$): 1.2–1.35 (1H, m), 1.5–1.65 (1H, m), 1.78–1.97 (3H, m), 2.6–2.73 (4H, m), 2.75–2.85 (1H, d), 2.99–3.09 (1H, d), 3.3 (3H, s), 3.6–3.68 (2H, m), 4.05–4.13 (2H, m), 5.46 (1H, br), 6.88–6.95 (2H, d) and 7.28–7.35 (2H, d); m/z 302 (M+H).

The 4-(2-methoxyethoxy)iodobenzene used as starting material was obtained as follows.

A mixture of 4-iodophenol (20 g), 2-bromoethylmethyl ether (11.4 g), potassium carbonate (12.5 g) and dimethylformamide (100 ml) was stirred at 80° C. for 4 hours. A further portion of 2-bromoethylmethyl ether (2.24 g) and potassium carbonate (2.5 g) was then added and the mixture stirred at 80° C. for a further 1 hour. The dimethylformamide was removed by evaporation. The residue was treated with a 2M aqueous sodium hydroxide solution (50 ml) and the mixture extracted with diethyl ether (3×50 ml). The ethereal extracts were combined, washed with 2M aqueous sodium hydroxide solution (2×20 ml), brine (20 ml), dried ($MgSO_4$) and evaporated to give 4-(2-methoxyethoxy)iodobenzene (23 g) as a white solid, m.p. 36–37° C. NMR ($[CD_3]_2SO$):

3.3 (3H, s), 3.6–3.7 (2H, m), 4.0–4.1 (2H, m), 6.72–6.82 (2H, d) and 7.52–7.62 (2H, d).

EXAMPLE 8

A 1M solution of lithium aluminium hydride in tetrahydrofuran (10 ml) was added over a period of 20 minutes to a stirred solution of 3-[2-{4-(2-methoxyethoxy)phenyl}ethynyl]quinuclidin-3-ol (3.01 g) in dry tetrahydrofuran (100 ml) under an atmosphere of argon at 40° C. The reaction mixture was then stirred at ambient temperature for 16 hours. Water (0.4 ml) and 2M aqueous sodium hydroxide solution (0.8 ml) was then added to the reaction mixture dropwise followed by a further quantity of water (1.2 ml). The resulting precipitate was collected by filtration and the filtrate was evaporated. The residue from the filtrate was crystallised from acetonitrile to give 3-[(E)-2-{4-(2-methoxyethoxy)phenyl}vinyl]quinuclidin-3-ol (2.54 g) as a solid, mp 164–166° C., microanalysis, found C,71.4; H,8.6; N,4.5%; $C_{18}H_{25}NO_3$ requires: C,71.3; H,8.31; N,4.62%; NMR ($[CD_3]_2SO$): 1.15–1.32 (1H, m), 1.38–1.52 (1H, m), 1.62–1.74 (2H, m), 1.95–2.1 (1H, m), 2.58–2.6 (5H, m), 2.82–2.92 (1H, d), 3.3 (3H, s), 3.6–3.67 (2H, m), 4.03–4.1 (2H, m), 4.66 (1H, s), 6.38–6.45 (1H, d, J=16.67), 6.51–6.58 (1H, d, J=16.67), 6.86–7.12 (2H, d) and 7.32–7.38 (2H, d); m/z 304 (M+H).

EXAMPLE 9

A mixture of 3-[2-{4-(2-methoxyethoxy)phenyl}ethynyl]-quinuclidin-3-ol (1.8 g) in ethanol (200 ml) and a catalyst of 10% (v/v) palladium on carbon (100 mg) was stirred under an atmosphere of hydrogen until hydrogen uptake ceased. The palladium/carbon catalyst was removed by filtration and the filtrate was evaporated. The residue was crystallised from a 3:1 (v/v) mixture of cyclohexane ethylacetate to give 3-[2-{4-(2-methoxyethoxy)phenyl}ethyl]quinuclidin-3-ol (700 mg) as a solid, mpt 116–117° C. Microanalysis, found C,71.1; H,9.2; N,4.5%; $C_{18}H_{27}NO_3$ requires: C,70.8; H,8.9; N,4.59%; NMR ($[CD_3]_2SO$): 1.15–1.35 (1H, m), 1.4–1.6 (1H, m), 1.65–1.78 (2H, m), 1.9–2.08 (1H, m), 2.45–2.8 (10H, m), 3.3 (3H, s), 3.6–3.68 (2H, m), 4.0–4.08 (2H, m), 4.3 (1H, br), 6.78–6.86 (2H, d), 7.05–7.13 (2H, d); m/z 306 (M+H).

EXAMPLE 10

Bis(triphenylphosphine)-palladium (II) chloride (95 mg) was added to a stirred mixture of 3-ethynyl-3-hydroxyquinuclidine (400 mg), 1-(4-bromo-2,6-dimethylphenoxy)-2-methoxyethane (704 mg) and copper (I) iodide (48 mg) in dimethylformamide (DMF) (5.5 ml) and triethylamine (2.7 ml) at ambient temperature and under an atmosphere of argon. The mixture was heated at 65° C. for 14 hours, cooled to ambient temperature, diluted with 2M aqueous sodium hydroxide (20 ml) and extracted with diethyl ether (5×100 ml). The ethereal extracts were combined, washed with water (100 ml) and saturated brine (100 ml), dried ($K_2CO_3$) and evaporated. The residue was crystallised from acetonitrile to give 3-[2-(4-{2-methoxyethoxy}-3,5-dimethylphenyl)ethynyl]quinuclidin-3-ol (130 mg) as a solid, m.p. 120° C.; microanaylsis, found: C, 72.4; H, 8.2; N, 4.1%; $C_2OH_{27}NO_3$ requires: C, 72.9; H, 8.3; N, 4.2%; NMR($[CD_3]_2SO$): 1.3 (1H,m), 1.57(1H,m), 1.9(3H,m), 2.21(6H,s), 2.65(4H,m), 2.8(1H,d), 3.02(1H,d), 3.31(3H,s), 3.61(2H,m), 3.87(2H,m), 5.5(1H,br) and 7.07(2H,s); m/z 330 (M+H).

The 1-(4-bromo-2,6-dimethylphenoxy)-2-methoxyethane used as starting material was obtained as follows.

Lithium hydride (200 mg) was added to a stirred solution of 4-bromo-2,6-dimethylphenol (65 g) in DMF at ambient temperature. When evolution of hydrogen had ceased, ethylene carbonate (31.9 g) was added and the mixture was heated at 150° C. for 12 hours. The DMF was removed by evaporation and the cooled residue was dissolved in ethyl acetate (500 ml). The ethyl acetate solution was washed with water (2×100 ml) and then with saturated brine (100 ml), dried ($MgSO_4$) and evaporated. The residue was crystallised from methanol to give 2-(4-bromo-2,6-dimethylphenoxy)ethanol (51 g), m.p. 47–48° C. NMR ($CDCl_3$): 2.21(6H,s), 3.86(2H,m), 3.93(2H,m), 7.12(2H,s).

A solution of 2-(4-bromo-2,6-dimethylphenoxy)ethanol (15 g) in methylene chloride (100 ml) was added to a stirred solution of sodium hydroxide (50 g) in water (50 ml) at 5° C. Dimethyl sulphate (8.6 ml) was added dropwise to the stirred solution at 5° C. over 30 minutes. The mixture was stirred at ambient temperature for 12 hours. Dimethylsulphate (5 ml) was added at ambient temperature and the mixture stirred for a further 2 hours. The mixture was cooled to 0° C. and a solution of ammonia (10 ml, density=0.88 g/cm$^3$) was added. The mixture was stirred for 20 minutes, diluted with iced water (500 ml). The methylene chloride phase was removed and the aqueous phase extracted with methylene chloride (2×150 ml). The organic extracts were combined, washed with water (2×100 ml), saturated brine (100 ml) and evaporated. The residue was distilled using a short path distillation apparatus (furnace temperature 120° C./0.08 bar) to give 1-(4-bromo-2,6-dimethylphenoxy)-2-methoxyethane (11.6 g); NMR($CDCl_3$): 2.34(6H,s), 3.52 (3H,s), 3.78(2H,m), 3.96(2H,m) and 7.2(2H,s).

EXAMPLE 11

Using the procedure described in Example 10, but using 1-(4-bromobenzyloxy)-2-methoxyethane in place of 1-(4-bromo-2,6-dimethylphenoxy)-2-methoxyethane, there was thus obtained 3-[2-(4-{2-methoxyethoxymethyl}phenyl)ethynyl]quinuclidin-3-ol (14%) as a solid, m.p. 127–128° C.; microanalysis, found: C, 71.9; H, 7.8; N, 4.4%; $C_{19}H_{25}NO_3$ requires: C, 72.4; H, 8.0; N, 4.4%; NMR ($[CD_3]_2SO$): 1.30(1H,m), 1.61(1H,m), 1.95(3H,m), 2.69 (4H,t), 2.83(1H,d), 3.07(1H,d), 3.25(3H,s), 3.49(2H,m), 3.56(2H,m), 4.50(2H,s), 5.58(1H,br), 7.30(2H,d) and 7.39 (2H,d); m/z 316 (M+H).

The 1-(4-bromobenzyloxy)-2-methoxyethane used as starting material was obtained as follows.

2-Methoxyethanol (5.0 g) was added to a stirred suspension of sodium hydride (2.64 g of a 60% mineral oil suspension) in DMF (200 ml) at ambient temperature and under an atmosphere of argon. The stirred mixture was heated to 60° C. and then cooled to 5° C. Solid 4-bromobenzyl bromide (15 g) was added in one portion. The mixture was stirred for 12 hours at ambient temperature, then for 1 hour at 60° C. and cooled. The mixture was diluted with iced water (600 ml) and extracted with ethyl acetate (3×200 ml). The ethyl acetate extracts were combined, washed with 2M aqueous hydrochloric acid (100 ml), water (2×100 ml), saturated brine (100 ml), dried ($MgSO_4$) and evaporated. The residue, an oil, was distilled using a short path distillation apparatus (furnace temperature 125° C./0.05 bar) to give 1-(4-bromobenzyloxy)-2-methoxyethane (9.8 g); NMR ($CDCl_3$): 3.39(3H,s), 3.51(4H,m), 4.51(2H,s), 7.21(2H,d) and 7.44(2H,d).

EXAMPLE 12

Using a similar procedure to that described in Example 10, but using 1-(4-bromophenoxy)-2-methoxy-1- methoxymethylethane as starting material in place of 1-(4-bromo-2,6-dimethylphenoxy)-2-methoxyethane, there was obtained 3-[2-(4-{2-methoxy-1-methoxymethylethoxy}phenyl)ethynyl]quinuclidin-3-ol (33% yield) as a solid, m.p. 125–127° C. (after recrystallisation from acetonitrile); microanalysis, found C, 69.6; H, 8.0, N, 4.0%; $C_{20}H_{27}NO_4$ requires: C, 69.5; H, 7.9; N, 4.1%; NMR([$CD_3$]$_2$SO): 1.2–1.4(1H,m), 1.5–1.65(1H,m), 1.7–2.0 (3H,m), 2.6–2.75(4H,t), 2.75–2.9(1H,d), 3.0–3.1(1H,d), 3.25(6H,s), 3.5–3.6(4H,d), 4.55–4.7(1H,m), 5.5(1H,s), 6.9–7.0(2H, and 7.25–7.35(2H,d); m/z 346(M+H).

The 1-(4-bromophenoxy)-2-methoxy-1-methoxymethylethane used as a starting material was obtained using a similar procedure to that described for the preparation of the starting material in Example 14, but starting from 4-bromophenol and 1,3-dimethoxypropan-2-ol (obtained as described in JACS 1939, 61, 433). There was thus obtained 1-(4-bromophenoxy)-2-methoxy-1-methoxymethylethane; NMR(CDCl$_3$): 3.4(6H,s), 3.6(4H,s), 4.4–4.5(1H,m), 6.8–6.9(2H,d) and 7.3–7.4(2H,d).

EXAMPLE 13

Using a similar procedure to that described in Example 10, but using 1-(4-bromo-2,6-dimethylphenoxy)-2-ethoxyethane as starting material in place of 1-(4-bromo-2,6-dimethylphenoxy)-2-methoxyethane, there was obtained 3-[2-(4-{2-ethoxyethoxy}-3,5-dimethylphenyl)ethynyl] quinuclidin-3-ol (36% yield) as a solid, m.p. 113–115° C. (after recrystallisation from acetonitrile); microanalysis, found C, 73.1; H, 8.6, N, 4.4%; $C_{21}H_{29}NO_3$ requires: C,73.4; H, 8.5; N, 4.1% NMR(CDCl$_3$) 1.2–1.3(3H,t), 1.3–1.5(1H,m), 1.5–1.7(1H,m), 1.9–2.2(3H,m), 2.25(6H,s), 2.75–2.95(4H,t), 2.95–3.05(1H,d), 3.2–3.4(1H,d of d), 3.5–3.7(2H,q), 3.7–3.8(2H,q), 3.9–4.0(2H,q) and 7.1(2H,s); m/z 344(M+H).

The 1-(4-bromo-2,6-dimethylphenoxy)-2-ethoxyethane used as starting material was obtained in an analogous manner to that for the preparation of 1-(4-bromo-2,6-dimethylphenoxy-2-methoxy ethane in Example 10 but using diethylsulphate as the alkylating reagent. There was thus obtained 1-(4-bromo-2,6-dimethylphenoxy)-2-ethoxyethane, NMR(CDCl$_3$): 1.2–1.3(3H,t), 2.25(6H,s), 3.55–3.65(2H,q), 3.7–3.8(2H of d), 3.85–3.95(2H,d of d) and 7.15(2H,s).

EXAMPLE 14

Using a similar procedure to that described in Example 10, but using 1-(4-bromo-2,6-dimethylphenoxy)-2-phenoxyethanol as starting material in place of 1-(4-bromo-2,6-dimethylphenoxy)-2-methoxyethane and extracting the aqueous mixture obtained after diluting the reaction mixture with 2M aqueous sodium hydroxide with dichloromethane instead of diethyl ether, there was obtained 3-[2-(4-{2-phenoxyethoxy}-3,5-dimethylphenyl)ethynyl]quinuclidine-3-ol (28% yield) as a solid, m.p. 141–142° C. (after recrystallisation from acetonitrile); microanalysis, found: C, 76.2; H, 7.4; N, 3.5%; $C_{25}H_{29}NO_3$ requires: C, 76.7, H, 7.5; N, 3.6%; in 28% yield NMR ([$CD_3$]$_2$O): 1.2–1.4(1H,m), 1.5–1.65(1H,m), 1.7–2.0(3H,m), 2.15–2.3(6H,s), 2.6–2.75 (4H,t), 2.75–2.9(1H,d), 2.95–3.1(1H,d), 4.0–4.3(4H,m), 5.5 (1H,s), 6.9–7.05(3H,m), 7.1(2H,s) and 7.25–7.4(2H,m); m/z 392 (M+H).

The 1-(4-bromo-2,6-dimethylphenoxy)-2-phenoxyethane used as a starting material was obtained as follows.

A solution of diethyl azodicarboxylate (3.5 g) in tetrahydrofuran (5 ml) was added portionvise over a period of 30 minutes to a stirred solution of triphenylphosphine (5.2 g), phenol (1.88 g) and 2-(4-bromo-2,6-dimethylphenoxy) ethanol in dry tetrahydrofuran (30 ml) under an atmosphere of argon at 0° C. The resultant mixture was allowed to attain ambient temperature and stirred for a further 18 hours. The tetrahydrofuran was removed by evaporation and the residue was purified by flash column chromatography on silica gel (Merck Art No. 9385) using 5% ethyl acetate/hexane as eluent to give 1-(4-bromo-2,6-dimethylphenoxy)2-phenoxyethane (1.07 g) as a solid, m.p. 49–50° C. (after recrystallisation from hexane).

EXAMPLE 15

Using a similar procedure to that described in Example 10, but using 1-(4-bromophenoxy)-2-phenoxyethane as starting material in place of 1-(4-bromo-2,6-dimethylphenoxy)-2-methoxyethane and extracting the aqueous mixture obtained after diluting the reaction mixture with 2M aqueous sodium hydroxide with dichloromethane instead of diethyl ether, there was obtained 3-[2-(4-{2-phenoxyethoxy}phenyl)ethynyl]quinuclidin-3-ol (18% yield) as a solid, m.p. 207–208° C. (after recrystallisation from acetonitrile); microanalysis, found: C,74.7; H, 6.9; N, 3.8% $C_{23}H_{24}NO_3$. 0.3$H_2O$ requires: C, 74.9; H, 7.0; N, 3.8%; NMR ([$CD_3$]$_2$SO): 1.2–1.4(1H,m), 1.5–1.65(1H,m), 1.7–2.0(3H,m), 2.55–2.75(4H,t), 2.75–2.9(1H,d), 3.0–3.15 (1H,d), 4.2–4.4(4H,m), 5.5(1H,s), 6.9–7.05(5H,m) and 7.2–7.4(4H,m); m/z 364 (M+H).

The 1-(4-bromophenoxy)-2-phenoxyethane (m.p. 101–102° C.) used as a starting material was obtained in a similar manner to that for the preparation of 1-(4-bromo-2,6-dimethylphenoxy)-2-phenoxyethane described in Example 15, but using 2-(4-bromophenoxy)ethanol and phenol as starting materials.

EXAMPLE 16

Using a similar procedure to that described in Example 10, but using 1-(4-bromo-3,5-dimethylphenoxy)-2-methoxyethane as starting material in place of 1-(4-bromo-2,6-dimethylphenoxy)-2-methoxyethane, there was obtained 3-[2-(4-{(2-methoxyethoxy}-2,6-dimethylphenyl) ethynyl]quinuclidin-3-ol (7% yield) as a solid, m.p. 140–142° C. (after recrystallisation from acetonitrile); microanalysis, found: C, 72.8; H, 8.1, N, 4.4%; $C_{20}H_{27}NO_3$ requires: C, 72.9; H, 8.3; N, 4.3%; NMR ([$CD_3$]$_2$SO): 1.2–1.4(1H,m), 1.5–1.7(1H,m), 1.8–2.0(3H,m), 2.3(6H,s 2.6–2.8(4H,m), 2.8–3.0(1H,d), 3.05–3.2(1H,d), 3.25(3H,s), 3.6–3.7(1H,d of d), 4.0–4.1(1H,d of d) 5.5(1H,s) and 6.65 (2H,s); m/z 330 (M+H).

The 1-(4-bromo-3,5-dimethylphenoxy)-2-methoxyethane used as starting material was obtained in an analogous manner to that for the preparation of 3-(4-bromo-2,6-dimethylphenoxy)tetrahydrofuran described in Example 14, but using 4-bromo-3,5-dimethylphenol and 2-methoxyethanol as starting materials. There was thus obtained 1-(4-bromo-3,5-dimethylphenoxy)-2-methoxyethane; NMR(CDCl$_3$): 2.4(6H,s), 3.4(3H,s), 3.65–3.75(2H,m), 4.0–4.1(2H,m) and 6.65(2H,s)

EXAMPLE 17

A mixture of 3-ethynyl-3-hydroxyquinuclidine (574 mg), methoxyethyl 2-methoxyethoxy-5-iodobenzoate (1.6 g), bis (triphenylphosphine)palladium (II) chloride (135 mg), copper (I), iodide (75 mg), triethylamine (5 ml) and dimethylformamide (10 ml) was stirred at 70° C. under an atmosphere of argon for 2 hours. The triethylamine and dimethylformamide were removed by evaporation. The residue was purified by flash column chromatography on silica gel (Merck Art No 9385) using a mixture of 3% triethylamine in ethyl acetate as eluent to give, after trituration with dichloromethane/pentane (1:1, 10 ml), 3-[2-(4-(2-methoxyethoxy)-3-(2-methoxyethoxycarbonyl)phenyl) ethynyl]quinuclidin-3-ol (350 mg) as a colourless solid, m.p. 100–102° C.; microanalysis, found: C, 65.7; H, 7.4; N, 3.4%; $C_{22}H_{29}NO_6$ requires: C,65.5; H, 7.2; N, 3.5%; NMR ($[CD_3]_2SO$): 7.6(1H,d), 7.5(1H, d of d), 7.2(1H,d), 5.5(1H, s), 4.3(2H,m), 4.2(2H,m), 3.7–3.6(4H,m), 3.32(3H,s), 3.30 (3H,s), 2.9(2H,m), 2.7(4H,m), 2–1.8(3H,m), 1.6(1H,m), 1.3 (1H,m); m/z 404 (M+H).

The methoxyethyl 2-methoxyethoxy-5-iodobenzoate used as starting material was obtained as follows.

A mixture of 2-hydroxy-5-iodobenzoic acid (1.32 g), bromoethyl methyl ether (1.39 g), potassium carbonate (1.5 g) and dimethylformamide (10 ml) was stirred at 70° C. under an atmosphere of argon for 14 hours. The mixture was cooled to ambient temperature, diluted with water (10 ml) and extracted with ethyl acetate (100 ml). The organic extract was washed with aqueous sodium carbonate solution, dilute aqueous hydrochloric acid, water and saturated brine and dried ($MgSO_4$). Evaporation gave methoxyethyl 2-methoxyethoxy-5-iodobenzoate (1.64 g) as a yellow oil; NMR ($[CD_3]_2SO$): 7.7(2H,m), 6.9(1H,d), 4.2(2H,m), 4.0(2H,m), 3.5(4H,m), 3.20(3H,s) and 3.19(3H,s); m/z 380 (H).

EXAMPLE 18

A mixture of 3-ethynyl-3-hydroxyquinuclidine (453 mg), methoxyethyl 4-bromo-2-chlorophenyl ether (0.97 g), bis (triphenylphosphine)palladium (II) chloride (105 mg), copper (I) iodide (55 mg), triethylamine (5 ml) and dimethylformamide (10 ml) was stirred at 70° C. under an atmosphere of argon for 2 hours. The triethylamine and dimethylformamide were removed by evaporation. The residue was purified by flash column chromatography on silica gel (Merck Art. No. 9385) using a mixture of 10% methanol in dichloromethane containing 1% ammonia (density, 0.880 g/cm³) as eluent. The residue was crystallised from acetonitrile to give 3-[2-(3-chloro-4-(2-methoxyethoxy)phenyl) ethynyl]quinuclidin-3-ol (0.52 g) as a colourless solid, m.p. 138–139° C.; microanalysis, found: C, 64.1; H, 6.7; N, 4.1%; $C_{18}H_{22}ClNO_3$ requires: C, 63.9; H, 6.6; N, 4.1%; NMR ($[CD_3]_2SO$): 7.5(1H,d), 7.3(1H,d of d), 7.1(1H,d), 5.5(1H,s), 4.2(2H,m), 3.7(2H,m), 3.3(3H,s), 2.8(2H,m), 2.7 (4H,m), 2–1.8(3H,m), 1.6(1H,m) and 1.3(1H,m); m/z 336 (M+H).

The methoxyethyl 4-bromo-2-chlorophenyl ether used as starting material was obtained as follows.

A mixture of 4-bromo-2-chlorophenol (1.04 g) bromoethyl methyl ether (0.70 g), potassium carbonate (0.76 g) and dimethylformamide (5 ml) was stirred at 70° C. under an atmosphere of argon for 14 hours. The mixture was cooled to ambient temperature, diluted with water (100 ml) and extracted with ethyl acetate (100 ml). The organic extract was washed with aqueous sodium carbonate, saturated brine and dried ($MgSO_4$). Evaporation gave methoxyethyl 4-bromo-2-chlorophenyl ether (1.14 g) as a colourless oil; NMR ($[CD_3]_2SO$): 7.7(1H,d), 7.5(1H,dd), 6.9(1H,d), 4.2 (2H,m), 3.7(2H,m) and 3.3(3H,s); m/z 264/266 (M+H).

EXAMPLE 19

A mixture of 2-benzyl-1-phenyltrifluoromethane sulphonate (1.27 g), 3-ethynyl-3-hydroxyquinuclidine (604 mg), bis(triphenylphosphine)-palladium (II) chloride (140 mg), copper (I) iodide (70 mg), triethylamine (4 ml) and dimethylformamide (8 ml) was stirred at 70° C. under an atmosphere of argon for 3 hours. The triethylamine and dimethylformamide were removed by evaporation. A 2M aqueous solution of sodium hydroxide (25 ml) was added to the residue and the mixture extracted with dichloromethane. The organic extracts were combined, washed with water and saturated brine, dried ($MgSO_4$) and evaporated. The residue was purified by flash column chromatography on silica gel (Merck Art 9385) using 10% methanol in dichloromethane containing 1% ammonia (density, 0.880 g/cm³) as eluent to give (after re-crystallisation from acetonitrile) 3-[2-(2-benzylphenyl)ethynyl]quinuclidin-3-ol (175 mg) as a solid, m.p. 156–157° C.; microanalysis, found: C, 82.5; H, 7.5; N, 4.5%; $C_{22}H_{23}NO$. $0.1CH_3CN$ requires: C, 82.9; H, 7.3; N, 4.79%; NMR($[CD_3]_2SO$): 1.20–1.35(1H,m), 1.40–1.56(1H, m), 1.65–1.80(1H,m), 1.80–1.95(2H,m), 2.05($CH_3CN$ solvent), 2.50–2.70(4H,m), 2.75–2.85(1H,d), 2.94–3.04(1H, d), 4.10(2H,s), 5.57(1H,s), 7.12–7.33(8H,m) and 7.35–7.43 (1H,d); m/z 318 (M+H).

The 2-benzyl-1-phenyltrifluoromethane sulphonate used as starting material was prepared as follows.

Trifluoromethane sulphonic anhydride (6.5 ml) was added dropwise to a stirred solution of 2-hydroxydiphenylmethane (6.45 g) in pyridine (50 ml) at 0° C. under an atmosphere of argon. The reaction mixture was stirred for 2.5 hours at 0° C. and then allowed to warm to +15° C. The reaction mixture was poured into water and extracted with ethyl acetate. The ethyl acetate extract was washed with water, saturated brine, dried ($MgSO_4$) and evaporated. The residue was purified by flash column chromatography on silica gel (Merck Art 9385) using 5% ethyl acetate/hexane as eluent to give 2-benzyl-1-phenyltrifluoromethane sulphonate as an oil (9.1 g); microanalysis, found: C, 53.1; H, 3.6%; $C_{14}H_{11}F_3O_3S$ requires: C, 53.2; H, 3.51%; NMR($[CD_3]_2$ SO): 4.05(2H,s) and 7.14–7.49(9H,m); m/z 316(M).

EXAMPLE 20

A solution of sodium hydroxide (8.5 g) in water (90 ml) was added at ambient temperature to a stirred mixture of quinuclidin-3-one (8.9 g), 2-hydroxydiphenylmethane (13.0 g) and trimethylsulphoxonium iodide (31.2 g) in toluene (150 ml). The mixture was stirred at ambient temperature for 3 days under an atmosphere of argon.

The mixture was filtered through diatomaceous earth and the filtercake was washed with ethyl acetate (3×60 ml). The filtrate and washings were combined and the organic layer was separated and retained. The aqueous layer was extracted with ethyl acetate (4×130 ml). The retained organic layer and the ethyl acetate extracts were combined and extracted with 2M aqueous hydrochloric acid (4×25 ml). The acid extracts were combined, washed with ethyl acetate (2×100 ml), cooled in ice, basified with 40% sodium hydroxide solution (30 ml) and extracted with ethyl acetate (4×70 ml). The ethyl acetate extracts were combined, washed with saturated brine (50 ml), dried ($Na_2SO_4$) and evaporated. The residue was purified by column chromatography on silica gel (Merck 7736) to give (after trituration with n-pentane) 3-(2-benzylphenoxymethyl)quinuclidin-3-ol (0.13 g) as a colourless solid, m.p. 71–73° C.; microanalysis, found: C, 77.1; H, 7.8; N, 4.5%; $C_{21}H_{25}NO_2$ $0.2H_2O$ requires: C, 77.1; H, 7.8; N, 4.3%; NMR($CDCl_3$): 1.2–1.4(1H,m), 1.4–1.6(2H, m), 1.65–2.1(3H,m), 2.5–3.0(6H,m), 3.65–3.8(1H,d), 3.9–4.1(3H,m), 6.8–6.9(1H,d), 6.9–7.0(1H,m) and 7.05–7.35(7H,m); m/z 324(M+H).

EXAMPLE 21

An ice-cooled solution of 3M aqueous hydrochloric acid (9 ml) in acetone (27 ml) was added to 3-(2-benzyl-4-propionamidophenoxymethyl)-3-hydroxyquinuclidine borane complex (1.9 g). The latter dissolved immediately and the resulting colourless solution was stirred at 5° C. for 1.5 hours. The reaction mixture was evaporated and the residue was dissolved in 2M aqueous hydrochloric acid (50 ml). This acidic aqueous solution was washed with ethyl acetate (3×25 ml), basified with solid sodium carbonate, and extracted with ethyl acetate (3×70 ml). The ethyl acetate extracts were combined, dried ($Na_2SO_4$), and evaporated. The residue was dissolved in hot ethyl acetate (10 ml) and the resulting solution was added to a hot solution of fumaric acid (0.46 g) in ethyl acetate (40 ml)/ethanol (10 ml). The cooled mixture was evaporated to give a foam. This was triturated with ethyl acetate/ether to give a solid which was stored under vacuum over phosphorus pentoxide for 18 hours. There was thus obtained 3-(2-benzyl-4-propionamidophenoxymethyl)quinuclidin-3-ol fumarate (1.2 g) as a solid, m.p. 70–85° C.; microanalysis, found: C, 63.2; H, 7.1; N, 4.7%; $C_{24}H_{30}N_2O_3$ fumarate, 1.0 $H_2O$, 0.33 ethyl acetate, 0.13 ether requires: C, 63.2; H, 7.1; N,4.9%; NMR ($[CD_3]_2SO$): 1.0–1.1(3H,t), 1.4–1.8(3H,m), 2.0–2.3 (4H,m), 2.8–3.2(6H,m), 3.9–4.1(4H,m), 4.5–6.5(1H+$H_2O$), 6.45–6.55(2H,s), 6.85–7.0 (1H,d) 7.1–7.35(6H,m), 7.4–7.5 (1H,m), 9.6–9.7(1H,s); m/z 395 (M+H).

The 3-($^2$-benzyl-4-propionamidophenoxymethyl)-3-hydroxyquinuclidine borane complex used as starting material was obtained as follows.

A solution of borane-tetrahydrofuran complex (135 ml of a 1M solution in tetrahydrofuran) was added portionwise over a period of 30 minutes to a stirred solution of 3-quinuclidinone (16.9 g) in dry tetrahydrofuran (300 ml) at –70° C. The mixture was stirred at –70° C. for 30 minutes. Water (20 ml) was added to the reaction mixture at –70° C. The solvent was removed by evaporation. A saturated solution of brine (250 ml) was added to the residue and the mixture basified by addition of solid sodium carbonate. The mixture was extracted with dichloromethane (4×100 ml). The dichloromethane extracts were combined, silica gel (Merck 9385, 60 g) added and the mixture evaporated to give a free flowing powder. This pre-absorbed material on silica gel was purified by flash column chromatography on a further portion of silica gel using a mixture of 25% ethyl acetate/pentane as eluent to give 3-quinuclidinone borane complex (17.0 g) as a colourless solid, m.p. 162–164° C.; NMR ($CDCl_3$): 0.7–2.3(3H, br), 2.0–2.3(4H, m), 2.7(1H, m), 3.0–3.4(4H, m) and 3.5(2H, s).

Powdered trimethyl sulphoxonium iodide (24.4 g) was added portionwise to a stirred, ice-cooled, suspension of sodium hydride (60% w/w dispersion in mineral oil, 4.4 g; the oil was removed by washing the solid with petroleum ether) in dry dimethyl formamide (140 ml) under an atmosphere of argon whilst maintaining the temperature at 10 to 15° C. The mixture was allowed to warm to room temperature. Solid 3-quinuclidinone borane complex (15.5 g) was added to the stirred mixture whilst maintaining the temperature at 25–30° C. using an ice-bath. The mixture was then stirred at room temperature for 16 hours.

The mixture was poured into water (1400 ml) and the mixture was extracted with ethyl acetate (4×400 ml).

The ethyl acetate extracts were combined, washed with water (3×300 ml), dried ($Na_2SO_4$) and evaporated. The residue was purified by flash column chromatography on silica gel using dichloromethane as eluent to give 3-methylenequinuclidine oxide borane complex (13.8 g) as a colourless solid, m.p. 74–77° C.; microanalysis, found: C, 63.1; H, 10.6; N, 9.2%; $C_8H_{16}BNO$ requires: C, 62.8; H, 10.5; N, 9.2%; NMR ($CDCl_3$): 0.6–2.3(3H, br), 1.6(1H, m), 1.7–1.9(1H, m), 1.9–2.0(2H, m), 2.1–2.3(1H, m), 2.8(2H, q) and 2.9–3.4(6H, m); m/z 152 (M–H).

Solid potassium carbonate (1.6 g) was added to a solution of 2-benzyl-4-propionamidophenol (1.5 g) and 3-methylene quinuclidine oxide borane complex (0.9 g), in dry dimethylformamide (10 ml) under an atmosphere of argon. The mixture was stirred for 3 hours at 70° C. The mixture was poured into water (100 ml) and the mixture was extracted with ethyl acetate (3×70 ml). The ethyl acetate extracts were combined, washed with 2M aqueous sodium hydroxide solution (2×25 ml) and water (2×25 ml), dried ($Na_2SO_4$) and evaporated to give a gum (2.6 g). This gum was purified by flash column chromatography on silica gel (Merck Art No 9385) using 20% ethyl acetate/dichloromethane as eluent. There was thus obtained 3-(2-benzyl-4-propionamidophenoxymethyl)-3-hydroxyquinuclidine borane complex as a gum (2.0 g); NMR($CDCl_3$): 0.5–2.5 (3H, v.br), 1.2–1.3(3H,t), 1.4–1.75(3H,m), 1.9–2.25(3H,m), 2.3–2.5(2H,q), 2.7–3.2(6H,m), 3.7–3.9(2H,q), 3.9–4.0(2H, s), 6.7–6.8(1H,d), 7.05–7.5(8H,m); m/z 407 (M–H).

The 2-benzyl-4-propionamidophenol used as starting material was prepared as follows.

Sodium nitrite (9.48 g) was added to a solution of sulphanilic acid (24.9 g) and sodium carbonate (6.78 g) whilst maintaining the temperature of the reaction mixture at 5° C. The resulting mixture was carefully poured into a mixture of concentrated hydrochloric acid (27 ml of a 28% solution) and ice (150 g). The mixture was allowed to stand for half an hour and the mixture was then added to a mixture of 2-benzylphenol (24 g), 4.7M aqueous sodium hydroxide (150 ml) and ice (150 g) whilst maintianing the temperature below 5° C. The mixture was stirred for one hour, sodium dithionite (58.8 g) was added and the mixture slowly heated to 70° C. The reaction mixture was then allowed to cool to ambient temperature to give a precipitate which was collected by filtration to give a solid (23.47 g). To a solution of this solid (20 g) in water (150 ml), propionic anhydride (32.5 g) was added and the resulting solution heated on a steam bath for 2.5 hours. The solution was allowed to cool to ambient temperature and to stand overnight. The mixture was then extracted with ethyl acetate (100 ml). The ethyl acetate extract was washed with 2N aqueous hydrochloric acid (2×100 ml), saturated aqueous sodium hydrogen carbonate solution (3×100 ml) and water (100 ml), dried ($MgSO_4$) and evaporated to give a 2-benzyl-4-propionamidophenol as a tarry oil (120.72 g); NMR [$CD_3OD$]: 1.15(3H,t), 2.30(2H,q), 3.9(2H,s), 6.75(1H,d) and 7.05–7.3(7H,m).

EXAMPLES 22–64

Using a similar procedure to that described in Example 1 (with exceptions as noted) the following compounds of formula 1 (in which A and B are as indicated below) were prepared from the corresponding compounds of formula 2 (in which Z is bromo unless indicated otherwise) and 3-ethynyl-3-hydroxyquinuclidine. Where compounds of formula 2 are not commercially available preparative details are given.

EXAMPLE 22 A=H, B=$CH_2CH_2CO_2Et$

Purified by flash column chromatography on silica gel using 10% methanol in dichloromethane as eluent, followed by recrystallisation from ethyl acetate to give the title compound as a solid, m.p. 142.2° C.; NMR: 1.5(3H,t), 1.30(1H,m), 1.59(1H,m), 1.88(2H,m), 2.62(2H,t), 2.72(4H, m), 2.82(2H,t), 3.05(1H,m), 3.31(1H,s), 4.03(2H,q), 5.51 (1H,s), 7.20(2H,d) and 7.29(2H,d).

The compound of formula 2 (Z=trifluoromethylsulphonyloxy), m/z 328(M+H), used as starting material was prepared using an analogous procedure to that described in Example 1 for the preparation of ethyl 3-(3-allyl-4-trifluoromethylsulphonyloxyphenyl)propionate from ethyl 3-[(3-allyl-4-hydroxy)phenyl]propionate.

EXAMPLE 23 A=allyl, B=$CH_2CH_2CO_2Me$

Purified by flash chromatography on silica gel using 10% methanol in dichloromethane as eluent, to give the title compound as a solid, m.p. 63–65° C., NMR(CDCl$_3$): 1.44 (1H,), 1.68(1H,m), 2.10(4H,m), 2.62(2H,t), 2.86(6H,m), 3.08(1H,d), 3.32(1H,d), 3.50(2H,d), 3.68(3H,s), 5.05(2H, m), 5.96(1H,m), 7.00(2H,m) and 7.33(1H,d).

The compound of formula 2 (Z=trifluoromethylsulphonyloxy), m/z 354(M+H), used as starting material was prepared using an analogous procedure to that described in Example 1 for the preparation of ethyl 3-(3-allyl-4-trifluoromethylsulphonyloxyphenyl)propionate from ethyl 3-[(3-allyl-4-hydroxy)phenyl]propionate.

EXAMPLE 24 A=H, B=CH=$CHCO_2Et$

Purified by crystallisation from ethyl acetate to give the title compound as a solid, m.p. 180.7° C., NMR: 1.27(3H,t), 1.38(1H,m), 1.65(1H,m), 1.93(3H,m), 3.05(7H,m), 4.20 (2H,q), 5.62(1H,s), 6.63(1H,d), 7.42(2H,d), 7.63(1H,d) and 7.70(1H,d).

The compound of formula 2 (Z=trifluoromethylsulphonyloxy), m/z 326(M+H), used as starting material was prepared using an analogous procedure to that described in Example 1 for the preparation of ethyl 3-(3-allyl-4-trifluoromethylsulphonyloxyphenyl)propionate from ethyl 3-[(3-allyl-4-hydroxy)phenyl]propionate.

EXAMPLE 25 A=allyl, B=CH=$CHCO_2Et$

Purified by chromatography on alumina (Fluka 507C) using a 19:1 (v/v) mixture of ethyl acetate/methanol as eluent, followed by trituration with diethyl ether to give the title compound as a solid, m.p. 141.4° C.; NMR: 1.30(4H, m), 1.60(1H,m), 1.90(3H,m), 2.98(6H,m), 3.52(2H,d), 4.20 (2H,q), 5.07(2H,m), 5.61(1H,s), 5.90(1H,m), 6.60(1H,d), 7.39(1H,d) and 7.60(3H,m).

The compound of formula 2 (Z=trifluoromethylsulphonyloxy), m/z 366(M+H), used as starting material was prepared using an analogous procedure to that described in Example 1 for the preparation of ethyl 3-(3-allyl-4-trifluoromethylsulphonyloxyphenyl)propionate from ethyl 3-[(3-allyl-4-hydroxy)phenyl]propionate.

EXAMPLE 26 A=allyl, B=$(CH_2)_3CO_2Me$

Obtained as a solid, m.p. 34–35° C., NMR(CDCl$_3$): 1.43(1H,m), 1.65(1H,m), 2.01(4H,m), 2.30(2H,t), 2.61(2H, t), 2.85(4H,m), 3.05(1H,d), 3.32(1H,d), 3.67(3H,s), 5.04 (2H,m), 5.97(1H,m), 6.97(2H,m) and 7.31(1H,m).

The compound of formula 2(Z=trifluoromethylsulphonyloxy), m/z 368(M+H), used as starting material was prepared from the methyl ester of 4-(4-hydroxyphenyl)butanoic acid using a method analogous to that described in Example 1 for the preparation of ethyl 3-(3-allyl-4-trifluoromethylsulphonyloxyphenyl) propionate.

EXAMPLE 27 A=allyl, B=$(CH_2)_4CO_2Me$

Purified by chromatography on alumina (Fluka 507C) using a 19:1 (v/v) mixture of ethyl acetate/methanol as eluent to give the title compound as a solid, m.p. 35–37° C.; NMR(CDCl$_3$): 1.44(1H,m), 1.70(5H,m), 2.02(3H,m), 2.31 (2H,t), 2.60(2H,t), 2.86(4H,m), 3.05(1H,d), 3.33(1H,dd), 3.50(2H,d), 3.67(3H,s), 5.03(2H,m), 5.95(1H,m), 6.97(2H, m) and 7.31(1H,d).

The compound of formula 2 (Z=trifluoromethylsulphonyloxy), m/z 382(M+H), was prepared from methyl 5-(4-hydroxyphenyl)pentanoate using a method analogous to that described in Example 1 for the preparation of ethyl 3-(3-allyl-4-trifluoromethylsulphonyloxyphenyl)propionate.

EXAMPLE 28 A=allyl, B=$CH_2CH_2CO_2CH(Me)Et$

Purified by flash chromatography on silica gel using a 9:1 (v/v) mixture of dichloromethane/methanol as eluent to give a solid, m.p. 49–51° C.; NMR(CDCl$_3$): 0.86(3H,t), 1.15(3H, d), 1.55(4H,m), 2.05(3H,m), 2.58(2H,t), 2.86(6H,m), 3.06 (1H,d), 3.34(1H,d), 3.51(2H,d), 3.82(1H,m), 5.05(2H,m), 5.97(1H,m), 7.01(2H,m) and 7.32(1H,d).

The compound of formula 2(Z=trifluoromethylsulphonyloxy), (M+H)=396, used as starting material was prepared by using a method analogous to that described in Example 1 for the preparation of ethyl 3-(3-allyl-4-trifluoromethylsulphonyloxyphenyl)propionate.

EXAMPLE 29 A=allyl, B=$(CH_2)_2CO_2CH_2CO_2Me$

Purified by chromatography on alumina (Fluka 50C) using a 19:1 (v/v) mixture of ethyl acetate/methanol as eluent to give a solid, m.p. 73–75° C.; NMR(CDCl$_3$): 1.42(1H,m), 1.67(1H,m), 2.01(3H,m), 2.33(1H,m), 3.03 (1H,d), 3.32(1H,dd), 3.50(2H,d), 3.75(3H,s), 4.61(2H,s), 5.04(2H,d), 5.95(1H,m), 7.02(2H,m) and 7.33(1H,d).

EXAMPLE 30 A=allyl, B=$(C_2)_2CO_2(CH_2)_2OM$

Purified by chromatography on alumina (Fluka 507C) using a 19:1 (v/v) mixture of ethyl acetate/methanol as eluent to give an oil, NMR(CDCl$_3$): 1.44(1H,m), 1.69(1H, m), 2.06(3H,m), 2.62(2H,t), 2.87(6H,m), 3.10(1H,m), 3.35 (4H,m), 3.52(4H,m), 4.21(2H,m), 5.04(2H,m), 5.95(1H,m), 7.02(2H,m) and 7.32(1H,d).

EXAMPLE 31 A=H, B=$OCH_2CH_2OCH_2$

Purified by flash chromatography on silica gel using 10% methanol in dichloromethane containing 1% ammonia (density, 0.88 g/cm$^3$) as eluent to give a gum, NMR([CD$_3$]$_2$ SO): 1.5–1.7(3H,m), 1.9–2.1(2H,m), 2.8–3.65(6H,m), 3.3 (3H,s), 3.3–3.4(1H,m), 3.6–3.68(2H,m), 4.05–4.13(2H,m), 6.9(2H,d) and 7.32(2H,d).

EXAMPLE 32 A=allyl, B=$CO_2CH_2CH_2OCH_3$

Purified by flash chromatography on silica gel using 10% methahol in dichloromethane containing 1% ammonia (density, 0.88 g/cm$^3$) as eluent to give a solid, m.p. 90–92° C., NMR: 1.21–1.41(1H,m), 1.50–1.69(1H,m), 1.75–2.02 (3H,m), 2.68(4H,t), 2.80–3.15(2H,q), 3.30(3H,s), 3.53–3.70 (4H,m), 4.35–4.45(2H,m), 5.00–5.16(2H,m), 5.67(1H,s), 5.87–6.10(1H,m), 7.50–7.57(1H,d) and 7.77–7.85(2H,m).

The compound of formula 2 (Z=trifluoromethylsulphonyloxy) used as starting material was prepared as follows.

Anhydrous potassium carbonate (55 g) in acetone (400 ml) and allyl bromide (41.5 ml) were added to a stirred solution of methyl 4-hydroxybenzoate (60.8 g). The mixture was heated at reflux for 18 hours. The reaction mixture was cooled to ambient temperature, filtered and the residue washed with ethyl acetate. The filtrates and washings were combined, evaporated and the residue dissolved in dichloromethane. The organic phase was washed with 1M aqueous sodium hydroxide (2×75 ml), water, brine and dried ($MgSO_4$). Evaporation gave methyl 4-allyloxybenzoate as an oil (76.4 g) which was used without further purification.

A mixture of methyl 4-allyloxybenzoate (1.92 g), sodium cyanide (50 mg) and 2-methoxyethanol (20 ml) was heated at reflux for 24 hours. The mixture was evaporated to give an oil which was partitioned between dichloromethane and water. The organic phase was separated, washed with brine, dried ($MgSO_4$) and evaporated. The residue was purified by flash column chromatography on silica gel using a 9:1 (v/v) mixture of pentane/ethyl acetate as eluent to give 2-methoxyethyl 4-allyloxybenzoate (1.7 g) as an oil; NMR ($CDCl_3$): 3.44(3H,s), 3.72(2H,t), 4.44(2H,t), 4.55–4.64(2H, m), 5.27–5.48(2H,m), 5.96–6.14(1H,m), 6.93(2H,d) and 8.01(2H,d); m/z237(M+H).

2-methoxyethyl 4-allyloxybenzoate (1.7 g) was heated at 250–260° C. for 0.5 hour and the crude product was purified by flash column chromatography on silica gel using 3:2 (v/v) mixture of pentane/ethyl acetate as eluent to give 2-methoxyethyl 3-allyl-4-hydroxybenzoate as an oil (1.36 g); NMR($CDCl_3$): 3.42(2H,d), 3.44(3H,s), 3.74(2H,t), 4.44 (2H,q), 5.08–5.20(2H,m), 5.89–6.10(1H,m), 6.02(1H,s), 6.81(1H,d) and 7.77–7.85(2H,m); m/z237(M+H).

The triflate was prepared using trifluoromethane sulphonic anhydride using the procedure described in Example 1 for the preparation of 3-(3-allyl-4-trifluoromethylsulphonyloxyphenyl)propionate. There was thus obtained 2-allyl-4-methoxyethoxycarbonylphenyltrifluoromethane sulphonate as an oil; NMR($CDCl_3$): 3.42(3H,s), 3.47–3.57(2H,d), 3.72 (2H,t), 4.48(2H,t), 5.07–5.25(2H,m), 5.80–6.05(1H,m), 7.30–7.40(1H,d) and 7.95–8.08(2H,m); m/z 369(M+H).

EXAMPLE 33 A=H, B=$OCH_2CH_2SCH_3$

Purified by triturating with diethyl ether, followed by recrystallisation from acetonitrile to give a solid, m.p. 154–155° C., NMR: 1.2–1.4(1H,m), 1.5–1.6(1H,m), 1.8–2.0 (3H,m), 2.15(3H,s), 2.68(4H,t), 2.7–2.9(3H,m), 3.05(1H,d), 4.17(2H,t), 6.92(2H,d) and 7.32(2H,d).

The compound of formula 2 (Z=bromo) was prepared as follows.

Diethyl azodicarboxylate (13.4 g) was added over a period of 20 minutes to a stirred solution of 4-bromophenol (12 g), 2-methylthioethanol (6.4 g) and triphenylphospine (18.2 g) in tetrahydrofuran (250 ml) at −5° C. under an atmosphere of argon. The mixture was stirred at ambient temperature for 1 hour and the solvent was then removed by evaporation. The residue was partitioned between dichloromethane (150 ml) and water (150 ml). The aqueous phase was separated and extracted with dichloromethane (150 ml). The dichloromethane extracts were combined, washed with water (2×100 ml), dried ($MgSO_4$) and evaporated. The residue was dissolved in a boiling mixture of toluene (50 ml) and n-heptane (50 ml). The solution was chilled and the precipitated triphenylphosphine oxide removed by filtration. The filtrate was evaporated and purified by medium pressure chromatography on silica gel using a 1:1 (v/v) mixture of toluene/n-heptane as eluent to give 1-(4-bromophenoxy)-2-methylthioethane as an oil (10.2 g); NMR($CDCl_3$): 2.2(3H, s), 2.88(2H,t), 4.12(2H,t), 6.77(2H,d) and 7.37(2H,d).

EXAMPLE 34 A=H, B=$CH_2OCH_2OCH_3$

Purified by triturating with diethyl ether, followed by recrystallisation from acetonitrile, to give a solid, m.p. 148–150° C.; NMR: 1.2–1.4(1H,m), 1.5–1.7(1H,m), 1.8–2.0 (3H,m), 2.6–2.75(4H,t), 2.75–2.9(1H,d), 3.0–3.1(1H,d), 3.3 (3H,s), 4.5(2H,s), 4.65(2H,s), 5.5(1H,s) and 7.23–7.45(4H, dd).

The compound of formula 2 (Z=bromo) was prepared as follows.

Dimethoxymethane (80 ml) and phosphorous pentoxide (40 g) were added to a solution of 4-bromobenzyl alcohol (3.74 g) in dry dichloromethane (80 ml). The resultant slurry was stirred for one hour at room temperature and was then added to a cooled saturated sodium carbonate solution (600 ml). The mixture was extracted with ether (3×200 ml). The organic extracts were combined, washed with water (25 ml), brine (25 ml), dried with ($MgSO_4$) and evaporated.

The residue was purified by vacuum flash chromatography on silica gel (Merck 7736) using 50% toluene/hexane as eluent to give 4-bromobenzyloxymethoxymethane as a colourless oil 2.6 g. NMR: ($CDCl_3$): 3.4(3H,s), 4.5(2H,s), 4.7(2H,s), 7.2–7.3(2H,d) and 7.4–7.5(2H,d).

EXAMPLE 35 A=allyl, B=$(CH_2)_3OCH_3$

Purified by flash chromatography on silica gel using 5% methanol in dichloromethane containing 0.5% ammonia (density, 0.88 g/cm$^3$) as eluent to give an oil, NMR: 1.3–1.5 (1H,m), 1.55–1.7(1H,m), 1.7–1.85(2H,m), 1.85–2.05(3H, m), 2.55–2.65(2H,t), 2.7–2.9(4H,m), 2.9–3.0(1H,d), 3.1–3.2 (1H,d), 3.2(3H,s), 3.25–3.35(2H,t), 3.45–3.5(2H,d), 5.0–5.1 (2H,m), 5.7(1H,s), 5.9–6.1(1H,m), 7.0–7.1(2H,d) and 7.2–7.3(1H,d).

The compound of formula 2 (Z=trifluoromethylsulphonyloxy) used as starting material was prepared as follows.

Powdered potassium carbonate (4.14 g) and allyl bromide (3.99 g) were added to a stirred solution of 3-(4-hydroxyphenyl)propanol (4.56 g) in acetone (15 ml) under an atmosphere of argon. The mixture heated at reflux for 20 hours. After cooling to ambient temperature the solid potassium bromide was removed by filtration and washed with ether. The filtrate and washings were combined, washed with 2M aqueous sodium hydroxide (2×20 ml), water (1×20 ml), brine (20 ml), dried ($MgSO_4$) and evaporated. The residue was purified by vacuum flash chromatography on silica gel (Merck 7736) using toluene as eluent to give 3-(4-allyloxyphenyl) propanol as a colourless oil (4.6 g). NMR($CDCl_3$): 1.3(1H,s), 1.8–2.0(2H,m), 2.6–2.7(2H,t), 3.6–3.7(2H,t), 4.45–4.55(2H,m), 5.2–5.5(2H,m), 5.95–6.15 (1H,m), 6.8–6.9(2H,d) and 7.05–7.15(2H,d).

Thionyl chloride (2 ml) was added dropwise to a solution of 3-(4-allyloxyphenyl)propanol (4.7 g) in toluene (50 ml) containing pyridine (2.5 ml). The reaction mixture was stirred for 16 hours at room temperature and was then added to water (80 ml). The mixture was extracted with toluene (3×50 ml), washed with water (20 ml), brine (20 ml) dried ($MgSO_4$) and evaporated.

The residue was purified by vacuum flash chromatography on silica gel (Merck 7736) using toluene as eluent to give, 3-(4-allyloxyphenyl)propyl chloride (5.1 g); NMR ($CDCl_3$): 1.9–2.1(2H,m), 2.6–2.7(2H,t), 3.85–4.1(2H,m), 4.45–4.55(2H,m), 5.2–5.5(2H,m), 5.9–6.2(1H,m), 6.8–6.9 (2H,d) and 7.0–7.1(2H,d).

A mixture of 3-(4-allyoxyphenyl)propyl chloride (6.1 g), dimethyl formamide (50 ml), dibromomethane (25 ml) and sodium bromide (3.28 g) was heated for 16 hours at 100° C. The mixture was poured into water (20 ml) and extracted with ether (3×50 ml). The organic extracts were combined, washed with water (20 ml), brine (20 ml), dried (MgSO$_4$) and evaporated. The residue was purified by vacuum flash chromatography on silica gel (Merck 7736) using 5% ethyl acetate in hexane as eluent to give 3-(4-allyloxyphenyl) propyl bromide as a colourless oil (4.0 g); NMR(CDCl$_3$): 2.0–2.2(2H,m), 2.65–2.8(2H,t), 3.3–3.4(2H,t), 4.45–4.55 (2H,m), 5.2–5.5(2H,m), 5.9–6.2(1H,m), 6.8–6.9(2H,d) and 7.1–7.2(2H,d).

3-(4-allyoxyphenyl)propyl bromide (4.0 g) was added dropwise to a cooled solution of methanol (50 ml) and mercury II perchlorate prepared from mercury II oxide (3.39 g) and 60% perchloric acid (4.71 ml). The mixture was stirred for 16 hours at room temperature. Saturated brine (80 ml) was added and the mercury salts were removed by filtration and the residue washed with ether (30 ml). The aqueous layer from the filtrate was separated and further extracted with ether (3×100 ml). The organic extracts were combined, were washed with water (2×20 ml), brine (1×20 ml), dried (MgSO$_4$) and evaporated.

The residue was purified by flash chromatography on silica gel using 5% ethyl acetate in toluene as eluent to give 3-(4-allyloxyphenyl-1-methoxypropane as a colourless oil (1.6 g) NMR(CDCl$_3$): 1.8–2.0(2H,m), 2.6–2.7(2H,t), 3.3–3.5(5H,m), 4.45–4.55(2H,m), 5.2–5.5(2H,m), 5.95–6.15(1H,m), 6.8–6.9(2H,d) and 7.05–7.15(2H,d).

The 3-(4-allyloxyphenyl)-1 methoxypropane was heated at 200° C. for 2 hours under an atmosphere of argon. The product was dissolved in ether and extracted with 2M aqueous sodium hydroxide (4×20 ml). The aqueous extracts were combined, and acidified with 2M aqueous hydrochloric acid. The mixture was extracted with ether (2×30 ml), the ether extracts were combined, washed with water (10 ml), brine (10 ml), dried (MgSO$_4$) and evaporated to give 3-(2-allyl, 4-hydroxyphenyl), 1-methoxypropane a colourless oil (940 mg) which was used without further purification; NMR(CDCl$_3$): 1.8–2.0(2H,m), 2.5–2.6(2H,t), 3.3–3.45(7H, t), 4.8(1H,s), 5.1–5.2(2H,m), 5.9–6.1(1H,m), 6.7–6.8(1H,d) and 6.9–7.0(2H,d).

Using a similar procedure to that described in Example 1 for the preparation of ethyl 3-(3-allyl-4-trifluoromethylsulphonyloxyphenyl)propionate but using 3-(2-allyl-4-hydroxyphenyl)-1-methoxypropane as starting material there was obtained 2-allyl-4-(3-methoxypropyl) phenyl trifluoromethane sulphonate as a colourless oil; NMR(CDCl$_3$): 1.8–1.95(2H,m), 2.65–2.75(2H,t), 3.3–3.5 (7H,m), 5.05–5.2(2H,m), 5.8–6.0(1H,m) and 7.0–7.3(3H, m).

EXAMPLE 36 A=H, B=CH$_2$CH$_2$OCH$_2$CH$_2$OCH$_3$

Purified by flash chromatography on silica gel using 5% methnol in dichloromethane containing 0.5% ammonia (density, 0.88 g/cm$^3$) as eluant to give a solid, m.p. 126–127° C.; NMR: 1.2–1.4(1H,m), 1.5–1.65(1H,m), 1.8–2.0(3H,m), 2.6–2.7(4H,t), 2.75–2.9(3H,m), 3.0–3.1(1H,d), 3.25(3H,s), 3.35–3.45(2H,m), 3.45–3.55(2H,m), 3.55–3.65(2H,t), 5.55 (1H,s), 7.2–7.3(2H,d) and 7.3–7.4(2H,d).

The compound of formula 2 (Z=bromo) used as starting material was prepared as follows.

4-bromophenethyl bromide (4.0 g) was added in a dropwise manner to a cooled solution of methoxyethanol (50 ml) and mercury II perchlorate (prepared from 3.39 g of mercury II oxide and 4.71 g of 60% perchloric acid). The mixture was stirred overnight at ambient temperature. Saturated brine (80 ml) was added, the mercury salts removed by filtration and washed with ether. The filtrate was extracted with ether (3×100 ml). The ether extracts were combined, washed with water (20 ml), saturated brine (20 ml), dried (MgSO$_4$) and evaporated. The residue was purified by flash chromatography on silica gel using 10% ethyl acetate in toluene as eluent to give 1-(-4-bromophenethyloxy)-2-methoxyethane (2.2 g) as a colourless oil; NMR(CDCl$_3$): 2.8–2.9(2H,t), 3.4(3H,s), 3.5–3.6(4H,m), 3.6–3.75(2H,t 7.05–7.15(2H,d) and 7.35–7.45(2H,d).

EXAMPLE 37 A=H, B=CONHCH$_2$CO$_2$Me

Purified by flash chromatography on silica gel using 10% methanol in dichloromethane containing 1% ammonia (density 0.88 g/cm$^3$) as eluent, followed by recrystallisation from ethanol to give a solid, m.p. 200–202° C.; NMR: 1.2–1.4(1H,m), 1.5–1.7(1H,m), 1.8–2.0(3H,m), 2.6–2.8(4H, m), 2.8–2.9(1H,d), 3.05–3.15(1H,d), 5.65(1H,s), 3.78(3H,s), 4.15(2H,s), 6.0(1H,s), 7.6(2H,d), 8.0(2H,d) and 9.12(1H,m).

The compound of formula 2 (Z=iodo) used as starting material was prepared as follows:

Triethylamine (5.4 ml) was added to a solution of 4-iodobenzoyl chloride (5.06 g) in dichloromethane (30 ml) at 5° C. Glycine methyl ester hydrochloride (2.4 g) was then added to the reaction mixture and the mixture was stirred at 5° C. for 2 hours. The mixture was then stirred at ambient temperature overnight. Dichloromethane (100 ml) was added and the mixture was washed with water (2×100 ml), dried (MgSO$_4$) and evaported. The residue was triturated with pentane to give a solid which was collected by filtration to give methyl 4-iodohippurate, m.p. 166–168° C. NMR: 3.65(3H,s), 4.0(2H,d), 7.65(2H,m), 7.88(2H,m) and 9.0(1H, m); m/z 320(M+H).

EXAMPLE 38 A=H, B=CONH(CH$_2$)$_2$OCH$_3$

Purified by flash chromatography on silica gel using 10% methanol in dichloromethane containing 1% ammonia (density, 0.88 g/cm$^3$) as eluent followed by recrystallisation acetonitrile to give a solid, m.p. 165–167° C.; NMR: 1.2–1.4 (1H,m), 1.5–1.7(1H,m), 1.8–2.0(3H,m), 2.6–2.8(4H,m), 2.8–2.9(1H,d), 3.05–3.15(1H,d), 3.3(2H,m), 3.45(5H 5.64 (1H,s), 5.65(1H,s), 7.45(2H,d), 7.82(2H,d) and 8.5(1H,m).

The compound of formula 2 (Z=iodo) used as starting material was prepared in an analogous manner to the compound of formula 2 in Example 37 in 89% yield, NMR: 3.3(3H,s), 3.45(4H,m), 7.62(2H,m), 7.85(2H,m) and 8.55 (1H,m); m/z 306(M+H).

EXAMPLE 39 A=H, B=CH$_2$OCOCH(CH$_3$)$_2$

Purified by flash chromatography on silica gel using a 80:20:3 (v/v/v) mixture of ethyl acetate/ethanol/ triethylamine as eluent, followed by trituration with acetonitrile to give a solid, NMR: 0.9(6H,d), 1.2–1.4(1H,m), 1.5–1.7(1H,m), 1.8–2.0(3H,m), 2.23(2H,d), 2.6–2.8(4H,m), 2.8–2.9(1H,d), 3.05–3.15(1H,d), 5.1(2H 5.65(1H,s), 5.58 (1H,s) and 7.37(4H,m).

The compound of formula 2 (Z=bromo) was prepared as follows.

A mixture of 4-bromobenzyl alcohol (1 g) pyridine (0.6 ml) and dichloromethane (40 ml) was stirred under an atmosphere of argon at 3° C. for 0.5 hours. Isovaleryl chlorile (0.73 ml) was added to the reaction mixture dropwise over a period of 5 minutes. The mixture was stirred at 5° C. for 15 minutes, allowed to warm to ambient room temperature and stirred at ambient temperature for 1 hour.

The reaction mixture was washed with 2M aqueous hydrochloric acid (20 ml), water (20 ml), and brine (20 ml), dried (MgSO$_4$) and evaporated to give a colourless oil (1.4 g). NMR: 0.9(6H,d), 2.0(2H,m), 2.2(2H,d), 5.05(3H,m), 7.35 (2H,m) and 7.6(2H,m); m/z 272 (M+H).

EXAMPLE 40 A=H, B=O(CH$_2$)$_2$CN

Triturated with a 80:20:3 (v/v/v) mixture of ethyl acetate/ethanol/triethylamine to give a solid, NMR: 1.2–1.4(1H,m), 1.5–1.7(1H,m), 1.8–2.0(3H,m), 2.6–2.8(4H,m), 2.8–2.9(1H, d), 3.05–3.15(1H,d), 5.65(1H,s), 2.99(3H,t), 4.2(3H,t), 5.5 (1H,s), 6.95(2H,s) and 7.35(2H,s).

The compound of formula z (Z=iodo) used as starting material was prepared as follows.

A 40% solution of benzyltrimethyl ammonium hydroxide in water (1.2 ml) was added to a stirred solution of 4-iodophenyl (4 g) in acrylonitrile (10 ml) whilst under an atmosphere of argon. The temperature of the reaction mixture was raised to 80° C., gradually over 2 hours and was then heated at reflux for 2 days. The reaction mixture was cooled to ambient temperature, diluted with toluene (100 ml) and evaporated. The residue was partitioned between 1M aqueous sodium hydroxide (20 ml) and ether (30 ml). The aqueous phase was separated and extracted with ether (2×30 ml). The ether extracts were combined, washed with water (20 ml), brine (20 ml), dried (MgSO$_2$) and evaporated to give a solid (1.6 g) which was used without further purification.

EXAMPLE 41 A=CHO, B=OCH$_2$CH$_2$OCH$_3$

Obtained as a solid, m.p. 116–118.5° C.; NMR(CDCl$_3$): 1.45(1H,m), 1.70(1H,m), 2.05(3H,m), 2.84(4H,t), 3.09(1H, d), 3.3(1H,d), 3.45(3H,s), 3.76(2H,m), 4.18(2H,m), 7.15 (1H,dd), 7.48(2H,m) and 10.43(1H,s).

The compound of formula 2 (Z=trifluoromethylsulphonylloxy) used as starting material was prepared as follows.

Bromoethylmethyl ether (105.7 g) was added to a stirred suspension of hydroquinone monobenzylether and unhydrous potassium carbonate (84.5 g) in N,N-dimethylformamide (250 ml). The reaction mixture was heated at 90° C. for 18 hours. The reaction mixture was allowed to cool to ambient temperature and the mixture filtered. The filtrate was dissolved in water (750 ml) and the aqueous mixture was extracted with ethyl acetate (5×150 ml). The ethyl acetate extracts were combined, washed with water (3×100 mls), brine (200 mls), dried (MgSO$_4$) and evaporated to give 1-(benzyloxy)-4-(2-methoxyethoxy) benzene (102.4 g) as a solid; NMR: 3.3(3H,s), 3.61(2H,m), 4.0(2H,m), 5.02(2H,s), 6.9(4H,m) and 7.4(5H,m) and m/z 259(M+H).

A mixture of 1-(benzyloxy)-4-(2-methoxyethoxy) benzene (180 g), ethanol (2000 ml) and palladium on carbon catalyst (20 g) was stirred under an atmosphere of hydrogen, at room temperature and atmospheric pressure. After the theoretical quantity of hydrogen had been consumed, the reaction mixture was filtered. The filtrate was evaporated to give a solid which was crystallised from a mixture of ethyl acetate and n-hexane to give 4-(2-methoxyethoxy)phenol as a solid (94.7 g) m.p. 97.9° C.; microanalysis, found: C, 64.3%; H, 7.4%; C$_9$H$_{12}$O$_3$ requires: C, 64.3%; H, 7.2%; NMR: 3.35(3H,s), 3.6(2H,m), 3.95(2H,m), 6.7(4H,m) and 8.9(1H,s); m/z 169(M+H).

A solution of 4-(2-methoxyethoxy)phenol in toluene (350 ml) was added to a solution of magnesium methoxide in methanol (8% by weight solution, 331 mls), under an atmosphere of argon. The reaction mixture was heated at reflux for 2 hours. Toluene (350 mls) was added and the reaction mixture distilled at atmospheric pressure until the internal temperature reached 92° C. A mixture of paraformaldehyde in toluene (300 ml) was added to the reaction mixture and the reaction mixture was heated at reflux for 3.5 hours. The mixture was cooled to ambient temperature and then stirred at ambient temperature for 18 hours. The reaction mixture was diluted with toluene (400 ml), washed with 2M aqueous hydrochloric acid (2×150 ml) and water (to pH 1). The residue was distilled under vacuum to give 2-hydroxy-5-(2-methoxyethoxy)benzaldehyde as an oil (35 g), bp 104–130° C. [0.01 mm Hg]; NMR(CDCl$_3$): 3.45(3H, s), 3.75(2H,m), 4.12(2H,m), 6.92(1H,d), 7.05(1H,d), 7.2 (1H,dd), 9.84(1H,s) and 10.63(1H,s); m/z 197(M+H).

Trifluoromethyl sulphonic anhydride (3.88 ml) was added dropwise over a period of 10 minutes to a stirred solution of 2-hydroxy-5-(2-methoxyethoxy)benzaldehyde (4.11 g) and 2,6-dimethylpyridine (2.67 ml) in dichloromethane (20 ml) at 0° C. under an atmosphere of argon. After stirring at room temperature for 16 hours, the mixture was added to ice (100 g). The organic phase was separated, washed with 5% aqueous sodium carbonate solution (2×10 ml), dried (MgSO$_4$) and evaporated to give an oil which was purified by flash column chromatography on silica gel using dichloromethane as eluent to give 2-trifluoromethylsulphonyloxy-5-(2-methoxyethoxy)benzaldehyde (2.2 g) as an oil; NMR (CDCl$_3$): 3.45(3H,s), 3.78(2H,m), 4.19(2H,m), 7.3(2H,m), 7.48(1H,d) and 10.23(1H,d); m/z 329(M+H).

EXAMPLE 42 A=allyl, B=OCH(CH$_3$)CO$_2$CH$_3$

Purified by flash chromatography on silica gel using a 90:09:01 (v/v/v) mixture of ethyl acetate/methanol/ammonia (density, 0.88 g/cm$^3$) as eluent to give an oil, NMR: (CDCl$_3$) 1.3–1.5(1H,m), 1.55–1.76(4H,m), 1.9–2.5(3H,m), 2.7–3.0 (4H,m), 3.0–3.2(1H,d), 3.2–3.4(1H,dd), 3.4–3.5(2H,d), 3.7–3.8(3H,ms), 4.7–4.8(1H,d), 5.0–5.15(2H,m), 5.8–6.05 (1H,m), 6.6–6.8(2H,m) and 7.3–7.4(1H,d).

EXAMPLE 43 A=allyl, B=(CH$_2$)$_2$CO$_2$Me

Obtained as a gum, NMR: 1.2–1.5(5H,m), 1.5–1.9(3H, m), 1.9–2.15(4H,m), 2.2–2.4(2H,t), 2.5–2.65(2H,t), 2.7–3.0 (4H,m), 3.0–3.1(1H,d), 3.3–3.4(1H,dd), 3.45–3.55(2H,d), 3.65(3H,s), 5.0–5.1(2H,m), 5.9–6.1(1H,m), 6.9–7.0(2H,m) and 7.3–7.4(1H,d).

The compound of formula 2 (Z=trifluoromethylsulphonyloxy) used as starting material was prepared in an analogous manner to the preparation of ethyl 3-(3-allyl-4-trifluoromethylsulphonyloxyphenyl) propionate described in Example 1.

EXAMPLE 44 A=allyl, B=(CH$_2$)$_2$CO$_2$(CH$_2$)$_5$CH$_3$

Purified by chromatography on alumina (Fluka 507C) using a 19:1 (v/v) mixture of ethyl acetate/methanol as eluent to give a solid, m.p. 39–41° C., NMR(CDCl$_3$): 0.90(3H,t), 1.30(6H,s), 1.42(1H,m), 1.61(3H,m), 2.00(3H, m), 2.26(2H,m), 2.58(2H,t), 2.86(6H,m), 3.05(1H,d), 3.30 (1H,d), 3.50(2H,d), 4.04(2H,t), 5.04(2H,m), 5.95(1H,m), 7.00(2H,m) and 7.31(4H,d).

EXAMPLE 45 A=CH$_2$CO$_2$Et, B=H

Purified by crystallisation from acetonitrile to give a solid, m.p. 137.5–138.5° C.; NMR: 1.2(3H, t), 1.3(1H, m), 1.6(1H, m), 1.8–2.0(3H, m), 2.7(4H, m), 2.8(1H, d), 3.1(1H, d), 3.8(2H, s), 4.1(2H, q), 5.6(1H, s) and 7.2–7.4(4H, m).

The compound of formula 2 (Z=iodo) used as starting material was prepared as follows.

A solution of 2-(2-iodophenyl)acetonitrile (2.82 g) in a mixture of 1:1 (v/v) ethanol/water (70 ml) was treated with sodium hydroxide (2.4 g) and stirred at reflux for 4 hours. The resultant solution was cooled to ambient temperature, concentrated to 30 ml, diluted with water (100 ml) and washed with ethyl acetate (2×100 ml). The organic layers were combined and extracted with 2M aqueous sodium hydroxide solution (100 ml). The aqueous layer was acidified to pH 1 with concentrated hydrochloric acid and filtered. The solid collected was washed with water and vacuum dried to give 2-(2-iodophenyl)acetic acid (1.45 g) as a solid, m.p. 110–113° C.; microanalysis; found: C, 36.9; H; 2.7%; $C_8H_7IO_2$ requires: C, 36.7; H, 2.7%; NMR: 3.7(2H, s), 7.0(1H, m), 7.4(2H, m), 7.8(2H, d); 12.5(1H, br s).

Extraction of the acidic aqueous layers with dichloromethane gave a further portion of the same product (0.5 g), >90% pure by NMR.

A solution of 2-(2-iodophenyl)acetic acid in ethanol (20 ml) was treated with concentrated sulphuric acid (0.5 ml) and heated at reflux for 18 hours. The resultant solution was cooled to ambient temperature, concentrated to 5 ml and diluted with saturated aqueous sodium hydrogen carbonate solution (30 ml). Extraction with ethyl acetate (2×50 ml) gave an oil (450 mg) which was purified by chromatography on silica gel eluting with 20% ethyl acetate in hexane to give ethyl 2-(2-iodophenyl)acetate as a solid, m.p. 40.5–41.5° C.; NMR: 1.2(3H, t), 3.8(2H, s), 4.1(2H, q), 7.0(1H, m), 7.4(2H, m) and 7.9(1H, d).

EXAMPLE 46 A=CH$_2$SEt, B=H

Purified by chromatography on silica gel (Varian Bond-Elut S1 silica gel) using a gradient of methanol in dichloromethane containing 1% ammonia (density, 0.88 g/cm$^3$) as eluent, followed by crystallisation from acetonitrile, to give a solid, m.p. 126–127.5° C.; NMR: 1.2(3H, t), 1.3(1H, m), 1.6(1H, m), 1.8–2.0(3H, m), 2.4(2H, q), 2.7(4H, m), 2.9(1H, d), 3.1(1H, d), 3.9(2H, s), 5.6(1H, s) and 7.2–7.4(4H, m).

The compound of formula 2 (Z=iodo) used as a starting material was prepared using the procedures described for the preparation of the compound of formula 2 in Example 47 except the reaction was carried out on double the scale and ethanethiol (0.65 ml) and potassium carbonate (1.32 g) were used in place of sodium methanethiolate.

There was thus obtained 2-ethylthiomethyliodobenzane (1.98 g) as a colourless oil; NMR: 1.2(3H, t), 2.4(2H, q), 3.8(2H, s), 7.0(1H, m), 7.4(2H, m) and 7.9(1H, m).

EXAMPLE 47 A=CH$_2$SMe, B=H

Purified by trituration with acetonitrile to give a solid, m.p. 118–119.5° C., NMR: 1.2(1H, m), 1.4(1H, m), 1.7–1.8 (3H, m), 1.8(3H, s), 2.5(4H, m), 2.7(1H, d) 2.9(1H, d), 3.6(2H, s), 5.4(1H, s) and 7.0–7.3(4H, m).

The starting material (Z=iodo) was prepared as follows.

A solution of 2-chloromethyliodobenzene (1.01 g) in ethanol (15 ml) was deoxygenated with a stream of argon and was then treated with sodium methanethiolate (336 mg) and sodium borohydride (182 mg). The suspension was stirred vigorously at ambient temperature for 22 hours and was then diluted with diethyl ether (40 ml), washed with water (2×30 ml) and brine (30 ml). The aqueous layers were back-extracted with ether, the organic layers were combined, dried (MgSO$_4$) and concentrated to give 2-methylthiomethyliodobenzene (1.02 g) as a colourless oil (used in the next step without further purification); NMR: 2.0(3H, s), 3.8(2H, s), 7.0(1H, m), 7.4(2H, m)and 7.9(1H, d).

EXAMPLE 48 A=allyl, B=CO$_2$(CH$_2$)$_3$OCH$_2$CH$_3$

Purified by flash chromatography on silica gel using 10% methanol in dichloromethane containing 1% ammonia (density, 0.88 g/cm$^3$) as eluent to give a solid, m.p. 75–77° C., NMR (CDCl$_3$): 1.20(3H,t), 1.34–1.53(1H, m), 1.53–1.80 (2H, m), 1.90–2.15(5H, m), 2.75–3.06(5H, m), 3.06(1H, d), 3.32(1H, dd), 3.50(3H, q), 3.55(2H, t), 4.41(2H, t), 5.00–5.15(2H, m), 5.88–6.05(1H, m), 7.45(1H, d) and 7.78–7.90(2H, m).

The compound of formula 2 (Z=trifluoromethylsulphonyloxy) was prepared from 3-ethoxypropyl-4-allyloxybenzoate using the method described in Example 1 for the preparation of 3-(3-allyl-4-trifluoromethylsulphonyloxyphenyl)propionate.

3-Ethoxypropyl-4-allyloxybenzoate was prepared as described in Example 32 but using 3-ethoxy-1-propanol instead of 2-methoxyethanol. The product was an oil; NMR (CDCl$_3$): 1.20(3H, t), 2.02(2H, quintet), 3.43–3.62(4H, m), 4.38(2H, t), 4.55–4.64(2H, m), 5.27–5.49(2H, m), 5.95–6.16 (1H, m), 6.93(2H, d), 7.98(2H, d); m/Z 265 (M+H).

EXAMPLE 49 A=allyl, B=CH$_2$CH$_2$COCH$_3$

Purified by flash chromatography on silica gel using a 80:20:3 (v/v/v) mixture of ethyl acetate/ethanol/triethylamine as eluent followed by trituration with diethyl ether to give a solid, 101–104° C., NMR: 1.2–1.4 (1H, m), 1.5–1.7 (1H, m), 1.8–2.02 (3H, m), 2.1 (3H, s), 2.6–2.8 (8H, m), 2.82–2.92 (1H, d), 3.05–3.15 (1H, d), 3.45 (2H, d), 5.05 (2H, m), 5.55 (1H, s), 5.9 (1H, m), 7.05 (2H, m) and 7.25 (2H, m).

The compound of formula 2 (Z=trifluoromethylsulphonyloxy) was prepared in a similar manner to the compound of formula 2 described in Example 1. Thus, the process described in Example 1 was used to convert 4-(4-hydroxyphenyl)-2-butanone to 4-(4-allyloxyphenyl)-2-butanone which was obtained in 79% yield as an oil; NMR: 2.1 (3H, s), 2.7 (2H, m), 2.85 (2H, m), 4.5 (2H, m), 5.25 (1H, m), 5.4 (1H, m), 6.0 (1H, m), 6.85 (2H, m) and 7.05 (2H, m).

In a similar manner to that described in Example 1, 4-(4-hydroxyphenyl)-2-butanone was converted to 4-(3-allyl-4-hydroxyphenyl)-2-butanone which was obtained as an oil; NMR: 2.05 (3H, s), 2.65 (4H, m), 3.25 (2H, d), 5.0 (2H, m), 5.9 (1H, m), 6.65 (1H, d), 6.8 (2H, m) and 9.05 (1H, s).

In a similar manner to that described in Example 1, 4-(4-hydroxyphenyl)-2-butanone was converted to 4-(3-allyl-4-trifluoro-methylsulphonyloxyphenyl)-2-butanone in 80% yield, NMR: 2.15 (3H, s), 2.75 (2H, m), 2.9 (2H, m), 3.45 (2H, d), 5.1 (2H, m), 5.9 (1H, m), 7.15 (3H, m). m/z 337 (M+H).

EXAMPLE 50 A=allyl, B=CO(CH$_2$)$_2$CO$_2$Et

Purified by flash chromatography on silica gel using a 80:20:3 (v/v/v) mixture of ethyl acetate/ethanol/triethylamine as eluent to give an oil, NMR: 1.18 (3H, t), 1.2–1.4 (1H, m), 1.5–1.7 (1H, m), 1.8–2.02 (3H, m), 2.6–2.8 (4H, m), 2.82–2.92 (1H, d), 3.05–3.15 (1H, d), 3.22 (2H, m), 3.3 (2H, m), 3.6 (2H, d), 4.15 (2H, q), 5.1 (2H, m), 5.75 (1H, s), 6.0 (1H, m), 7.5 (1H, d) and 7.8 (2H, d).

The compound of formula 2 (Z=trifluoromethylsulphonyloxy) used as starting material was obtained as follows.

Sulphuric acid (98%, 1.0 ml) was added, dropwise, to a stirred solution of 4-(4-hydroxyphenyl)-4-oxo-butyric acid (5.0 g), in ethanol (50 ml). The resulting solution was then heated at 50° C. for 18 hours. The solvent was evaporated and the residue was dissolved in ethyl acetate. The mixture was washed with saturated aqueous sodium bicarbonate solution, water, dried ($MgSO_4$) and evaporated to give ethyl 4-(4-hydroxyphenyl)-4-oxo butyrate as a solid (5.3 g), NMR: 1.15 (3H, t), 2.6 (2H, t), 3.2 (2H, t), 4.15 (2H, q), 6.85 (2H, m), 7.85 (2H, m) and 10.27 (1H, s).

Using a similar procedure to Example 1 but using ethyl 4-(4-hydroxyphenyl)-4-oxobutyrate there was thus obtained ethyl 4-(4-allyloxyphenyl)-4-oxobutyate (90% yield) as an oil; NMR [$CDCl_3$]: 1.1 (3H, t), 2.65 (2H, t), 3.2 (2H, t), 4.15 (2H, q), 4.55 (2H, m), 5.3 (2H, m), 6.0 (1H, m), 6.9 (2H, m) and 7.9 (2H, m).

Using a similar procedure as example 1 but using the above as starting material there was thus obtained ethyl 4-(3-allyl-4-hydroxy-phenyl)-4-oxobutyrate (25% yield) as a solid; NMR: 1.18 (3H, t), 2.55 (2H, t), 3.15 (2H, t), 3.35 (2H, m), 4.15 (2H, q), 5.05 (2H, m), 5.9 (1H, m), 6.9 (1H, m), 7.7 (2H, m) and 10.3 (1H, s).

Using a similar procedure as example 1 but using the above as starting material there was obtained ethyl 4-(3-allyl-4-trifluoromethylsulphonyloxyphenyl)-4-oxobutyrate (85% yield) after purification (column chromatography on silica using 50% ethyl acetate/pentane as eluent) as an oil; NMR: 1.15 (3H, t), 2.65 (2H, t), 3.32 (2H, m), 3.55 (2H, m), 4.07 (2H, q), 5.18 (2H, m), 5.95 (1H, m), 7.58 (1H, m), 8.05 (2H, m).

EXAMPLE 51 A=allyl, B=$COCH_2CO_2Et$

Purified by flash chromatograph on silica gel using a 80:20:2 (v/v/v) mixture of ethyl acetate/ethanol/triethylamine as eluent to give an oil, NMR: 1.2 (3H, t), 1.2–1.4 (1H, m), 1.5–1.7 (1H, m), 1.8–2.02 (3H, m), 2.6–2.8 (4H, m), 2.82–2.92 (1H, d), 3.05–3.15 (1H, d), 3.55 (2H, d), 4.15 (4H, m), 5.1 (2H, m), 5.75 (1H, s), 6.0 (1H, m), 7.5 (1H, m) and 7.75 (2H, m).

The compound of formula 2 (Z=trifluoromethylsulphonyloxy) used as starting material was obtained as follows:

Diethyl carbonate (50 ml) was heated to reflux, under an atmosphere of argon. The heat source was removed and freshly prepared sodium (3 g) was added over a period of 20 minutes. The reaction temperature was raised to reflux and a hot solution of 3-allyl-4-hydroxyacetoxyphenone (7.8 g) in diethyl carbonate (80 ml) was added.

Ethanol produced (about 15 ml) during the reaction was removed at the elevated temperature of the reaction mixture together with some diethyl carbonate. Diethyl carbonate (150 ml) was then added to the reaction mixture and the reaction mixture heated at reflux for 2.5 hours.

The reaction mixture was cooled to 30° C. and ice water (50 ml) was added cautiously. The mixture was carefully neutralized by addition of 3M aqueous hydrochloric acid (~40 ml) and the aqueous mixture was extracted with diethyl ether (3×50 ml). The organic extracts were combined, dried ($MgSO_4$) and evaporated to give an oil, which was purified using dry flash chromatography on 60H silica (Merck Art. No. 7736) using a mixture of ethyl acetate and toluene as eluent to give ethyl 4-(3-allyl-4-hydroxyphenyl)-3-oxo-propionate (7.2 g), NMR [$CDCl_3$]: 1.2 (3H, t), 3.4 (2H, d), 3.95 (2H, s), 4.2 (2H, q), 5.1 (2H, m), 6.0 (1H, m), 6.85 (1H, m) and 7.7 (2H, m); m/z=249 (M+H).

In an alternative procedure, triethylamine (0.28 ml) was added to an ice cooled solution of ethyl 4-(3-allyl-4-hydroxyphenyl)-3-oxo-propionate (0.5 g), in dichloromethane (10 ml). The reaction mixture was stirred for 5 minutes and trifluoromethane sulphonic anhydride (0.34 ml) was then added in a dropwise manner. The reaction mixture was stirred for 15 minutes.

The reaction mixture was diluted with dichloromethane (20 ml), washed with water (10 ml), brine (10 ml), dried ($MgSO_4$) and evaporated to give an oil which was purified by flash chromatography on silica gel using toluene as eluent, to give a colourless oil (0.7 g). m/z=381 (M+H).

EXAMPLE 52 A=H, B=$CH_2CH_2CN$

Purified by flash chromatography on silica gel using a 80:20:2 (v/v/v) mixture of ethyl acetate/ethanol/triethylamine as eluent to give a solid (0.13 g), NMR: 1.2–1.4 (1H, m), 1.5–1.7 (1H, m), 1.8–2.02 (3H, m), 2.6–2.8 (4H, m), 2.75 (2H, m), 2.85 (2H, m), 2.82–2.92 (1H, d), 3.05–3.15 (1H, d), 7.25 (2H, d) and 7.33 (2H, m).

The compound of formula 2 (Z=trifluoromethylsulphonyloxy) used as starting material was prepared as follows:

Using a similar procedure to Example 1, but using 3-(4-hydroxyphenyl)propionitrile (0.8 g), as the starting material, was thus obtained 3-(4-trifluoromethylsulphonyloxyphenyl) propionitrile (1 g); NMR: 2.85 (2H, m), 2.95 (2H, m), 7.5 (4, m); m/z=297 (M+$NH_4$).

EXAMPLE 53 A=$CH_2CO_2CH_2CH_2CH_3$, B=H

Obtained as a gum, NMR: 0.9(3H, t), 1.4(1H, m), 1.5–1.7 (3H, m), 1.8–2.0(3H, m), 2.7(4H, m), 2.9(1H, d), 3.1(1H, d), 3.8(2H, s), 4.0(2H, t), 5.7(1H, s), 7.2–7.4(4H, m).

The starting material of formula 2 (Z=iodo) was prepared in a similar manner to the compound of formula 2 described in Example 54 except propan-1-ol (0.16 ml) was substituted for propan-2-ol. There was thus obtained propyl 2-(2-iodophenyl)acetate (232 mg) as a yellow oil; NMR: 0.9(3H, t), 1.6(2H, m), 3.8(2H, s), 4.0(2H, t), 7.0(1H, m), 7.4(2H, m), 7.9(1H, d).

EXAMPLE 54 A=$CH_2CO_2CHMe_2$, B=H

Purified by chromatography on silica gel (Varian Bond Elut S1 silica gel) using a gradient of methanol in dichloromethane containing 1% ammonia (density 0.88 g/cm³) as eluent to give a gum, NMR: 1.2(6H, d), 1.3(1H, m), 1.6(1H, m), 1.8–2.0(3H, m), 2.7(4H, m), 2.9(1H, d), 3.1(1H, d), 3.8(2H, s), 4.9(1H, m), 5.6(1H, s), 7.2–7.4(4H, m).

The compound of formula 2 (Z=iodo) used as starting material was prepared as follows.

A solution of 2-(2-iodophenyl)acetic acid (0.50 g) and propan-2-ol (0.142 ml) in dry dimethylformamide (10 ml) was treated with 1-(3-dimethylaminopropyl)-3-ethylcarbodiimide hydrochloride (0.458 g) with stirring at ambient temperature under an atmosphere of argon. After 18 hours the reaction mixture was diluted with ethyl acetate (50 ml) and washed with water (3×50 ml) and brine. The aqueous layers were back-extracted with ethyl acetate (50 ml) and the organic layers were combined, dried ($MgSO_4$) and evaporated. The residue was purified by chromatography on silica gel (Varian Band Elut S1 silica gel) eluting with dichloromethane to give 2-propyl 2-(2-iodophenyl) acetate (232 mg) as a yellow oil, NMR: 1.2(6H, d), 3.8(2H, s), 4.9(1H, m), 7.0(1H, m), 7.4(2H, d) and 7.85(1H, d).

EXAMPLE 55 A=allyl, B=$CH_2CH(CH_3)CO_2CH_3$

Purified by column chromatography on alumina (Fluka 507C Neutral) using a 19:1 (v/v) mixture of ethyl acetate and methanol as eluent to give an oil; NMR(CDCl$_3$): 1.12(3H,d), 1.40–1.55(1H,m), 1.57–1.75(1H,m), 1.90–2.15(3H,m), 2.30 (1H,bs), 2.57–2.76(2H,m), 2.78–3.02(5H,m), 3.06(1H,d), 3.31(1H,d.d), 3.49(2H,d), 3.62(3H,s), 4.98–5.11(2H,m), 5.87–6.02(1H,m), 6.97(2H,m) and 7.32(1H,d): m/z 368(M+H).

The compound of formula 2 (Z=trifluoromethylsulphonyloxy) was prepared as follows.

A solution of methyl trans 2-methyl-3-(4-hydroxyphenyl) cinnamate (2.79 g) (JAm Chem. Soc. 72, 2619, 1950) in ethyl acetate (55 ml) was hydrogenated at ambient temperature/atmospheric pressure over a 10% palladium/carbon catalyst. The catalyst was removed by filtration and the filtrate was evaporated. The residue was purified by flash-column chromatography on silica gel using a 7:3(v/v) mixture of hexane and ethyl acetate as eluent to give methyl 2-methyl-3-(4-hydroxyphenyl)propionate (2.45 g) as a colourless oil: NMR(CDCl$_3$): 1.15(3H,d), 2.63(2H,m), 2.92 (1H,q), 3.60(3H,s), 5.05(1H,bs), 6.71(2H,d) and 7.00(2H,d).

Methyl 2-methyl-3-(4-allyloxyphenyl)propionate m/z 235(M+H) was prepared from methyl 2-methyl-3-(4-hydroxyphenylpropionate using the method described in Example 1 for the preparation of ethyl 3-(4-allyloxyphenyl) propionate. Methyl 2-methyl-3-(3-allyl-4-hydroxyphenyl) propionate was prepared from methyl 2-methyl-3-(4-allyloxyphenyl)propionate using the method described in Example 1 for the preparation of ethyl 3-(3-allyl-4-hydroxyphenyl)propionate. The product was isolated as an orange oil; NMR(CDCl$_3$): 1.13(3H,d), 2.40–2.73(2H,m), 2.92(1H,q), 3.37(2H,d), 3.63(3H,s), 4.91(1H,s), 5.03–5.18 (2H,m), 5.89–6.10(1H,m), 6.70(1H,m) and 6.91(2H,m); m/z 235(M+H).

The method described in Example 1 for the preparation of ethyl 3-(3-allyl-4-trifluoromethylsulphonyloxyphenyl) propionate was used to convert methyl 2-methyl-3-(3-allyl-4-hydroxyphenyl)propionate to methyl 2-methyl-3-(3-allyl-4-trifluoromethylsulphonyloxyphenyl)propionate: NMR (CDCl$_3$) 1.18(3H,d), 2.70(2H,m), 3.01(1H,m), 3.42(2H,d), 3.62(3H,s), 5.13(2H,m), 5.90(1H,m), 7.08(2H,m) and 7.16 (1H,d), m/z 366(M+H).

EXAMPLE 56 A=allyl, B= CH$_2$CH$_2$CO$_2$CH$_2$CH$_2$OCH$_3$

Purified flash chromatography on silica gel using a 19:1 (v/v) mixture of ethyl acetate and methanol as eluent to give a solid, m.p. 70–72° C.; NMR(CDCl$_3$): 1.37–1.52(1H,m), 1.60–1.78(1H,m), 1.93–2.18(3H,m), 2.62(2H,t), 2.76–2.98 (6H,m), 3.02–3.17(1H,m), 3.28–3.41(4H, m+s), 3.45–3.60 (4H,m), 4.21(2H,m), 4.98–5.10(2H,m), 5.88–6.02(1H,m), 6.98–7.06(2H,m) and 7.32(1H,d), m/z 398(M+H).

The compound of formula 2 (Z=trifluoromethylsulphenyloxy), was prepared as follows.

3-Allyl-4-hydroxyphenyl propionic acid (1.1 g) was treated with 2-methoxyethanol (10 ml) containing concentrated sulphuric acid (0.1 ml) for 5 hours at 100° C. The methoxyethanol was evaporated and the residue treated with saturated sodium bicarbonate (25 ml). The aqueous mixture was extracted with ether (3×25 ml). The ether extracts were combined, washed with saturated brine (1×25 ml), dried (MgSO$_4$) and evaporated. The residual oil was purified by flash column chromatography on silica gel using a 4:1 (v/v) mixture of hexane and ethyl acetate to give methoxyethyl 3-(3-allyl-4-hydroxyphenyl)propionate (915 mg) as a pale yellow oil; NMR(CDCl$_3$): 2.61(2H,t), 2.87(2H,t), 3.38(3H, s), 3.57(2H,t), 4.21(2H,t), 4.98(1H,s), 5.08–5.18(2H,m), 5.92–6.08(1H,m), 6.71(1H,m) and 6.93(2H,m): m/z 265(M+H).

The triflate was prepared as in Example 1 using methoxyethyl 3-(3-allyl-4-hydroxyphenyl)propionate in place of ethyl 3-(3-allyl-4-hydroxyphenyl)propionate.

Methoxyethyl 3-(3-allyl-4-trifluoromethylsulphonyloxyphenyl)propionate was obtained as an oil; NMR(CDCl$_3$) 2.65(2H,t), 2.93(2H,t), 3.38(3H,s), 3.95(2H,d), 3.57(2H,m), 4.21(2H,m), 5.07–5.20 (2H,m), 5.82–5.98(1H,m) and 7.15(3H,m).

EXAMPLE 57 A=allyl, B=CH$_2$OCH$_2$CO$_2$Me

Obtained as an oil, NMR(CDCl$_3$): 1.33–1.50(1H,m), 1.57–1.75(1H,m), 1.95–2.15(3H,m), 2.25–2.60(1H,m, exchangeable) 2.74–3.00(4H,m), 3.08(2H,d), 3.32(1H,d.d), 3.52(2H,d), 3.75(3H,s), 4.10(2H,s), 4.60(2H,s), 5.06(2H,m), 5.95(1H,m), 7.18(2H,m) and, 7.38(1H,d); m/z 370(M+H).

The compound of formula 2 (Z=trifluoromethylsulphonyloxy), methyl 3-(3-allyl-4-trifluoromethylsulphonyloxyphenyl)methyloxyacetate, was prepared as follows. Allyl bromide (4.4 g) was added to a stirred suspension of 4-hydroxybenzyl alcohol (4.34 g) and potassium carbonate (5.00 g) in butanone (40 ml). The reaction mixture was heated at reflux for 18 hours. The reaction mixture was cooled and then filtered. The filtrate was evaporated to give an oil which was purifed by flash column chromatography on silica gel using a 4:1 (v/v) mixture of hexane and ethyl acetate as eluent to give 4-allyloxybenzyl alcohol (4.50 g) as a pale yellow oil; NMR(CDCl$_3$): 1.81(1H,t), 4.48–4.65(4H,m), 5.22–5.48(2H, m), 6.05(1H,m), 6.90(2H,m) and 7.25(2H,m), m/z 164(H).

Sodium hydride (1.20 g; 60% dispersion in oil) was added over a period of 10 minutes to a stirred solution of 4-allyloxybenzyl alcohol (4.60 g) in DHF (20 ml) at 0° C. under an atmosphere of argon. After 0.5 hours, a solution of methylchloroacetate (3.30 g) in DMF (10 ml) was added over a period of 0.25 hours. The reaction mixture was stirred for 40 hours at ambient temperature. Water (300 ml) was added and the mixture extracted with ethyl acetate (3×100 ml). The ethyl acetate extracts were combined, washed with brine (2×100 ml), dried (MgSO$_4$) and evaporated. The residue was purified by flash column chromatography on silica gel using a 9:1 (v/v) mixture of hexane/ethyl acetate to give 4-allyloxyphenylmethyloxy acetate (2.42 g) as a colourless oil; NMR(CDCl$_3$): 3.75(3H,s), 4.07(2H,s), 4.52 (4H,m), 5.36(2H,m), 6.10(1H,m), 6.88(2H,m) and 7.28(2H, m); m/z 236(H).

A mixture of methyl 4-allyloxyphenylmethyloxyacetate (2.00 g) and diphenyl ether (14 ml) was heated at 200° C. in an atmosphere of argon for 9 hours. The mixture was cooled to ambient temperature and purified by flash column chromatography on silica gel using a 4:1 (v/v) mixture of hexane and ethyl acetate as eluent to give methyl (3-allyl-4-hydroxyphenyl)methyloxyacetate (435 mg) as a colourless oil; NMR(CDCl$_3$): 3.38(2H,d), 3.75(3H,s), 4.07(2H,s), 4.52 (2H,s), 5.12(2H,m), 6.00(1H,m), 6.78(1H,m) and 7.08(2H, m); m/z 236(M).

Trifluoromethane sulphonic anhydride (0.33 ml) was added over a period of 0.1 hours to a stirred solution of the above phenol (414 mg) in pyridine (2 ml) at 0° C. under an atmosphere of argon. After 18 hours, water (30 ml) was added. The aqueous phase was extracted with ethyl acetate (3×20 ml). The ethyl acetate extracts were combined, washed with 1M aqueous hydrochloric acid (3×20 ml), brine (2×30 ml), dried (MgSO$_4$) and evaporated. The residue was purified by flash column chromatography on silica gel using a 19:1 (v/v) mixture of hexane and ethyl acetate as eluent to give methyl 3-(3-allyl-4- trifluoromethylsulphonyloxyphenyl)methyl oxyacetate (437 mg) as a colourless oil; NMR(CDCl$_3$): 3.45(2H,d), 3.78(3H, s), 4.12(2H,s), 4.60(2H,s), 5.14(2H,m), 5.90(1H,m) and 7.27(3H,m).

EXAMPLE 58 A=allyl, B=CH$_2$CH$_2$CON(Et)$_2$

Purified by flash chromatography on silica gel using a 90:9:1 (v/v/v) mixture of ethyl acetate/methanol/ammonia as eluent to give an oil; NMR(CDCl$_3$): 1.10(6H,t), 1.33–1.52(1H,m), 1.52–1.72(1H,m), 1.92–2.16(3H,m), 2.55 (2H,m), 2.75–3.03(7H,m), 3.08–3.42(5H,m), 3.50(2H,d), 4.97–5.11(2H,m), 5.85–6.05(1H,m), 7.02(2H,m) and 7.32 (1H,d), m/z 395(M+H).

The compound of formula 2 (Z=trifluoromethylsulphonyloxy), N,N-diethyl 3-(3-allyl-4-trifluromethylsulphonyloxyphenyl)propionamide, used as starting was prepared from N,N-diethyl 3-(4-hydroxyphenyl)propionamide using the procedure described in Example 1 for the preparation of ethyl 3-(3-allyl-4-trifluoromethylsulphonyloxyphenyl)propionate via the following intermediates
a) N,N-diethyl 3-(4-allyloxyphenyl)propionamide, a colourless oil; NMR(CDCl$_3$): 1.10(5H,m), 2.53(2H,m), 2.90 (2H,m), 3.22(2H,q), 3.37(2H,q), 4.51(2H,d,t), 5.23–5.47 (2H,m), 5.95–6.15(1H,m), 6.83(2H,m) and 7.12(2H,m), m/z 262(M+H).
b) N,N-diethyl 3-(3-allyl-4-hydroxyphenyl)propionamide, a pale yellow oil; NMR(CDCl$_3$): 1.10(6H, m), 2.55(2H,m), 2.88(2H,m), 3.22(2H,q), 3.38(4H,q), 5.06–5.20(2H,m), 5.61(1H,br.d), 5.90–6.10(1H,m), 6.75(1H,m) and 6.97 (2H,m), m/z 262(M+H).
c) N,N-diethyl 3-(3-allyl-4-trifluoromethyl sulphonyloxyphenyl)propionamide, a pale yellow oil; m/z 394(M+H).

EXAMPLE 59 A=CH$_2$OCH$_2$C≡CCH$_3$, B=H

Purified by chromatography on silica gel (Varian Bond Elut S1 silica gel) using a gradient of 0 to 5% methanol in dichloromethanol as eluent to give a gum, NMR(CDCl$_3$): 1.45(1H,m), 1.7(1H,m), 1.88(3H,t), 2.09(3H,m), 2.88(4H, m), 3.1(1H,d), 3.35(1H,d), 4.2(2H,q), 4.7(2H,s), 7.3(2H,m) and 7.42(2H,t); m/z 310 (M+H).

The compound of formula 2 (Z=iodo) used as starting material was prepared in a similar manner to the compound of formula 2 described in Example 60 but using 2-iodobenzyl chloride in place of 2-iodobenzyl alcohol and 2-butyn-1-ol in place of allyl bromide. The reaction mixture was used without purification.

EXAMPLE 60 A=CH$_2$OCH$_2$CH=CH$_2$, B=H

Purified by chromatography on silica gel (Varian Bond Elut S1 silica gel) using a gradient of 0 to 5% methanol in dichloromethane as eluent to give a gum, NMR(CDCl$_3$): 1.5(1H,m), 1.72(1H,m), 2.12(3H,m), 2.9(4H,t), 3.05(2H,m), 3.15(1H,d), 3.38(1H,d), 4.05(2H,m), 4.62(2H,s), 5.25(2H, m), 5.95(1H,m), 7.22(1H,t), 7.35(1H,t), 7.45(2H,q); m/z 298(M+H).

The compound of formula 2 (Z=iodo) was prepared as follows.

Sodium hydride (220 mg of 60% dispersion in mineral oil) was added to a stirred solution of 2-iodobenzylalcohol (1.17 g) in dimethylformamide under an atmosphere of argon. Allyl bromide (520 μl) was added to the stirred suspension and the mixture was stirred at ambient temperature for 16 hours and then heated at 60° C. for 2 hours. The mixture was used without purification.

EXAMPLE 61 A=CH$_2$OCH$_2$CH$_3$, B=H

Purifed by chromatography on silica gel (Varian Bond Elut S1 silica gel) using a gradient of 0 to 5% methanol in dichloromethane as eluent to give a gum, NMR(CDCl$_3$): 1.25(3H,t), 1.45(1H,m), 1.7(1H,m), 2.08(3H,m), 2.85(4H,t), 3.1(1H,d), 3.33(1H,d), 3.59(2H,q), 4.65(2H,s), 7.2(1H,t), 7.32(1H,t), 7.42(2H,q); m/z 286 (M+H)

The compound of formula 2 (Z=iodo) was prepared using the procedure described in Example 60 for the compound of formula 2 but using ethyl iodide in place of allyl bromide.

The reaction mixture was used without purification.

EXAMPLE 62 A=CH$_2$OCOCH$_2$CH$_3$, B=H

Purified by chromatography on silica gel (Varian Bond Elut S1 silica gel) using a 0 to 5% gradient of methanol in dichloroethane as eluent to give a gum; NMR(CDCl$_3$): 1.16(3H,t), 1.45(1H,m), 1.69(1H,m), 2.0(3H,m), 2.4(2H,q), 2.87(4H,m), 3.07(1H,d), 3.84(1H d of d), 5.27(2H,d), 7.25–7.45(4H,m). m/z 314 (M+H).

The compound of formula 2 (Z=iodo) was prepared as follows.

Propionyl chloride (505 mg) was added to a stirred solution of 2-iodobenzyl alcohol (1.17 g) and pyridine (474 mg) in dichloromethane (10 ml). The mixture was stirred at ambient temperature for 16 hours. The reaction mixture was evaporated and dimethylformamide (15 ml) was added to the residue. The mixture was used without purification.

EXAMPLE 63 A=CO$_2$CH(Me)Et, B= OCH$_2$CH$_2$OCH$_3$

Purified by chromatography on silica gel (Varian Bond Elut S1 silica gel) using a 0 to 10% gradient of methanol in dichloromethane to give on oil; NMR(CDCl$_3$): 0.91(3H,t), 1.30(3H,d), 1.4–1.8(2H,m), 1.92(1H,m), 2.67(2H,t), 2.83 (1H,d), 3.10(1H,d), 3.68(2H,m), 4.15(2H,m), 4.95(1H,m), 7.15(1H d of d), 7.18(1H,d), 7.43(1H,d); m/z 4102 (M+H).

The compound of formula 2 (Z=trifluoromethylsulphonoxy) used as starting material was prepared in a similar manner to that described in Example 64 but sec-butanol was used in place of ethanol. The compound of formula 2 was obtained as an oil; NMR: 0.90(3H,t), 1.30(3H,d), 1.70(2H,m), 3.3(3H,s), 3.67(2H,m), 4.2(2H,m), 5.02(1H,m), 7.35(1H d of d), 7.48(2H,m); m/z 400(M) via the corresponding phenol; NMR: 0.92(3H,t), 1.32(3H,d), 1.7(2H,m), 3.62(2H,m), 4.05(2H,m), 5.05(1H, m), 6.92(1H,d), 7.2(1H d of d), 7.28(1H,d), 10.2(1H,s); m/z 268(M).

EXAMPLE 64 A=CO$_2$Et, B=OCH$_2$CH$_2$OCH$_3$

Purified by trituration with acetonitrile and diethyl ether to give a solid, m.p. 153.5–154.5° C.; NMR(CDCl$_3$): 1.38 (3H,t), 1.64(1H,m), 1.5–1.4(1H,m), 1.8–1.95(1H, broad) 2.08(3H,m), 2.65(4H,m), 3.33(1H,d), 3.04(1H,d), 3.45(3H, s), 3.75(2H,m), 4.15(2H,m), 4.35(2H,q), 7.0(1H, d of d) and 7.42(2H,m).

The compound of formula 2 (Z=trifluoromethylsulphonyloxy) was prepared as follows.

Sodium chlorite (8.08 g) was added over a period of 30 seconds to a stirred solution 2-hydroxy-5-(2-methoxyethoxy)benzaldehyde (see Example 41) and sodium methoxide in methanol (25% by weight solution, 9.68 ml) in dimethylsulphoxide (350 ml) at 15° C. After warming to room temperature and stirring for 3 hours the mixture was added to water (600 mls), acidified with 2M aqueous hydrochloric acid, and extracted with diethyl ether (4×250 mls). The ethereal extracts were combined, washed with water (2×100 ml), dried (MgSO$_4$) and evaporated. The residue was crystallised from toluene to give 2-hydroxy-5-(2-methoxyethoxy)benzoic acid (4.1 g) as solid m.p. 115–116° C.; NMR 3.3(3H,s), 3.65(2H,m), 4.05(2H,m), 6.9(1H,d), 7.15(1H, d of d), 7.25(1H,d); m/z 213(M+H).

Concentrated sulphuric acid (0.5 ml) was added to a stirred solution of 2-hydroxy-5-(2-methoxyethoxy)benzoic acid (2 g) in ethanol (50 ml). The mixture was heated at reflux for 12 hours. The reaction mixture was added to sodium hydrogen carbonate solution (5% by weight in water, 200 ml) and the aqueous mixture was extracted with ethyl acetate (4×50 ml). The organic extracts were combined, washed with water (50 ml), brine, (50 ml), dried (MgSO$_4$) and evaporated to give 2-ethoxycarbonyl-4-(2-methoxyethoxy)phenol (1.85 g) as an oil; NMR: 1.35(3H,t), 3.31(3H,s), 3.6(2H,m), 4.0(2H,m), 4.3(2H,q), 6.9(1H,d), 7.18(1H d of d), 7.2(1H,d); m/z 241(MH). This was converted into the trifluoromethane sulphonate ester using an analogous procedure to that described in Example 1 for the preparation of ethyl 3-(3-allyl-4-trifluoromethylsulphonyloxy)propionate. There was thus obtained after chromatography on silica gel (Varian bond elut S1 silica gel) using a gradient of 5 to 25% ethyl acetate in hexane as eluent as an oil; NMR($_6$): 1.3(3H,t), 3.3(3H,s), 3.62(2H,m), 4.2(2H,m), 4.34(2H,q), 7.35(1H, d of d), 7.49 (2H,m); m/z 373(M+H).

EXAMPLE 65

Using the procedure described in Example 1 but using (−)-3-ethynyl-3-hydroxyquinuclidine in place of 3-ethynyl-3-hydroxyquinuclidine there was obtained (−)-3-[2-(2-allyl-4-(2-ethoxycarbonylethyl)phenyl)ethynyl]quinuclidin3-ol as an oil.

The (−)-3-ethynyl-3-hydroxyquinuclidine used as starting material was prepared as follows.

A solution of (±)-3-ethynyl-3-butyryloxy quinuclidine (4.42 g) in deionised water (700 ml) containing methanol (35 ml) was adjusted to pH 7.0 using 0.1M aqueous sodium hydroxide solution (dispensed by a pH autotitrator). A suspension of pig liver esterase (3.0 ml, 3450 units, in 3.2M aqueous ammonium sulphate solution at pH 8; Sigma Chemical Company Ltd) was added to the reaction mixture and the mixture stirred at ambient temperature for 46 hours whilst maintaining the pH at 7.0 using 0.1M aqueous sodium hyroxide solution (dispensed from a pH autotitrater). During this period 112.5 ml of the sodium hydroxide solution was consumed, indicating that the hydrolysis was 56% complete. The pH of the reaction mixture was adjusted to 2.52 using 2M aqueous hydrochloric acid and the mixture stirred for 20 minutes. 2M aqueous sodium hydroxide solution was added to the mixture to give a pH of 7.01 and the mixture extracted with diethyl ether (12×150 ml). The diethyl ether extracts were combined, dried (MgSO$_4$) and evaporated to give an oil (2.43 g) containing (−)-3-ethynyl-3-butyryloxyquinuclidine and some butyric acid.

The above oil containing(−)-3-ethynyl-3-butyryloxyquinuclidine was treated with a solution of potassium hydroxide (2.24 g) in methanol (50 ml). The mixture was stirred at ambient temperature for 2 hours. The mixture was evaporated and deionised water (2 ml) was added to the residue to give a solid. The solid was collected by filtration, washed with water (2×2 ml) and dried under vacuum over phosporus pentoxide to give (−)-3-ethynyl-3-hydroxyquinuclidine (611 mg) as a solid, m.p. 199–202° C., $[\alpha]^{19}_D$=−56.1° (C=1.02, methanol).

EXAMPLE 66

Using the procedure described in Example 1 but using (+)-3-ethynyl-3-hydroxyquinuclidine in place of 3-ethynyl-3-hydroxyquinuclidine there was obtained (+)-3-[2-(2-allyl-4 (2-ethoxycarbonylethyl)phenyl)ethynyl]quinuclidin-3-ol as an oil, $[\alpha]^{25}D$=+21.8 (C=0.316, ethanol).

The (+)-3-ethynyl-3-hydroxyquinuclidine was prepared as follows.

A solution of (±)-3-ethynyl-3-butyryloxyquinuclidine (4.42 g) in deionised water (700 ml) containing methanol (35 ml) was adjusted to pH 7.0 using an 0.1M aqueous sodium hydroxide solution (dispensed by a pH autotitrater). A suspension of pig liver esterase (8.0 ml, 9200 units,in 3.2M aqueous ammonium sulphate solution at pH 8; S1 gma Chemical Company Ltd) was added to the reaction mixture and the mixture was stirred at ambient temperature whilst maintaining the pH at 7.0 using 0.1M aqueous sodium hydroxide solution (dispensed by a pH autotitrater). After 5.5 hours, 7.3 ml of the sodium hydroxide solution had been consumed, indicating that the hydrolysis was 35% complete. The pH of the reaction mixture was adjusted to 2.5 using 2H aqueous hydrochloric acid and the mixture was stirred for 10 minutes. 2M aqueous sodium hydroxide solution was then added to the mixture to give a pH of 7.05 and the mixture extracted with diethyl ether (3×200 ml, followed by 12×150 ml). The aqueous phase was separated, and freeze dried over a period of 48 hours to give a solid which was dissolved in deionised water (30 ml). The solution was filtered and the filtrate was basified to pH 9 using 10.8M sodium hydroxide solution to give a solid. The solid was collected by filtration to give (+)-3-ethynyl-3-hydroxyquinuclidine, (554 mg), m.p. 204–207° C., $[\alpha]^{20}_D$=+54.5° (C=0.99, methanol).

The (±)-3-ethynyl-3-butyryloxyquinuclidine used as starting material was prepared as follows.

A solution of n-butyl lithium (100 ml of a 2M solution in pentane) was added portion-vise over a period of 20 minutes to a stirred solution of ethynyltrimethylsilane (19.6 g) in dry tetrahydrofuran (400 ml) at −70° C. The mixture was stirred for 1 hour at −70° C. A solution of 3-quinuclidinone (2.4 g) in dry tetrahydrofuran (100 ml) was then added and the mixture stirred for 1 hour at −70° C. Methanol (1 ml) was then added to the mixture and the mixture allowed to warm to ambient temperature. The solvents were removed by evaporation. Methanol (500 ml) and potassium carbonate (40 g) were added to the residue and the mixture was stirred for 1 hour. The solvent was removed by evaporation. The residue was triturated with water (500 ml) and then dried in vacuo to give 3-ethynyl-3-hydroxy-quinuclidine as a solid, m.p. 193–197° C.; NMR(DMSO-d$_6$): 1.5–1.3(1H,m), 1.4–1.6(1H,m), 1.7–1.95(3H,m), 2.55–2.8(5H,m), 2.95(1H, d), 3.3(1H,d) and 5.4(1H,s); m/z 152 (M+H).

A mixture of (±)-3-ethynyl-3-hydroxyquinuclidine (15.1 g) and butyric anhydride (60 ml) was stirred at 120° C. for 5 hours. The reaction mixture was cooled to ambient temperature, added to a saturated aqueous solution of sodium carbonate (11) and stirred for 3 hours. The mixture was extracted with diethyl ether (3×10 ml). The diethyl ether extracts were combined, washed with saturated aqueous sodium carbonate solution, dried (MgSO$_4$) and evaporated to give (±)-3-ethynyl-3-butyryloxyquinuclidine as an oil, NMR(200 MHz, DMSOd$_6$): 0.90(3H,t), 1.40(1H,m), 1.57 (4H,m), 1.85(1H,m), 2.28(3H,m), 2.66(4H,m),.3.03(1H,d), 3.18(1H,d) and 3.55(1H,s).

EXAMPLE 67

3-[2-[2-allyl-4-(2-ethoxycarbonylethyl)-phenyl]ethynyl]quinuclidin-3-ol (300 mg) was added to a stirred solution of sodium hydroxide pellets (150 mg) in a mixture of ethanol (6 ml) and water (3 ml) at ambient temperature. After 15 hours, the solution was filtered and the filtrate was evaporated. The residue was stirred with water (5 ml) and 1M aqueous hydrochloric acid (6 ml) was then added. The mixture was evaporated and the residue azeotroped with toluene (2×10 ml). The residue was treated with dry acetone (10 ml) and filtered. The insoluble residue was washed with acetone (5 ml). The filtrate and washings were combined, evaporated and the residue triturated with ether. Evaporation of the ether gave 3-[2-[2-allyl-4-(2-carboxyethyl)-phenyl)ethynyl]quinuclidin-3-ol hydrochloride salt as a solid (247 mg), m.p. 41.4° C. (dec), NMR([$CD_3$]$_2$SO/$CD_3COOD$): 1.60–1.88(1H,m), 1.92–2.10(2H,m), 2.10–2.40(3H,m), 2.52 (2H,t), 2.84(2H,t), 3.10–3.60(8H,m), 5.08(2H,m), 5.98(1H, m), 7.12(2H,m) and 7.37(1H,d); m/z 340(M+H).

EXAMPLE 68

Using the procedure described in Example 67 but using (+)-3-[2-allyl-4-(2-ethoxycarbonylethyl)phenyl)ethynyl] quinculidin- 3-ol as starting material, there was thus obtained (+)-3-[2-(2-allyl-4-(2-carboxyethyl)phenyl)ethynyl)quinuclidine-3-ol hydrochloride, as a solid, m.p. 161–163° C., NMR(DMSOd$_6$/$CD_3COOD$): 1.60–1.88(1H, m), 1.92–2.10(2H,m), 2.10–2.40(3H,m), 2.52(2H,t), 2.84 (2H,t), 3.10–3.60(8H,m), 5.08(2H,m), 5.98(1H,m), 7.12 (2H,m) and 7.37(1H,d); m/z 340(M+H).

EXAMPLE 69

Using the procedure described in Example 67 but using (−)-3-[2-allyl-4-(2-ethoxycarbonylethyl)phenyl)ethynyl] quinuclidin-3-ol as starting material, there was thus obtained (−)-3-[2-(2-allyl-4-(2-carboxyethyl)phenyl)ethynyl) quinuclidin-3-ol hydrochloride as a solid, 161–163° C.; NMR: 1.60–1.88(1H,m), 1.92–2.10(2H,m), 2.10–2.40(3H, m), 2.52(2H,t), 2.84(2H,t), 3.10–3.60(8H,m), 5.08(2H,m), 5.98(1H,m), 7.12(2H,m) and 7.37(1H,d), m/z 340(M+H).

EXAMPLE 70

Using the procedure described in Example 1 but using 4-(methoxycarbonylmethyl)iodobenzene as starting material in place of ethyl 3-(3-allyl-4-trifluoromethylsulphonyloxyphenyl)propionate and 3-ethenyl-3-hydroxyquinuclidine in place of 3-ethynyl-3-hydroxyquinuclidine, there was obtained, after recrystallisation from ethyl acetate, 3-[2-(4-methoxycarbonylmethoxyphenyl)vinyl]quinculdine-3-ol as a solid, m.p. 169–170° C., NMR(CDCl$_3$): 1.32–2.20(6H,s quinuclidine+OH at 1.9), 2.7–3.15(6H,m), 3.8(3H, d), 4.65 (2H,s), 6.3–6.5(2H,m), 6.84–7.38(4H,m).

EXAMPLE 71

Using a similar procedure to that described in Example 21 but using 3-(4-[2-methoxyethoxy]phenoxymethyl)-3-hydroxyquinuclidine borane complex as starting material there was obtained 3-(4-[2-methoxyethoxy]phenoxymethyl)quinuclidin-3-ol as a solid, m.p. 93–95° C., NMR: 1.5–1.8 (1H,m), 1.7–2.0(2H,m), 2.1–2.4(2H,m), 2.9–3.4(9H,m), 3.55–3.65(2H,m), 3.9–4.1(4H,m), 5.45–5.55(1H,s), 6.8–6.95(4H,s) and 10.0–10.6(1H,br).

The 3-(4-[2-methoxyethoxy]phenoxymethyl)-3-hydroxyquinuclidine borane complex used as starting material was prepared as follows.

Solid potassium carbonate (0.42 g) was added to a solution of 4-methoxyethoxyphenol (0.44 g) and 3-methylenequinuclidine oxide borane complex (0.31 g) in dry dimethylformamide (1 ml) under an atmosphere of argon. The mixture was stirred for 6 hours at 75° C. The mixture was poured into water (3 ml) and extracted with ethyl acetate (3×3 ml). The ethyl acetate extracts were combined, washed with water (4×2.5 ml), dried ($Na_2SO_4$) and evaporated. The residue was crystallised from ether to give 3-(4-[2-methoxyethoxy]phenoxymethyl)-3-hydroxyquinuclidine borane complex as a colourless solid (0.53 g), m.p. 107–109° C.; NMR(CDCl$_3$): 0.5–2.5(3H,br), 1.5–1.7(1H,m), 1.75–1.9(2H,m) 2.2–2.4(2H,m), 2.7–2.75 (1H,s), 2.8–3.25(6H,m), 3.4–3.5(3H,s), 3.7–3.8(2H,m), 3.8–4.0(2H,q), 4.05–4.15(2H,m), 6.8–6.95(4H,m).

EXAMPLE 72

Using a similar procedure to that described in Example 21 but using 3-(4-ethoxycarboxyethylphenoxymethyl)-3-hydroxyquinuclidine borane complex as starting material there was obtained 3-(4-ethoxycarboxyethylphenoxymethyl)quinuclidine-3-ol as a solid m.p. 75–77° C., NMR(DMSOd$_6$): 1.2–1.3(3H,t), 1.3–1.45(1H,m), 1.5–1.65(2H,m), 2.05–2.2(2H,m), 2.3–2.65(1H,br), 2.5–3.1(10H,m), 3.8–4.05(2H,q), 4.05–4.2 (2H,q), 6.8–6.9(2H,d), 7.1–7.2(2H,d).

The 3-(4-[2-ethoxycarboxyethyl]phenoxymethyl)-3-hydroxyquinuclidine borane used as starting material was prepared from 4-ethoxycarbonyl ethyl phenol using an analogous procedure to that described in Example 71 for the preparation of the borane starting material.

The procedure described in Example 71 was repeated using 4-ethoxycarbonylethylphenol (0.47 g) instead of 4-methoxyethoxyphenol. There was thus obtained 3-(4-[2-ethoxycarbonylethyl]phenoxymethyl-3-hydroxyquinuclidine borane complex as a yellow oil (0.74 g).

EXAMPLE 73

Using a similar procedure to that described in Example 21, but using 3-(2-allyl-4-[2-ethoxycarbonylethyl] phenoxymethyl)-3-hydroxy quinuclidine borane complex as starting material there was obtained 3-(2-allyl-4-[2-ethoxycarbonylethyl]phenoxymethyl)quinclidine-3-ol as a solid, m.p. 160–162° C., NMR(DMSOd$_6$/$CD_3COOD$): 1.0–1.15(3H,t), 1.55–1.75(1H,m), 2.1–2.35(2H,m), 2.6–2.8 (2H,t), 3.0–3.4(8H,m), 3.85–4.1(4H,m), 4.9–5.05(2H,m), 5.8–6.0(1H,m), 6.6(1H,s), 6.75–6.85(1H,d), 6.9–7.0(2H,m).

The 3-(2-allyl-4-[2-ethoxycarbonylethyl] phenoxymethyl)-3-hydroxyquinuclidine borane complex used as starting material was prepared from 2-allyl-4-ethoxycarbonylethylphenol (0.5 g) using a procedure analogous to that described in Example 74 for the preparation of the borane starting material. There was thus obtained 3-(2-allyl-4-[2-ethoxycarbonylethyl]phenoxymethyl)-3-hydoxyquinuclidin e borane complex as an oil (0.87 g); NMR(CDCl$_3$): 0.5–2.5(3H,br), 1.15–1.3(3H,t), 1.5–1.7(1H, m), 1.7–1.9(2H,m), 2.2–2.4(2H,m), 2.5–2.65(2H,t), 2.7–2.8 (1H,s), 2.8–3.3(8H,m), 3.3–3.4(2H,d), 3.8–4.05(2H,q), 4.05–4.2(2H,q), 4.9–5.1(2H,m), 5.85–6.1(1H,m), 6.7–6.8 (1H,d) and 6.9–7.1(2H,m).

EXAMPLE 74

Using a similar procedure to that described in Example 21 but using 3-(2-allyl-4-[2-methoxyethoxy]phenoxymethyl)-3-hydroxyquinuclidine borane complex as starting material, there was obtained 3-(2-allyl-4-[2-methoxyethoxy]

phenoxymethyl)quinuclidine-3-ol is a solid, m.p. 58–60° C., NMR: 1.3–1.45(1H,m), 1.55–1.7(2H,m), 2.05–2.2(2H,m), 2.45–2.65(1H,br), 2.6–3.1(6H,m), 3.3–3.4(2H,m), 3.45(3H, s), 3.7–3.75(2H,m), 3.75–4.05(2H,q), 4.05–4.1(2H,m), 4.95–5.1(2H,m), 5.85–6.05(1H,m), 6.7–6.8(3H,m).

The 3-(2-allyl-4-[2-methoxyethoxy]phenoxymethyl)-3-hydroxyquinuclidine borane used as starting material was prepared from 2-allyl-4-methoxyethoxyphenol (0.42 g) using a method analogous to that described for the preparation of the borane starting material in Example 71.

There was thus obtained 3-(2-allyl-4-[2-methoxyethoxy] phenoxymethyl)-3-hydroxyquinuclidine borane complex as an oil (0.48 g). NMR(CDCl$_3$): 0.7–2.4(3H,br), 1.6–1.7(1H, m), 1.7–1.85(2H,m), 2.2–2.4(2H,m), 2.75(1H,s), 2.8–3.25 (6H,m), 3.3–3.4(2H,d), 3.45(3H 3.7–3.75(2H,m), 3.8–4.0 (2H,q), 4.05–4.1(2H,m), 4.9–5.1(2H,m), 5.85–6.0(1H,m) and 6.7–6.8(3H,m).

EXAMPLE 75

The procedure described in Example 7 was repeated using 4-bromo-2-methoxyphenol in place of 4-iodophenol. There was thus obtained, after purification by flash chromatography on silica gel using a gradient of 0 to 20% methanol in dichloromethane containing 1% ammonia (density, 0.88 g/cm$^3$) followed by recrystallisation from acetonitrile, 3-[2-(3-methoxy-4-(2-methoxyethoxy)phenyl)ethynyl] quinuclidin-3-ol as a solid, m.p. 130–131° C., NMR: 1.21–1.40(1H,m), 1.47–1.65(1H,m), 1.77–2.00(3H,m), 2.66 (4H,t), 2.75–3.12(2H,q), 3.60–3.70(2H,m), 3.76(3H,s), 4.02–4.12(2H,m), 5.49(1H,s) and 6.87–6.98(3H,m).

EXAMPLE 76

The procedure described in Example 7 was repeated using 4-bromo-2-fluorophenol in place of 4-iodophenol. There was thus obtained 3-[2-(3-fluoro-4-(2-methoxyethoxy) phenyl)ethynyl]quinuclidin-3-ol as a solid, m.p. 136–139° C., NMR: 1.21–1.43(1H,m), 1.49–1.70(1H,m), 1.75–2.00 (3H,m), 2.70(4H,t), 2.75–3.15(2H,q), 3.30(3H,s), 3.60–3.75 (2H,m), 4.14–4.26(2H,m), 5.62(1H,s) and 7.10–7.32(3H, m).

EXAMPLE 77

The procedure described in Example 1 was repeated using methyl-3-[3,5-diallyl-4-trifluoromethylsulphonyloxy) phenyl)propionate as starting material in place of ethyl 3-(3-allyl-4-trifluoromethylsulphonyloxy)phenyl) propionate. There was thus obtained, after purification by flash chromatography on silica gel using 10% methanol in dichloromethane containing 1% ammonia (density, 0.88 g/cm$^3$) as eluent, 3-[2-(2,6-diallyl-4-(2-methoxycarbonylethyl)phenyl)ethynyl]quinuclidin-3-ol. Treatment with fumaric acid gave, a solid which was recrystallised from a mixture of acetone and diethyl ether to give the hemi-fumarate salt as a solid, 140–143° C., NMR: 1.35–1.52(1H,m), 1.6–1.78(1H,m), 1.85–2.1(3H,m), 2.6 (2H,m), 2.6(6H,t), 3.0(1H,br), 3.2(1H,br), 3.5(4H,d), 3.6 (3H,s), 4.25(2H,br+H$_2$O), 5.08(4H,m), 5.85–6.05(2H,m), 6.52(1H,s) and 6.97(2H,s).

The methyl-3-[3,5-diallyl-4-(trifluoromethylsulphonyloxy)phenyl]propionate used as starting material was prepared as follows.

A mixture of methyl-3(3-allyl-4-hydroxyphenyl) propionate (12.3 g), anhydrous potassium carbonate (13.8 g), and allylbromide (8.64 mls) in acetone (300 ml) was stirred at ambient temperature for two days. The reaction mixture was filtered and the residue washed with acetone. The filtrate and washings were combined and evaporated to give methyl-3-(3-allyl-4-allyloxyphenyl)proprionate as a pale yellow oil (14.0 g); NMR: 2.58(2H,t), 2.75(2H,t), 3.31(2H,d), 3.55(3H,s), 4.52(2H,d), 4.95–5.45(4H,m), 5.85–6.11(2H,m), 6.85(1H,d) and 7.0(2H,m).

Methyl-3-(3-allyl-4-allyloxyphenyl)propionate (4 g) was heated at 250° C. for 10 minutes and then cooled. The residue was purified by flash column chromatography on silica gel using 50% ethyl acetate in n-pentane as eluent to give methyl-3-(3, 5-diallyl-4-hydroxyphenyl)propionate (2.5 g); NMR:

2.5(2H,t), 2.7(2H,t), 3.32(4H,d), 3.57(3H,s), 4.96–5.1 (4H,m), 5.82–6.05(2H,m), 6.75(2H,s) and 8.07(1H,s).

Trifluoromethane sulphonic anhydride (1.68 g) was added dropwise at 0–5° C. to a stirred solution of methyl-3(3,5-diallyl-4-hydroxyphenyl)propionate (2.5 g) in dry pyridine (20 ml). The mixture was then stirred at ambient temperature for a further 16 hours. The pyridine was removed by evaporation. The residue was treated with water (30 ml) and the mixture was extracted with ether (3×30 ml). The ethereal extracts were combined, washed with water (30 ml), dried (MgSO$_4$) and evaporated. The residue was purified by filtration through a short pad of silica gel (Merck Art 7736) using a mixture of 50% ether in n-pentane as eluent to give methyl-3-[3,5-diallyl-4-(trifluoromethylsulphonyloxy) phenyl]propionate (3.5 g) as a pale yellow oil; NMR: 2.52(2H,t), 2.75(2H,t), 3.34(4H,d), 3.48(3H,s), 4.87–5.03 (4H,m), 5.68–5.9(2H,m) and 7.03(2H,s).

EXAMPLE 78

Using the method described in Example 21, but using 2-hydroxymethyl-4-(2-methoxyethoxy)phenol as starting material and omitting the step of treating with fumaric acid, there was obtained 3-[2-hydroxymethyl-4-(2-methoxyethoxy)phenyloxymethyl]quinuclidin-3-ol as an oil (313 mg) NMR(CDCl$_3$): 1.32–1.42(1H,br), 1.61(2H,br), 2.1 (2H,br), 2.80(6 h,v.br), 3.4(3H,s), 3.72(2H,m), 3.83(1H,d), 4.08(3H,m), 4.62(2H,q), 6.80(2H,d) and 6.90(1H,m); m/z 338(M+H).

The 2-hydroxymethyl-4-(2-methoxyethoxy)phenol used in above procedure was prepared in the following manner.

Sodium borohydride (519 mg) was added to a solution of 2-hydroxy-5-(2-methoxyethoxy)benzaldehyde (5.55 g) in ethanol (25 ml) whilst maintaining the temperature at 5° C. The resulting mixture was stirred at 25° C. for 30 minutes. The mixture was poured into water (100 ml) and acidified to pH 4 using glacial acetic acid. The mixture was extracted with ethyl acetate (3×10 ml). The ethyl acetate extracts were combined, washed with brine (15 ml), dried (MgSO$_4$) and evaporated to give an oil (4.1 g). This oil was purified by flash chromatography on silica gel (Merck Art No 3985) using a gradient of 30 to 55% ethyl acetate/hexane as eluent to give 2-hydroxymethyl-4-(2-methoxyethoxy)phenol as an oil (2.67 g); NMR: 3.0(3H,s), 3.6(2H,m), 3.96(2H,m), 4.45 (2H,d), 4.96(1H,t), 6.64(2H,m), 6.87(1H,d) and 8.84(1H,s); m/z 198(M).

The 2-hydroxy-5-(2-methoxyethoxy)benzaldehyde used as starting material was prepared as in example 41.

EXAMPLE 79

3-[2-(2-formyl-4-(2-methoxycarbonylethyl)phenyl] ethynyl]quinuclidin-3-ol (575 mg) was stirred with methanol (25 ml) at ambient temperature under an atmosphere of argon. Sodium borohydride (329 mg) was added portionwise over 5 minutes to the reaction mixture and stirring continued at ambient temperature overnight. Water (25 ml) was added and the mixture was extracted with ethyl acetate (25 ml). The organic phase was separated, washed with saturated aqueous sodium carbonate (3×25 ml), water (3×25 ml), dried (MgSO$_4$) and evaporated. The residue was purified by elution through silica gel (10 g Bond elut column) with a gradient of 0–30% methanol in dichloromethane to give 3-[2-(2-hydroxymethyl-4-(2-methoxycarbonylethyl) phenyl)ethynyl]quinuclidin-3-ol (160 mg) as a solid, m.p. 35.8° C.; microanalysis, found: C, 69.2; H, 7.5; N, 3.9% C$_{20}$H$_{25}$NO$_4$ 0.2 H$_2$O requires: C, 69.2; H, 7.38; N, 4.04%; NMR(CDCl$_3$): 1.4(1H,m), 1.66(1H,m), 2.02(3H,m), 2.62 (2H,t), 2.8(3H,m), 2.95(2H,t), 3.03(1H,d), 3.27(1H,d), 3.66 (3H,s), 4.75(2H,s), 7.07(1H,m) and 7.3(2H,m); m/z 344 (M+H).

EXAMPLE 80

Using the method described in Example 1, but carrying out the reaction at ambient temperature overnight and with 2-iodophenylacetonitrile (667 mg) in place of ethyl 3-(3-allyl-4-trifluoromethylsulphonyloxyphenyl)propionate there was thus obtained 2-[2-(2-cyanomethyl phenyl)ethynyl] quinuclidin-3-ol as a solid (292 mg), m.p. 147.1° C., microanalysis found: C, 75.6; H, 7.1; N, 10.4% C$_{17}$H$_{18}$N$_2$O 0.25 H$_2$O requires: C, 75.4; H, 6.88; N, 10.3%; NMR: 1.3(1H,m), 1.59(1H,m), 1.94(3H,m), 2.69(4H,m), 2.84(1H, d), 3.17(1H,d), 4.05(2H,s), 5.63(1H,s) and 7.41(4H,m); m/z 267(M+H).

EXAMPLE 81

Using the method described in Example 1 but carrying out the reaction at ambient temperature overnight and with methyl 3-(3-formyl-4-trifluoromethanesulphonyloxyphenyl)propionate (884 mg) in place of ethyl 3-(3-allyl-4-trifluoromethylsulphonyloxyphenyl)propionate, there was thus obtained 3-[2-[2-formyl-4-(2-methoxycarbonylethyl) phenyl)ethynyl]quinuclidin-3-ol as a solid (437 mg), m.p. 182.3° C.; microanalysis, found: C, 69.4; H, 6.8; N 4.0% C$_{20}$H$_{23}$NO$_4$ 0.25 H$_2$O requires: C, 69.4; H, 6.85; N, 4.05%; NMR: 1.32(1H,m), 1.62(1H,m), 1.9(2H,m), 2.68(6H,m), 2.85(1H,d), 2.93(2H,t 3.14(1H,d), 3.57(3H,s), 5.68(1H,s), 7.54(2H,m), 7.68(1H,m) and 10.39(1H,s); m/z 342(M+H).

The methyl-3-(3-formyl-4-trifluoromethylsulphonyloxyphenyl)propionate used as starting material was prepared in an analogous manner to the preparation of the starting material for Example 41.

EXAMPLE 82

Sodium borohydride (28.4 mg) was added to a solution of 3-[2-(3-formyl-4-(2-methoxyethoxy)phenyl)ethynyl] quinuclidin-3-ol in methanol at 0° C. The mixture was allowed to warm to ambient temperature and stirred for 1.5 hours. The reaction mixture was poured onto water (15 ml) and the mixture extracted with ethyl acetate (3×20 ml). The ethyl acetate extracts were combined, washed with brine solution (20 ml), dried (MgSO$_4$) and evaporated. The residue was dissolved in acetonitrile (5 ml) and diethylether was added to give, on cooling, a solid (262 mg). This solid was further purified by crystallisation from acetonitrile to give 3-[2-(2-hydroxymethyl-4-(2-methoxyethoxy)phenyl) ethynyl]quinuclidin-3-ol (217 mg) as a solid, m.p. 98.5–100.0° C.; microanalysis, found C, 67.5%; H, 7.7%, N, 6.9%, C$_{19}$H$_{25}$NO$_4$ 0.8CH$_3$CN requires: C, 67.9%; H, 7.6%; N, 6.9%; NMR(CDCl$_3$): 1.40(1H,m), 1.65(1H,m), 2.0(3H, s), 2.05(3H,m), 2.8(4H,t), 3.03(1H,d), 3.28(1H,d), 3.45(3H, s), 3.75(2H,t), 4.13(2H,t), 4.72(2H,s), 6.78(1H,m), 7.05(1H, d) and 7.3(1H,t); m/z 332(M+H).

EXAMPLE 83

Using a similar procedure to that described in Example 1 but using (+)-3-ethynyl-3-hydroxyquinuclidine in place of 3-ethynyl-3-hydroxyquinuclidine and methyl 4-[3-allyl-4-trifluoromethylsulphonyloxyphenyl)butanoate in place of ethyl 3-(3-allyl-4-trifluoromethylsulphonyloxyphenyl) propionate, there was thus obtained (+)-3-[2-(2-allyl-4-(3-methoxycarbonylpropyl)phenyl)ethynyl]quinuclidin-3-ol as a gum, NMR(CDCl$_3$): 1.3–1.5(1H,m), 1.55–1.75(1H,m), 1.9–2.15(2H,m), 2.3–2.4(2H,t), 2.6–2.7(2H,t), 2.8–3.0(4H, m), 3.0–3.15(1H,d), 3.25–3.4(1H,d), 3.5–3.55(2H,m), 3.65 (3H,s), 5.0–5.1(2H,d), 5.9–6.05(1H,m), 6.95–7.05(2H,d) and 7.3–7.4(1H,d); $\alpha^{25}_D$=+24.1°.

The methyl 4-(3-allyl-4-trifluoromethylsulphonyloxyphenyl)butanoate used as starting material was prepared in a similar manner to ethyl 3-(3-allyl-4-trifluoromethylsulphonyloxyphenyl)propionate (described in Example 1).

EXAMPLE 84

Using the method described in Example 83 but using (−)-3-ethynyl-3-hydroxyquinuclidine in place of (+)-3-ethynyl-3-hydroxyquinuclidine there was thus obtained (−)-3-[2-(2-allyl-4-(3-methoxycarbonylpropyl)phenyl)ethynyl] quinuclidine-3-ol; NMR(CDCl$_3$): 1.4–1.5(1H,m), 1.55–1.8 (1H,m), 1.8–2.2(5H,m), 2.1–2.4(2H,t), 2.6–2.7(2H,t), 2.8–3.0(2H,m), 3.0–3.15(1H,d), 3.3–3.4(1H,d), 3.4–3.6(2H, m), 3.66(3H,s), 5.0–5.1(2H,m), 5.9–6.1(1H,m), 6.95–7.05 (2H,m), 7.3–7.4(1H,d), $\alpha^{25}_D$=−20.3°.

EXAMPLE 85

Sodium hydroxide (44 mg) was added to a mixture of (+)-3-[2-(2-allyl-4-(3-methoxycarbonylpropyl)phenyl) ethynyl]quinuclidin-3-ol, water (1 ml) and methanol (0.5 ml). The reaction mixture was stirred at ambient temperature overnight. The reaction mixture was evaporated to dryness. Water was added to the residue, and the mixture acidified using dilute aqueous hydrochloric acid. The mixture was evaporated and acetone was added to the residue. The mixture was filtered and the filtrate evaporated to give (+)-3-[2-(2-allyl-4-(3-carboxypropyl)phenyl)ethynyl] quinuclidin-3-ol hydrochloride as a gum (62 mg), NMR: 1.7–1.9(3H,m), 1.9–2.1(1H,m), 2.1–2.3(4H,m), 2.5–2.65 (2H,m), 3.1–3.6(4H,m), 5.0–5.15(2H,d), 5.46(1H,m), 6.45 (1H,t), 7.05–7.1(2H,m) and 7.3–7.4(1H,d); $\alpha^{25}_D$=−3.0

EXAMPLE 86

Using a similar method to that described in Example 1 but using (+)-3-ethynyl-3-hydroxyquinuclidine and methyl 5-(3-allyl-4-trifluoromethylsulphonyloxyphenyl)pentanoate as starting materials there was thus obtained (+)-3-[2-(2-allyl-5-(4-methoxycarbonylbutyl)phenyl)ethynyl] quinuclidine-3-ol, NMR: 1.3–1.5(1H,m), 1.55–1.7(5H,m), 1.7–2.2(4H,m), 2.25–2.40(2H,m), 2.55–2.7(2H,m), 2.7–3.0 (4H,m), 3.0–3.1(1H,d), 3.25–3.4(1H,d), 3.4–3.5(2H,m), 3.65(3H,s), 5.0–5.1(2H,m), 5.85–6.1(1H,m), 6.9–7.0(2H,m) and 7.3–7.4(1H,d); $\alpha^{25}_D$=+19.2°

EXAMPLE 87

A mixture of 3-[2-(2-allyl-4-methoxycarbonylphenyl) ethynyl]quinuclidin-3-ol (0.64 g), sodium cyanide (50 mg)

and N,N-dimethylethanolamine (10 ml) was heated at 90° C. for 24 hours. The mixture was evaporated to give an oil which was partitioned between ethyl acetate and water. The organic phase was separated, washed with brine, dried (MgSO$_4$) and evaporated. The residue was purified by flash column chromatography on silica gel using 10% methanol in dichloromethane containing 1% ammonia (density 0.88 g/cm$^3$) as eluent to give 3-[2-(2-allyl-4-(2-(N,N-dimethylamino)ethoxycarbonyl)phenyl)ethynyl] quinuclidin-3-ol as a gum (0.559 g); microanalysis found: C, 66.7; H, 7.6; N, 6.7%, C$_{23}$H$_{30}$N$_2$O$_3$.0.4CH$_2$Cl$_2$.0.1 H$_2$O requires 7.47; N, 6.7%; NMR (CDCl$_3$): 1.32–1.55(1H, m), 1.55–1.88(1H, m), 1.88–2.20(3H, m), 2.33(6H, s), 2.70(2H, t), 2.65–3.15(4H, m), 3.07(1H, d), 3.33(1H, dd), 3.56(2H, d), 4.41(2H, t), 4.98–5.15(2H, m), 5.29(CH$_2$Cl$_2$), 5.85–6.10 (1H, m), 7.43(1H, d) and 7.71–7.90(2H, m); m/Z 383 (M+H).

EXAMPLE 88

A methanolic solution of potassium hydroxide was added to a solution of 3-[2-(2-allyl-4-methoxycarbonylphenyl) ethynyl]quinuclidin-3-ol (0.975 g) in methanol (10 ml) until hydrolysis was complete as judged thin layer chromatography. The precipitate formed was collected by filtration, washed with pentane and dried over phosphorus pentoxide. A mixture of the dried solid (0.45 g) and 2-chloro-N,N'-dimethylacetamide (0.144 ml) in 5 ml of 1,3-dimethyl-3,4, 6-tetrahydro 2-pyrimidinone (DHPU) was heated at 70° C. for 3 hours. The mixture was cooled to ambient temperature and partitioned between water and ethyl acetate. The organic phase was washed with brine and dried (MgSO$_4$). Evaporation gave an oil which was purified by chromatography on silica gel using a gradient of 0% to 10% methanol in dichloromethane containing 1% ammonia (density 0.88 g/cm$^3$) as eluent to give 3-[2-(2-allyl-4-(2—N,N'-dimethylacetamidoxy)carbonyl phenyl)ethynyl]quinuclidin-3-ol as a gum (56 mg); microanalysis found: C, 67.4; H, 7.5; N, 7.1%; C$_{23}$H$_{28}$N$_2$O$_4$ 0.75H$_2$O requires: C, 67.4; H, 7.25; N, 6.83%; NMR (CDCl$_3$): 1.35–1.55(1H, m), 1.55–1.80(1H, m), 1.87–2.20(3H, m), 2.75–3.15(11H, m), 3.33(1H, dd), 3.56(2H, d), 4.94(2H, s), 4.98–5.15(2H m), 5.85–6.07(1H, m), 7.45(1H, d) and 7.80–8.00(2H, m); m/Z 397 (M+H).

EXAMPLE 89

A mixture of 3-[2-(2-ethoxy-4-formylphenyl)ethynyl] quinuclidin-3-ol (598 mg), carbethoxymethylenetriphenylphosphorane (1.04 g) in toluene (10 ml) was heated at 100° C. for 5 hours. The reaction mixture was cooled to ambient temperature and the toluene evaporated to give a solid which was crystallised from acetonitrile to give 3-[2-(2-ethoxy-4-(2-ethoxycarbonylethenyl)phenyl)ethynyl] quinuclidin-3-ol (328 mg) as a solid, m.p. 152–153° C.; microanalysis found: C, 71.5; H, 7.3; N, 3.7%; C$_{22}$H$_{27}$NO$_4$ requires: C, 71.5: H, 7.37; N, 3.79%; NMR (CDCl$_3$): 1.33(3H, t), 1.36–1.52(4H, m), 1.55–1.70(1H, m), 1.90–2.30 (4H, m), 2.73–3.00(4H, m), 3.04(1H, d), 3.34(1H, dd), 4.09(2H, q), 4.26(2H, q), 6.33–6.45(1H, d), 6.93–7.03(1H, d,), 7.03(1H, dd), 7.35(1H, d), 7.60(1H, d); m/Z 370 (M+H).

The 3-[2-(2-ethoxy-4-formylphenyl)ethynyl] quinuclidine-3-ol used as starting material was prepared as follows.

Ethyl-3-(3-allyl-4-trifluoromethylsulphonyloxyphenyl) propionate was prepared from ethyl vanillin using the procedure described in Example 1 for the preparation of ethyl 3-(3-allyl-4-trifluoromethylsulphonyloxyphenyl) propionate. Thus there was obtained 3-ethoxy-4-trifluoromethylsulphonyloxybenzaldehyde as an oil; NMR (CDCl$_3$): 1.50(3H, t), 4.22(2H, q), 7.36–7.58(3H, m), 9.97 (1H, s); m/Z 299 (M+H).

Using the method described in Example 1 but with 3-ethoxy-4-trifluoromethylsulphonyloxybenzaldehyde in place of ethyl 3-(3-allyl-4-trifluoromethylsulphonyloxyphenyl)propionate there was thus obtained 3-[2-(2-ethoxy-4-formylphenyl)ethynyl] quinuclidin-3-ol as a solid, m.p. 148–153° C.; microanalysis, found: C, 71.8; H, 7.3; N, 4.5%; C$_{18}$H$_{21}$NO$_3$ requires: C, 72.2; H, 7.07; N, 4.68%; NMR (CDCl$_3$): 1.35–1.54(1H, m), 1.45(3H, t), 1.56–1.73(1H, m), 1.98–2.20 (3H, m), 2.85(4H, br t), 3.05(1H, d), 3.37(1H, dd), 4.13(2H, q), 7.30–7.40(2H, m), 7.50(1H, d), 9.93(1H, s); m/Z 300 (M+H).

EXAMPLE 90

The procedure described in Example 35 was repeated using (+)-3-ethynyl-3-hydroxyquinuclidine in place of (±)-3-ethynyl-3-hydroxy quinuclidine to give (+)-3-[2-(2-allyl-4-(3-methoxypropyl)phenyl)ethynyl]quinuclidin-3-ol as an oil, NMR: 1.3–1.5 (1H, m), 1.6–1.8 (3H, m), 1.8–2.2 (3H, m), 2.53–2.65 (2H, t), 2.65–3.15 (6H, m), 3.2 (3H s), 3.25–3.35 (2H, t), 3.5–3.6 (2H, d), 5.0–5.1 (2H, m), 5.6 (1H, s), 5.8–6.6 (1H, m), 7.0–7.1 (2H, d) and 7.2–7.3 (2H, d). [α]$^{20}_D$+15.4°.

EXAMPLE 91

The procedure described in Example 35 was repeated using (−) 3-ethynyl-3-hydroxyquinuclidine in place of (±) 3-ethynyl-3-hydroxyquinuclindine to give (−)-3-[2-(2-allyl-4-(3-methoxypropyl)phenyl)ethynyl]quinuclindin-3-ol as an oil, NMR: 1.3–1.5 (1H, m), 1.5–1.7 (1H, m), 1.7–1.85 (2H, m), 1.85–2.05 (3H, m), 2.55–2.65 (2H, t), 2.65–2.8 (4H, m), 2.8–3.0 (1H, d) 3.05–3.15 (1H, d), 3.2 (3H, s), 3.25–3.35 (2H, t), 3.4–3.5 (2H, d), 5.0–5.1 (2H, m), 5.6 (1H, s), 5.9–6.0 (1H, m), 7.0–7.1 (2H, d) and 7.2–7.3 (2H, d); [α]$^{20}_D$−19.4°.

EXAMPLE 92

Using the procedure described in Example 11, but with 1-allyl-2-trifluoromethylsulphonyloxy-5-(2-methoxyethoxymethyl)benzene in place of 1-(4-bromo-2,6-dimethylphenoxy)-2-methoxyethane, there was thus obtained 3-[2-(2-allyl-4-(2-methoxyethoxymethyl)phenyl) ethynyl]quinuclidin-3-ol as an oil, NMR: 1.25–1.45 (1H, m), 1.5–1.7 (1H, m), 1.8–2.1 (3H, m), 2.6–3.2 (6H, m), 3.3 (3H, s), 3.45–3.6 (6H, m), 4.5 (2H, s), 5.0–5.2 (2H, m), 5.6 (1H, s), 5.9–6.1 (1H, m) and 7.1–7.4 (3H, m).

The compound of formula 2(2=trifluoromethysulphonyloxy) used as starting material was prepared as follows.

2-(4-bromobenzyloxy) 1-methoxyethane (preparation described in Example 11) (10 g) was added to a stirred mixture of oven dried magnesium (2.74 g) in tetrahydrofuran (20 ml) under an atmosphere of argon. A crystal of iodine was added and the mixture heated until an exothermic reaction commenced. A solution of the remaining 2-(4-bromobenzyloxy)-1-methoxyethane (13.4 g) in tetrahydrofuran (60 ml) was added dropwise to maintain the temperature of the reaction mixture at reflux. When the addition was complete the mixture was heated at reflux for a further 20 minutes, allowed to cool and added to trimethylborate (11.74 g) in tetrahydrofuran (60 ml) under argon at −10° C., dropwise over 45 minutes whilst maintaining the temperature below −5° C. After stirring for 15 minutes, chilled acetic acid (9.36 g) was added, followed by the dropwise addition of 30% hydrogen peroxide (11.77 ml) in water (11 ml) whilst maintaining the temperature below 0° C. The mixture was allowed to warm to ambient temperature over a period of 20 minutes and then washed successively with saturated ammonium sulphate containing ferrous ammonium sulphate until the aqueous layer no longer turned brown. The organic layer was dried ($MgSO_4$) and evaporated. The residue was dissolved in ether (100 ml) and extracted into IM aqueous sodium hydroxide (50 ml×3). The aqueous extract was acidified with 2M aqueous hydrochloric acid and the mixture was extracted with ethyl acetate (3×50 ml). The ethyl acetate extracts were combined, dried ($MgSO_4$) and evaporated. The residue was further purified by flash chromatography on silica gel using 10% ethyl acetate in toluene as eluent to give 2-(4-hydroxybenzyloxy)-1-methoxyethane (10.4 g) as a colourless oil; NMR ($CDCl_3$): 3.4 (3H, s), 3.5–3.7 (4H, m), 4.5 (2H, s), 6.7–6.8 (2H, d), 7.1–7.3 (2H, d).

This material was used to prepare using an analogous procedure to that described in example 35 for the preparation of 3-(-4-allyloxyphenyl)propanol. There was thus obtained 2-(4-allyloxybenzyloxy)-1-methoxyethane as an oil. NMR ($CDCl_3$): 3.4 (3H, s), 3.5–3.7 (4H, m), 4.5–4.6 (4H, m), 5.2–5.5 (2H, m), 6.0–6.2 (1H, m), 6.8–6.9 (2H, d), 7.2–7.3 (2H, d).

This material was used to prepare 2-(2-allyl-4-hydroxybenzyloxy)-1-methoxyethane using an analogous procedure to that described in example 35 for the preparation of 3-(2-allyl-4-hydroxyphenyl)-1-methoxypropane. There was thus obtained 2-(2-allyl-4-hydroxybenzyloxy)-1-methoxy ethane as a colourless oil, NMR ($CDCl_3$): 3.4 (5H, m), 3.5–3.7 (4H, m), 4.5(2H,s), 5.05–5.2 (3H, m) 5.9–6.1 (1H, m), 6.7–6.8 (1H, d), 7.05–7.15 (2H, m).

This material was used to prepare 2-(3-allyl-4-trifluoromethylsulphonyloxybenzyloxy)-1-methoxyethane using an analogous procedure to that described in example 1 for the preparation of ethyl 3-(3-allyl-4-trifluoromethylsulphonyloxyphenyl)propionate. There was thus obtained 2-(2-allyl-4-hydroxybenzyloxy)-1-methoxyethane as a colourless oil, NMR ($CDCl_3$) 3.4 (3H, s), 3.45–3.55 (2H, d), 3.55–3.7 (4H, m), 4.6 (2H, s), 5.0–5.2 (2H, m), 5.8–6.0 (1H, m), 7.2–7.4 (3H, m).

EXAMPLE 93

A solution of hydrogen chloride in ethanol was added dropwise to a stirred solution of 3-(4-cyanomethylphenoxymethyl)quinuclidin-3-ol borane complex (0.3 g) in acetone (3 ml, analar) until the solution was pH1. A solid separated and the mixture was stirred for 2 hours at ambient temperature under an atmosphere of argon. The solid was collected by filtration and washed with acetone (3 ml) to give 3-(4-cyanomethylphenoxymethyl) quinuclidin-3-ol hydrochloride (0.27 g) as a yellow solid, m.p. 185–188° C.; microanalysis, found: C, 61.7; H, 7.1; N, 8.7%; $C_{16}H_{20}N_2O_2$ HCl 0.15 $H_2O$ requires: C, 61.7; H, 6.9; N, 9.0%; NMR: 1.55–2.05 (3H, m), 2.1–2.35 (2H, m), 2.95–3.5 (6H, m), 3.9–3.95 (2H, s) 4.0–4.15 (2H, q), 5.45–5.7 (1H, s), 6.95–7.05 (2H, d), 7.25–7.35 (2H, d) and 10.5–10.8 (1H, br), m/z 273 (M+H).

The 3-(4-cyanomethylphenoxymethyl)quinuclidin-3-ol borane complex used as starting material was prepared as follows.

A mixture of 4-hydroxybenzyl cyanide (0.27 g), 3-methylenequinuclidine oxide borane complex (0.31 g), and anhydrous potassium carbonate (0.42 g) in dry dimethylformamide (1 ml) was heated at 75° C. for 7 hours under an atmosphere of argon. There was thus obtained 3-(4-cyanomethylphenyloxymethyl)quinuclidin-3-ol borane complex as an orange solid.

EXAMPLE 94

The procedure described in Example 93 was repeated using 3-(4-styrylphenoxymethyl)quinuclidin-3-ol borane complex (0.25 g), instead of 3-(4-cyanomethylphenoxymethyl)quinuclidin-3-ol borane complex, in acetone (5 ml, analar). There was thus obtained 3-(4-styrylphenoxymethyl)quinuclidin-3-ol hydrochloride (0.23 g) as a colourless solid, m.p. 235–238° C.; microanalysis, found: C, 70.2; H, 7.1; N, 3.6%; $C_{22}H_{25}NO_2$ HCl 0.25 $H_2O$ requires: C, 70.2; H, 7.1; N, 3.7%; NMR: 1.55–2.05 (3H, m), 2.1–2.35 (2H, m), 2.95–3.5 (6H, m), 4.0–4.2 (2H, q), 5.3–5.85 (1H, br), 6.9–7.1 (2H, d), 7.1–7.2 (2H, d), 7.2–7.3 (1H, m), 7.3–7.45 (2H, t) and 7.45–7.7 (4H, m), m/z 336 (M+H).

The 3-(4-styrylphenoxymethyl)quinuclidin-3-ol borane complex used as starting material was prepared from 4-hydroxystilbene using an analagous procedure to that described in Example 93 for the preparation of the borane starting material. The procedure described in Example 93 was repeated using 4-hydroxystilbene (0.39 g) instead of 4-hydroxybenzyl cyanide, except that the reaction mixture was extracted with ethyl acetate (50 ml). The ethyl acetate extract was washed with water (3×20 ml), dried ($Na_2SO_4$) and evaporated. There was thus obtained 3-(4-styrylphenoxymethyl)quinuclidin-3-ol borane complex (0.28 g), as an off-white solid.

EXAMPLE 95

The procedure described in Example 93 was repeated using 3-[4-(2-cyanoethyl)phenoxymethyl]quinuclidin-3-ol borane complex (0.3 g), instead of 3-(4-cyanomethylphenoxymethyl)quinuclidin-3-ol borane complex, except that the reaction mixture was evaporated. The residual gum was dissolved in aqueous 1M aqueous hydrochloric acid (3 ml) and the solution was washed with ethyl acetate (4×3 ml). The aqueous layer was basified with solid sodium carbonate and the mixture was extracted with ethyl acetate (3×4 ml). The ethyl acetate extracts were combined, dried ($Na_2SO_4$) and evaporated. The solid residue was triturated with diethyl ether to give 3-[4-(2-cyanoethyl) phenoxymethyl]quinuclidin-3-ol (0.15 g) as a colourless solid, m.p. 92–94° C.; microanalysis, found: C, 70.0; H, 7.8; N, 9.5%; $C_{17}H_{22}N_2O_2$ 0.3$H_2O$ requires: C, 70.0; H, 7.8; N, 9.6%; NMR ($CDCl_3$): 1.3–1.5 (1H, m), 1.5–1.7 (2H, m), 2.0–2.2 (2H, m), 2.3–2.6 (1H, br), 2.55–2.65 (2H, t), 2.6–3.1 (8H, m), 3.8–4.1 (2H, q), 6.85–6.95 (2H, d) and 7.1–7.2 (2H, d), m/z 287 (M+H).

The 3-[4-(2-cyanoethyl)phenoxymethyl]quinuclidin-3-ol borane complex used as starting material was prepared from 3-(4-hydroxyphenyl)propionitrile using an analogous procedure to that described in Example 93 for the preparation of the borane starting material. The procedure described in Example 93 was repeated using 3-(4-hydroxyphenyl) propionitrile (0.29 g) instead of 4-hydroxybenzyl cyanide. There was thus obtained 3-[4-(2-cyanoethyl) phenoxymethyl]quinuclidin-3-ol borane complex (0.32 g) as an oil.

EXAMPLE 96

In a similar manner to that in Example 93, 3-(2-allyl-4-hydroxymethylphenyloxymethyl)quinuclidin-3-ol borane complex (157 mg) was deprotected to give 3-(2-allyl-4-hydroxymethylphenyloxymethyl)quinuclidin-3-ol hydrochloride (121 mg) which was obtained as a white crystalline solid hydrochloride directly from the reaction mixture on adding an equal volume of ether; microanalysis, found: C, 62.2; H, 7.7; N, 3.8%; $C_{18}H_{25}NO_3$ hydrochloride hemihydrate requires, C, 62.0; H, 7.8; N, 4.01%; NMR: 1.6–2.0 (3H, m), 2.3–2.4 (2H, bs), 2.9–3.7 (9H, m), 3.9–4.2 (2H, q), 4.4 (2H, s), 4.95–5.15 (2H, m), 5.15–5.65 (1H, bs), 5.85–6.1 (1H, m) and 6.85–7.2 (3H, m), m/z 304 (M+H).

The starting material was prepared as follows. In a manner similar to example 51 but using a 15 hour reaction time, 2-allyl-4-formylphenol (1.0 g) was reacted with 3-methylenequinuclidine oxide (0.944 g) in DMF (3.1 ml) to afford 3-(2-allyl-4-formylphenyloxymethyl)quinuclidin-3-ol borane complex (869 mg), obtained as a white crystalline solid after purification by chromatography on silica gel eluted with 15% acetone/pentane, NMR: 0.8–2.0 (6H, m), 2.0–2.3 (2H, bs), 2.65–3.1 (6H, m), 3.44–3.49 (2H, d), 4.14 (2H, s), 5.0–5.35 (3H, m), 5.87–6.11 (1H, m), 7.18–7.22 (1H, d), 7.68–7.69 (1H, d), 7.75–7.87 (1H, dd) and 9.86 (1H, s).

A solution of 3-(2-allyl-4-formylphenyloxymethyl-3-hydroxyquinuclidine borane complex (175 mg) in gently warmed ethanol (2.0 ml) was treated with sodium borohydride (24 mg). After 1 hour the ethanol was removed by evaporation and the residue partitioned between ether (3×5 ml) and water (2 ml). The ether layers were combined washed with water (3 ml), dried ($MgSO_4$) and evaporated to give a colourless gum (176 mg) which was purified by chromatography on silica gel eluted successively with 20% and then 30% acetone/pentane to afford 3-(2-allyl-4-hydroxymethylphenyloxymethyl)quinuclidin-3-ol borane complex (169 mg) as a colourless gum.

EXAMPLE 97

Sodium borohydride (380 mg) was added to a solution of 3-[2-(2-allyl-4-formylphenyl)ethynyl]quinuclidin-3-ol (2.95 g) in ethanol (50 ml) whilst maintaining the temperature at 5° C. The resulting mixture was stirred at 25° C. for 2 hours and the ethanol was then evaporated. The residue was stirred with acetone (25 ml) and 1M aqueous hydrochloric acid (50 ml) was then added. The resulting mixture was stirred at 25° C. for 1 hour and sodium hydrogen carbonate (4.5 g) was then added. The mixture was extracted with ethyl acetate (3×50 ml), the ethyl acetate extracts combined, washed with brine (50 ml), dried ($Na_2SO_4$) and evaporated. The residue was dissolved in dichloromethane (85 ml) and triethylamine (1.8 ml) was added. A solution of pivaloyl chloride (1.14 g) in dichloromethane (8 ml) was added to the mixture whilst maintaining the temperature at 5° C. The resulting mixture was stirred at 25° C. for 12 hours. The dichloromethane was removed by evaporation and the residue was dissolved in ethyl acetate (215 ml). The mixture was washed with brine (100 ml), saturated sodium hydrogen carbonate solution (100 ml), dried ($Na_2SO_4$) and evaporated to give a residue which was purified by medium pressure column chromatography on alumina (Alumina N32-63) using a 49:1 (v/v) mixture of ethyl acetate and methanol as eluent to give 3-[2-(4-trimethylacetyloxymethyl-2-allylphenyl)ethynyl]quinuclidin-3-ol as a solid, m.p. 73° C.; microanalysis, found: C, 74.9; H, 8.2; N, 3.8%; $C_{24}H_{31}NO_3$ 0.2$H_2O$ requires: C, 74.9; H, 8.2; N, 3.6%; NMR ($CDCl_3$): 1.2 (9H, s), 1.4 (1H, m), 1.65 (1H, m), 2.1 (3H, m), 2.3 (1H, m), 2.8 (4H, t), 3.1 (1H, d), 3.3 (1H, dd), 3.5 (2H, d), 5.1 (4H, m), 5.9 (1H, m), 7.1 (2H, m) and 7.4 (1H, d), m/z 382 (M+H).

EXAMPLE 98

Sodium borohydride (380 mg) was added to a solution of 3-[2-(4-formyl-2-allylphenyl)ethynyl]quinuclidin-3-ol (2.95 g) and methylamine hydrochloride (1.01 g) in ethanol (50 ml) whilst maintaining the temperature at 5° C. The resulting mixture was stirred at 25° C. for 12 hours, filtered and the filtrate evaporated to leave a residue which was suspended in 1M aqueous sodium hydroxide solution (30 ml) and extracted with ethyl acetate (3×50 ml). The ethyl acetate extracts were combined, washed with brine (50 ml), dried ($Na_2SO_4$) and evaporated. The residue was triturated with diethyl ether to give 3-[2-(4-methylaminomethyl-2-allylphenyl)ethynyl]quinuclidin-3-ol as a solid, m.p. 80° C.; microanalysis, found C, 75.1; H, 8.3; N, 8.6%; $C_{20}H_{26}N_2O.0.5H_2O$ requires: C, 75.2; H, 8.5; N, 8.8%; NMR ($CDCl_3$): 1.4 (–1H, m), 1.65 (1H, m), 2.1 (5H, m), 2.5 (3H, s), 2.8 (4H, t), 3.1 (1H, d), 3.3 (1H, dd), 3.5 (2H, d), 3.7 (2H, s), 5.1 (4H, m), 5.9 (1H, m), 7.1 (2H, m) and 7.4 (1H, d), m/z 311 (M+H).

The 3-[2-(4-formyl-2-allylphenyl)ethynyl]quinuclidine-3-ol used as starting material was prepared using the method described in Example 1, but with 3-allyl-4-trifluoromethylsulphonyloxybenzaldehyde in place of ethyl 3-(3-allyl-4-trifluoromethylsulphonyloxyphenyl)-propionate. There was thus obtained 3-[2-(4-formyl-2-allylphenyl)ethynyl]quinuclidine-3-ol as a solid, m.p. 132–133° C.; microanalysis, found: C, 76.5; H, 7.3; N, 4.5% $C_{19}H_{21}NO_2$ 0.2 $H_2O$ requires C, 76.4; H, 7.2; N, 4.7%; NMR ($CDCl_3$): 1.4 (1H, m), 1.65 (1H, m), 2.1 (3H, m), 2.8 (4H, t), 3.1 (1H, d), 3.3 (1H, dd), 3.6 (2H, d), 5.1 (2H, m), 5.9 (1H, m), 7.3 (1H, d), 7.5 (2H, m) and 10.0 (1H, s), m/z 296 (M+H).

The 3-allyl-4-trifluoromethylsulphonyloxybenzaldehyde was prepared using the method described in Example 1, but with 4-hydroxybenzaldehyde in place of ethyl 3-(4-hydroxyphenyl)-propionate. There was thus obtained 3-allyl-4-trifluoromethylsulphonyloxybenzaldehyde as an oil; NMR ($CDCl_3$): 3.6 (2H, d), 5.2 (2H, m), 6.0 (1H, m), 7.5 (1H, d), 7.9 (2H, m) and 10.0 (1H, s).

EXAMPLE 99

3-[2-(4-formyl-2-allylphenyl)ethynyl]quinuclidin-3-ol (1.0 g) and methoxylamine hydrochloride were dissolved in ethanol (35 ml) and the mixture stirred at 25° C. for 12 hours. The ethanol was evaporated and the residue crystallised from ethyl acetate to give 3-[2-(4-methoxyiminomethyl-2-allylphenyl)ethynyl]quinuclidin-3-ol hydrochloride as a solid, m.p. 143° C.; microanalysis, found: C, 64.7; H, 7.0; N, 8.0% $C_{20}H_{24}N_2O_2$ HCl. 0.5$H_2O$ requires C, 64.9; H, 7.0; N, 7.6% NMR ($[CD_3]_2SO/CD_3COOD$): 1.5–2.3 (5H, m), 3.2 (4H, t), 3.4 (1H, d), 3.6 (1H, dd), 3.9 (3H, s), 5.1 (2H, m), 6.0 (1H, m), 7.5 (3H, m) and 8.2 (1H, s), m/z 325 (M+H).

EXAMPLE 100

Bis (triphenylphosphine)-palladium (II) chloride (147 mg) and copper (I) iodide (74 mg) were added to a solution of diethyl (3 allyl 4 trifluoromethylsulphonyloxybenzylidine)malonate (3.3 g) and 3-ethynylquinuclidine-3-ol (1.37 g) in dimethylformamide (17 ml) and triethylamine (1.47 ml) at 5° C. under an atmosphere of argon. The mixture was stirred at 25° C. for 12 hours. Water (255 ml) was added and the mixture extracted with ethyl acetate (3×100 ml). The ethyl acetate extracts were combined, washed with brine (100 ml), dried ($Na_2SO_4$) and evaporated to give a residue which was purified by medium pressure column chromatography on alumina (Alumina N32-63) using a 99.1 (v/v) mixture of ethyl acetate and methanol as eluent to give 3-[2-(4-(2- dicarbethoxyethylenyl)-2-allylphenyl)ethynyl]quinuclidin-3-ol as a solid, m.p. 112° C., microanalysis, found: C, 71.1, H, 7.3; N, 3.1%; $C_{26}H_{31}NO_5$ requires C, 71.4; H, 7.1; N, 3.2%; NMR ($CDCl_3$): 1.3 (6H, t), 1.4 (1H, m), 1.65 (1H, m), 2.1 (3H, m), 2.8 (4H, t), 3.1 (1H, d), 3.3 (1H, dd), 3.5 (2H, d), 4.1 (4H, q), 5.1 (2H, m), 5.9 (1H, m), 7.1 (2H, m), 7.4 (1H, d) and 7.65 (1H, s), m/z 438 (M+H).

The diethyl (3-allyl-4-trifluoromethylsulphonyloxybenzylidine)malonate used as starting material was obtained as follows.

3-Allyl-4-hydroxybenzaldehyde (2.0 g) and diethylmalonate (2.37 g) were dissolved in toluene (50 ml) and piperidine (4 drops) and acetic acid (12 drops) were added. The mixture was heated at reflux using a Dean & Stark water separator until no more water was collected (2 hours). The toluene was evaporated to give a residue which was dissolved in diethyl ether (50 ml), washed with water (50 ml), saturated sodium hydrogen carbonate (25 ml), brine (25 ml), dried ($MgSO_4$) and evaporated to give a residue which was purified by medium pressure column chromatography on silica gel using a 4:1 (v/v) mixture of isohexane and ethyl acetate as eluent to give diethyl (3-allyl-4-hydroxybenzylidine)malonate as an oil, NMR ($CDCl_3$) 1.3 (6H, t), 3.4 (2H, d), 4.3 (4H, q), 5.2 (2H, m), 6.0 (1H, m), 6.6 (1H, d), 7.2 (2H, m) and 7.6 (1H, s).

Trifluoromethyl sulphonic anhydride (2.12 ml) was added dropwise over 20 minutes to a stirred solution of diethyl (3-allyl-4-hydroxybenzylidine)malonate (3.7 g) in pyridine (12 ml) at 0° C. under an atmosphere of argon. The mixture was stirred at 0° C. for 16 hours and was then added to cold water (180 ml). The aqueous mixture was extracted with diethyl ether (3×100 ml), the diethyl ether extracts combined, washed with 1M aqueous hydrochloric acid (3×50 ml), brine (100 ml), dried ($MgSO_4$) and evaporated to give a residue which was purified by medium pressure column chromatography on silica gel using a 19:1 (v/v) mixture of isohexane and ethyl acetate as eluent to give diethyl (3-allyl-4-trifluoromethylsulphonyloxybenzylidine) malonate as an oil NMR ($CDCl_3$): 1.3 (6H, t), 3.5 (2H, d), 4.3 (4H, q), 5.2 (2H, m), 6.0 (1H, m), 7.3 (2H, m), 7.4 (1H, s) and 7.7 (1H, s).

EXAMPLE 101

A mixture of 3-[2-(2-allyl-4-(butan-2-one)phenyl) ethynyl]quinuclidin-3-ol (0.3 g) in ethanol (10 ml), sodium acetate (0.085 g) and 0-ethylhydroxylamine hydrochloride (0.1 g) was heated at reflux for 16 hours.

The mixture mixture was cooled and the solvent removed by evaporation. The residue was triturated with a 80:20:3 (v/v/v) mixture of ethyl acetate/ethanol/triethylamine. The residue was purified by dry flash chromatography on 60H silica (Merck Art. No. 7736) using a 80:20:3 (v/v/v) mixture of ethyl acetate/ethanol/triethylamine as eluent to give 3-[2-(2-allyl-4-(3-ethoxyimino)butyl)ethynyl]quinuclidin-3-ol as an oil (0.22 g), microanalysis found; C, 73.5; H, 8.8; N, 7.2%; $C_{24}H_{32}N_2O_2.3/4H_2O$ requires C, 73.2; H, 8.6; N, 7.1%; m/z=381 (M+H).

EXAMPLE 102

Sodium borohydride (0.016 g) was added to a suspension of 3-[2-(2-allyl-4-(butan-2-one)-phenyl)ethynyl] quinuclidin-3-ol (0.2 g), in ethanol (5 ml) at 0° C. under an atmosphere of argon. The reaction mixture was allowed to warm to room temperature and stirred for 2 hours.

The reaction mixture was quenched by addition of saturated aqueous ammonium chloride solution (10 ml) and water (10 ml). The aqueous mixture was extracted with ethyl acetate (3×15 ml). The ethyl acetate extracts were combined, dried ($MgSO_4$), and evaporated to give an oil, which was purified by flash chromatography on silica gel using a 80:20:3 (v/v/v) mixture of ethyl acetate/ethanol/triethylamine as eluent to give 3-[2-(2-allyl-4-(3-hydroxybutyl)phenyl)ethynyl]quinuclidin-3-ol as a colourless oil (0.155 g), microanalysis found: C, 73.3; H, 8.7; N, 3.6; $C_{22}H_{29}NO_2.1.2M\ H_2O$ requires C, 73.2; H, 8.8; N, 3.9; m/z=340 (M+H).

EXAMPLE 103

Using a similar procedure to that described in Example 11 but using 3-(4-bromobenzyloxymethoxy)propane as starting material in place of 1-(4-bromo-2,6-dimethylphenoxy)-2-methoxyethane there was obtained 3-[2-(4-(3-methoxypropoxy)methyl)phenyl)ethynyl]quinuclidin-3-ol as a solid, m.p. 121–122° C.; NMR: 1.2–1.4(1H, m), 1.5–1.65(1H, m), 1.7–1.85(2H, q), 1.85–2.0(3H, m), 2.6–2.7 (4H, t), 2.8–2.9(1H, d), 3.0–3.1(1H, d), 3.2(3H, s), 3.35–3.45(2H, t), 3.45–3.55(2H, t), 4.45(2H, s), 5.5(1H, s) 7.25–7.35(2H, d) and 7.35–7.45(2H, d).

The starting material was prepared using an analogous procedure to that described in examples 11 for the preparation of 1-(4-bromobenzyloxy-2-methoxyethane but starting from 3-methoxypropanol. There was thus obtained 3-(4-bromobenzyloxymethoxy)propane; NMR ($CDCl_3$): 1.85–1.95(2H, q), 3.35(3H, s), 3.45–3.50(2H, t), 3.5–3.55 (2H, t), 4.5(2H, s), 7.2–7.3(2H, d) and 7.4–7.5(2H, d).

EXAMPLE 104

Using a similar procedure to that described in Example 11 but using 2-(4-bromobenzyloxy)-1-(isopropoxy)ethane as starting material in place of 1-(4-bromo-2,6-dimethylphenoxy)-2-methoxyethane there was obtained 3-[2-(4-(2-isopropoxyethoxy)methyl)phenyl)ethynyl] quinuclidin-3-ol as a solid, m.p. 117–118° C.; NMR: 1.05–1.1(6H, d), 1.2–1.4(1H, m), 1.5–1.7(1H, m), 1.8–2.0 (3H, m), 2.6–2.75(4H, t), 2.8–2.9(1H, d), 3.0(3.1(1H, d), 3.5–3.6(5H, m), 4.5(2H, s), 5.55(1H, s) and 7.25–7.4(4H, q).

The starting material was prepared using an analogous procedure to that described in Example 11 for the preparation of 1-(4-bromobenzyloxy)-2-methoxyethane but starting from isopropoxy ethanol. There was thus obtained 2-(4-bromobenzyloxy)-1-(isopropoxy)ethane; NMR ($CDCl_3$): 1.1–1.2(6H, d), 3.6(5H, m), 4.5(2H, s), 7.2–7.3(2H, d), and 7.4–7.5(2H, d).

EXAMPLE 105

Using a similar procedure to that described in Example 11 but using 3-(4-bromophenyl)-1-(methoxy)propane as starting material in place of 1-(4-bromo-2,6-dimethylphenoxy)-2-methoxyethane there was obtained 3-[2-(4-(3-methoxypropyl)phenyl)ethynyl]quinuclidin-3-ol as a solid, m.p. 145° C.; NMR: 1.2–1.4(1H, m), 1.5–1.7(1H, m), 1.7–2.0(5H, m), 2.55–2.75(6H, m), 2.75–2.9(1H, d), 3.0–3.15(1H, d), 3.2(3H, s), 3.25–3.4(2H, m), 5.5(1H, s), 7.1–7.2(2H, d) and 7.25–7.74(2H, d).

The starting material was prepared using an analogous procedure to that described in Example 35 for the preparation of 3-(4-allyloxyphenyl)-1-methoxypropane but starting from 3-(4-bromophenyl)propyl bromide. There was thus obtained 3-(4-bromophenyl)-1-(methoxy)propane; NMR ($CDCl_3$): 1.8–2.0(2H, m), 2.6–2.7(2H, t), 3.3–3.4(5H, m), 7.0–7.1(2H, d) and 7.3–7.4(2H, d).

EXAMPLE 106

Using a similar procedure to that described in Example 11 but using 3-(4-bromobenzyloxy)propane as starting material in place of 1-(4-bromo-2,6-dimethylphenoxy)-2-methoxyethane, there was obtained 3-[2-(4-propoxymethylphenyl)ethynyl]quinuclidin-3-ol as a solid, m.p. 140–141° C.; NMR (CDCl$_3$): 0.9–1.0(3H, t), 1.3–1.5 (1H, m), 1.55–1.7(3H, m), 1.9–2.1(3H, m), 2.7–2.95(5H, m), 3.0–3.1(1H, d), 3.25–3.35(1H, d), 3.4–3.5(2H, t), 4.5 (2H, s), 7.2–7.3(2H, d) and 7.35–7.43(2H, d).

The starting material was prepared using an analogous procedure to that described in Example 11 for the preparation of 1-(4-bromobenzyloxy)-2-methoxyethane but starting from n-propanol. There was thus obtained 3-(4-bromobenzyloxy)propane; NMR (CDCl$_3$): 0.9–1.0(3H, t), 1.6–1.7(2H, q), 3.4–3.5(2H, t), 4.5(2H, s), 7.15–7.3(2H, d) and 7.4–7.5(2H, d).

EXAMPLE 107

Using a similar procedure to that described in Example 11 but with 1-(4-bromo-2-fluorobenzyloxy)-2-methoxyethane in place of 1-(4-bromobenzyloxy)-2-methoxyethane there was obtained 3-[2-(4-(2-methoxyethoxymethyl]-2-fluorophenyl)ethynyl]quinuclidin-3-ol (13% yield) as a solid, m.p. 117–118° C.; microanalysis, found: C, 68.4; H, 7.5; N, 4.3%; C$_{19}$H$_{24}$FNO$_3$ requires: C, 68.4; H, 7.3; N, 4.2%; NMR: 1.30(1H, m), 1.61(1H, m), 1.95(3H, m), 2.69 (4H, t), 2.83(1H, d), 3.07(1H, d), 3.25(3H, s), 3.49(2H, m), 3.56(2H, m), 4.52(2H, s), 5.66(1H, s), 7.22(2H, m) and 7.39(1H, t); m/Z 333 (M+H).

The 1-(4-bromo-2-fluorobenzyloxy)-2-methoxyethane used as starting material was obtained as follows.

2-Methoxyethanol (5.0 g) was added to a stirred suspension of sodium hydride (2.64 g of a 60% mineral oil suspension) in DHF (200 ml) at room temperature and under a atmosphere of argon. The stirred mixture was heated to 60° C. and then cooled to 5° C. A solution of 4-bromo-2-fluorobenzyl bromide (15 g) in dichlorobenzene (75 ml) was added over 15 minutes. The mixture stirred for 12 hours at room temperature, then for 1 hour at 60° C. and cooled. The mixture was diluted with iced water (600 ml) and extracted with ethyl acetate (3×200 ml). The combined extracts were washed with 2M hydrochloric acid (100 ml), water (2×100 ml), saturated brine (100 ml) and dried (MgSO$_4$). Evaporation of the solvents gave an oil which was distilled using a short path distillation apparatus to give 1-(4-bromo-2-fluorobenzyloxy)-2-methyoxyethane (11.6 g), furnace temperature 125° C./0.01 bar; NMR (CDCl$_3$): 3.40(3H, s), 3.5–3.7(4H, m), 4.58(2H, s) and 7.2–7.4(3H, m).

EXAMPLE 108

Sodium borohydride (1.14 g) was added portionwise over a period of 10 minutes to a solution of 3-[-2-(2-formyl-4-ethoxycarbonylethylphenyl)ethynyl]quinuclidin-3-ol (2 g) and saturated aqueous sodium bicarbonate (2 ml) in methanol (10 ml) at 10° C. under an atmosphere of argon. The reaction mixture was stirred at ambient temperature 2 hours. An equal volume of water was added and the mixture was extracted with ethyl acetate. The ethyl acetate extract was dried (MgSO$_4$), evaporated and the residue was purified by chromatography on silica gel (Varian Bond Elut S1 silica gel) using a gradient of 0 to 20% ethyl acetate in hexane to give 3-[2-{2-hydroxymethyl-4-ethoxycarbonylethylphenyl}-ethynyl]quinuclidin-3-ol borane complex (480 mg) as a solid; NMR: 2.65(2H, t), 2.95(6H, m), 3.2(1H, d), 3.3(1H, s), 3.4(1H, d), 3.65(1H, s), 4.73(2H, s), 7.1(1H, m), 7.28(1H, s), 7.35(1H, d); m/Z 358 (M+H).

EXAMPLE 109

Using the method described in Example 70, but with 4-(2-iodophenoxy)-2-methylbut-2-ene (855 mg) in place of 2-iodophenylacetonitrile and (+) 3-ethynyl-3-hydroxyquinuclidine in place of 3-ethynyl-3-hydroxyquinuclidine there was thus obtained 3-[2-{2-(3-methylbutox-2-ene)phenyl}ethynyl]quinuclidin-3-ol (427 mg) as a solid, m.p 175.1° C., microanalysis, found: C, 76.4; H, 8.3; N, 4.7%; C$_{20}$H$_{25}$NO$_2$ 0.15H$_2$O requires: C, 76.5; H, 8.12; N, 4.46%; NMR 1.31(1H, m), 1.55(1H, m), 1.74(6H, d), 1.81–2.14(3H, m), 2.67(4H, t), 2.81(1H, d), 3.08(1H, d), 4.57(2H, d), 5.37–5.55(2H, m), 6.9(1H, t), 7.03(1H, d) and 7.29(2H, m); m/Z 312 (M+H).

EXAMPLE 110

Using the method described in Example 1, but carrying out the reaction at ambient temperature overnight and with 2,2-dichloroethyl-2-iodobenzoate [generated in situ by the reaction of 2-iodobenzoyl chloride (718 mg) with 2,2-dichloroethanol (0.34 ml) in triethylamine (1 ml) as solvent at ambient temperature] in place of ethyl 3-(3-allyl-4-trifluoromethylsulphonyloxyphenyl)propionate there was thus obtained 3-[2-{2-(2',2'-dichloroethoxycarbonyl) phenyl}ethynyl]quinuclidin-3-ol as a solid (396 mg), m.p. 160.7° C.; microanalysis, found: C, 57.9: H, 5.3; N, 4.1%; C$_{18}$H$_{19}$Cl$_2$NO$_3$ 0.25H$_2$O requires C, 58.0; H, 5.27; N, 3.76%; NMR: 1.31(1H, m), 1.6(1H, m), 1.98(3H, m), 2.6–3.05(6H, m), 4.72(2H, d), 5.58(1H, s), 6.6(1H, t), 7.45–7.68(3H, m), 7.92(1H, d); m/Z 368° C.

EXAMPLE 111

Using the method described in Example 1, but carrying out the reaction at ambient temperature overnight and with 2-chloroethanol-2-iodobenzate [generated in situ by the reaction of 2-iodobenzoyl chloride (718 mg) with 2-chloroethanol (0.34 ml) in triethylamine (1 ml) as solvent at ambient temperature)] in place of ethyl 3-(3-allyl-4-trifluoromethylsulphonyloxyphenyl)propionate there was thus obtained 3-[2-{2-(2-chloroethoxycarbonyl) phenyl}ethynyl]quinuclidin-3-ol as a solid (286 mg), m.p. 132.2° C.; microanalysis, found C, 63.8; H, 6.1; N, 4.5%; C$_{18}$H$_{20}$ClNO$_3$, 0.25H$_2$O requires C, 63.9; H, 6.11; N, 4.14%; NMR: 1.32(1H, m), 1.57(1H, m), 1.94(3H, m), 2.7(4H, m), 3.05–3.4(2H, m), 3.95(2H, m), 4.51(2H, m), 5.56(1H, s), 7.44–7.65(3H, m), 7.88(1H, d); m/Z 334 (M+H).

EXAMPLE 112

Using the method described in Example 1, but carrying out the reaction at ambient temperature overnight and with phenyl-2-iodobenzoate, [generated in situ by the reaction of 2-iodo benzoyl chloride (678 mg) with phenol (279 mg) in triethylamine (1 ml) as solvent at ambient temperature)] in place of ethyl 3-(3-allyl-4-trifluoromethylsulphonoxyphenyl)propionate there was thus obtained 3-[2-{2-(phenoxycarbonyl)phenyl}ethynyl] quinuclidin-3-ol as a solid (472.5 mg), m.p. 60.3° C., microanalysis, found: C, 71.4; H, 5.8; N, 3.9; I, 2.8%; C$_{22}$H$_{21}$NO$_3$0.75H$_2$O.0.07 HI requires C, 71.4; H, 61.5; N, 3.79; I, 2.4%; NMR: 1.3(1H, m), 1.5(1H, m), 1.9(3H, m), 2.67(4H, t), 2.95(1H, +H$_2$O), 3.14(1H, d), 5.15(1H, s), 7.25–7.7(8H, m), 8.03(1H, d); m/Z 348 (M+H).

EXAMPLE 113

Using the method described in Example 1, but carrying out the reaction at ambient temperature overnight and with 2,2,2-trichloroethyl-2-iodobenzoate [generated in situe by the reaction of 2-iodo benzoyl chloride (718 mg) with 2,2,2-trichloroethanol (0.34 ml) in triethylamine (1 ml) as solvent at ambient temperature] in place of ethyl 3-(3-allyl-4-trifluoromethylsulphonyloxyphenyl)propionate there was thus obtained 3-[2-{2-(2,2,2trichloroethoxycarbonyl) phenyl}ethynyl]quinuclidin-3-ol as a solid (533 mg), m.p. 127.4° C.; microanalysis, found C, 53.4; H, 4.6; N, 3.4%; $C_{18}H_{18}Cl_3NO_3$ requires C, 53.7; H, 4.51; N, 3.48%; NMR: 1.3(1H, m), 1.53(1H, m), 1.95(3H, m), 2.68(4H, t), 2.82(1H, d), 3.13(1H, d), 5.14(2H, s), 5.57(1H, s), 7.5–7.7(3H, m), 7.98(1H, d); m/Z 404 (M+H).

EXAMPLE 114

A mixture of 3-{2-(2-hydroxymethyl-4-ethoxycarbonylethylphenyl}ethynyl]quinuclidin-3-ol borane complex (400 mg), triphenylphosphine (524 mg) and toluene (50 ml) was stirred at 0° C. under an atmosphere of argon. A solution of diethylazodicarboxylate (340 mg) in toluene (10 ml) was added over a period of 5 minutes and the reaction mixture stirred at ambient temperature overnight. Water (50 ml) was added and the mixture extracted with ethyl acetate. The ethyl acetate extracts were dried ($MgSO_4$) and evaporated. The residue was purified by chromatography on silica gel (Varian Band Elut S1 silca gel) using a gradient of 0 to 20% ethyl acetate in hexane to give the product as a borane complex. Treatment at 10° C. with hydrochloric acid dissolved in a mixture of acetone and ethanol gave, upon evaporation, 3-[2-{2-phenoxymethyl-4-ethoxycarbonylethylphenyl}ethynyl]quinuclidin-3-ol as a gum; NMR ($CDCl_3$): 1.24(3H, t), 2.6(2H, t), 2.96(2H, t), 4.1(2H, q), 5.08( H, s), 6.9–7.05(4H, m), 7.15–7.45(5H, m); m/Z 434 (M+H).

EXAMPLE 115

In a similar manner to that described in Example 1 but using 3-ethynyl-3-hydroxyquinuclidine and methyl 6-(3-allyl-4-trifluoromethylsulphonyloxyphenyl)caproate as starting materials, there was thus obtained 3-[2-(2-allyl-4-(5-methoxycarbonylpentyl) phenyl)ethynyl]quinuclidin-3-ol as a gum (87 mg), NMR: 1.25–1.5(1H,m), 1.5–1.9(1H+ $H_2O$,m), 1.9–2.1(1H,m), 2.2–2.3(2H,t), 2.5–2.6(2H,m), 2.7–3.0(4H,m), 3.0–3.1(1H,d), 3.3–3.4(1H,dd), 3.45–3.55 (2H,d), 3.65(3H,s), 5.0–5.1(2H,m), 5.9–6.1(1H,m), 6.95–7.0(2H,m) and 7.3–7.35(1H,d), m/z 396(M+H).

The methyl 6-(3-allyl-4-trifluoromethylsulphonyloxyphenyl)caproate used as starting material was prepared in a similar manner to ethyl 3-(3-allyl-4-trifluoromethylsulphonyloxyphenyl)propionate (described in Example 1).

EXAMPLE 116

In a similar manner to that described in Example 1 but using 3-allyl-4-trifluoromethylsulphonyloxyphenylpropionate as starting material there was thus obtained 3-[2-allyl-3(4-propionitrile)ethynyl]quinuclidin-3-ol as a solid (478 mg), m.p. 124.3° C.; NMR ($CDCl_3$): 1.3–1.45(1H,m), 1.5–1.65 (1H,m), 1.8–2.1(3H,m), 2.5–2.6(2H,t), 2.7–2.9(5H,m), 2.9–3.05(1H,d), 3.2–3.3(1H,dd), 3.4–3.5(2H,d), 4.95–5.1 (2H,m), 5.8–6.0(1H,m), 6.9–7.0, (2H,m), and 7.3–7.35(1H, d), m/z 321(M+H).

The 3-allyl-4-trifluoromethylsulphonyloxyphenylproprionitrile used as starting material was prepared in a similar manner to ethyl 3-(3-allyl-4-trifluoromethylsulphonyloxyphenyl)propionte described in Example 1.

EXAMPLE 117

A solution of 3-[2-{2-allyl-4-(2-ethoxycarbonylethyl) phenyl}ethynyl]quinuclidin-3-ol (1.0 g) in methanol saturated with ammonia was allowed to stand at ambient temperature for 48 hours. The solvent was evaporated to give an oil which, on trituration with diethyl ether, gave a solid. The solid was crystallised from ethyl acetate to give 3-[2-{2-allyl-4-(2-amidoethyl)phenyl}ethynyl]quinuclidin-3-ol as a solid (562 mg), m.p. 137.5° C.; microanalysis, found: C, 72.6; H, 7.70; N, 7.80%, $C_{21}H_{26}N_2O_2$. 0.5 $H_2O$ requires: C, 72.6; H, 7.77; N, 8.00%; NMR: 1.28–1.45(1H,m), 1.50–1.85 (1H,m), 1.85–2.12(3H,m), 2.30(2H,t), 2.75(10H,m), 5.05 (2H,m), 5.60(1H,bs), 5.88–6.05(1H,m), 6.70(1H,bs), 7.03 (2H,m) and 7.25(2H, d and bs), m/z 339(M+H).

EXAMPLE 118

The procedure described in Example 117 was repeated using methanolic methylamine in place of methanolic ammonia. There was thus obtained, after crystallisation from ethyl acetate, 3-[2-{2-allyl-4-(2-methylamidoethyl) phenyl}ethynyl]quinuclidin-3-ol as a solid, m.p. 115.2° C.; microanalysis, found: C, 72.1; H, 8.30; N, 7.80%, $C_{22}H_{28}N_2O$. 0.75$H_2O$ requires: C,72.2; H, 7.66; N, 7.66%; NMR([$CD_3$]$_2$SO/$CD_3$COOD): 1.62–1.82(1H,m), 1.92–2.10 (1H,m), 2.10–2.30(3H,m), 2.38(2H,t), 2.60(3H,s), 2.82(2H, t), 3.00–3.47(6H,m), 3.50(2H,d), 5.05(2H,m), 5.90–6.05 (1H,m), 7.05(2H,m) and 7.30(1H,d), m/z 353(M+H).

EXAMPLE 119

A solution of 3-[2-{2-allyl-4-(2-ethoxycarbonylethyl) phenyl}ethynyl]quinuclidin-3-ol (734 mg) in tetrahydrofuran (15 ml) was added over a period of 0.25 hours to a stirred suspension of lithium borohydride (450 mg) in tetrahydrofuran (15 ml) at 0° C. under an atmosphere of argon. The mixture was stirred for 16 hours at ambient temperature. The tetrahydrofuran was removed by evaporation. Acetone (20 ml) was added slowly with stirring followed by 1M aqueous hydrochloric acid (20 ml). The mixture was stirred for 1 hour at ambient temperature. The acetone was removed by evaporation and the aqueous mixture was basified to pH 12 using 2M aqueous sodium hydroxide solution and then extracted with ethyl acetate (2×50 ml). The ethyl acetate extracts were combined, washed with brine (2×30 ml), dried ($MgSO_4$) and evaporated. The residue was purified by flash column chromatography on Meutral Alumina (ICN Alumma N 32-63) using a 9:1 (v/v) mixture of ethyl acetate and methanol as eluent to give 3-[2-(2-allyl-4-(3-hydroxypropane)phenyl) ethynyl]quinuclidin-3-ol (123 mg) as a glass; NMR($CDCl_3$): 1.35–1.52(1H,m), 1.58–1.73(1H,m), 1.87(2H,m), 1.92–2.22 (3H,m), 2.68(2H,t), 2.77–2.98(4H,m), 3.08(1H,d), 3.32(1H, d.d), 3.50(2H,d), 3.63(2H,t), 4.98–5.12(2H,m), 5.85–6.08 (1H,m), 7.01(2H,m) and 7.33(1H,d): m/z 326(M+H).

EXAMPLE 120

Using the method described in Example 67 but using 3-[2-(2-allyl-4-(2-methoxycarbonylpropyl)phenyl)ethynyl] quinuclidin-3-ol in place of 3-[2[2-allyl-4-(2-ethoxycarbonylethyl)phenyl]ethynyl]quinuclidin-3-ol, there was obtained 3-[2-[2-allyl-4-(2-carboxypropyl)phenyl]

ethynyl]quinuclidin-3-ol hydrochloride salt as a solid, m.p. 45–47° C. (dec), NMR([CD$_3$]$_2$SO/CD$_3$COOD): 1.10(3H,d), 1.75–1.90(1H,m), 1.95–2.10(1H,m), 2.13–2.41(3H,m), 2.62 (2H,m), 2.93(1H,q), 3.15–3.33(4H,m), 3.40(1H,d), 3.51(2H, d), 3.60(1H,d), 4.98–5.10(2H,m), 5.88–6.08(1H,m), 7.08 (2H,m) and 7.37(1H,d), m/z 354(M+H).

EXAMPLE 121

Cuprous Iodide (150 mg) and tris-(dibenzylidene acetone) dipalladium (100 mg) (100 mg) were added to a solution of 3-((E)-2-tributylstannyl-1-ethenyl)-3-hydroxyquinuclidine (882 mg), and N-(1-butyl)-4-iodophenylacetamide (951 mg) in DMF (10 ml) under an atmosphere of argon. The reaction mixture was stirred at ambient temperature for 15 minutes. The solvent was removed by evaporation, and the residue was purifed by chromatography on silica gel using 20% methanol in dichloromethane containing 1% ammonia as eluent to give 3-[(E)-2-[4-[N-(1-butyl)-carboxamidomethyl] phenyl]vinyl]quinuclidin-3-ol, as a solid which was recrystallised from ethyl acetate to give a solid (330 mg), mpt: 128–130° C.; microanalysis, found: C:71.6; H: 8.6; N:7.7%; C$_{21}$H$_{30}$N$_2$O$_2$+0.15 CH$_3$CO$_2$C$_2$H$_5$+0.10 H$_2$O requires: C: 72.0; H: 8.6; N:7.7%; 7.8%; NMR: 0.93–0.90, (3H,t), 1.15–1.55,(6H,m), 1.57–1.75(2H,m), 1.93–2.10(H.bm), 2.55–2.82(5H,m), 2.85–2.90(1H,dd), 3.00–3.08(2H,q), 3.35 (2H,s), 4.72(1H,s), 6.50–6.63(2H,AB), 7.18–7.38(4H,AB) and 7.90(H,bt); m/z343(M+H).

The N-(1-butyl)-4-iodophenylacetamide used as starting material was prepared as follows.

1-Butylamine (1.83 g) was added to a solution of 4-iodophenylacetyl chloride (2.80 g) in ether (25 ml), and the reaction mixture was stirred at ambient temperature for 5 minutes. The reaction mixture was then partitioned between water (30 ml) and ethyl acetate (50 ml). The organic layer was washed with 2M aqueous hydrochloric acid (25 ml), water (30 ml), brine (25 ml), dried (MgSO$_4$), and evaporated to give N-1-butyl, (4-iodophenyl)acetamide, as a colourless crystalline solid, (2.9 g), mp.: 100–102° C., NMR: 0.82–0.88(3H,t), 1.18–1.43(4H,m), 3.00–3.06(2H,q), 3.35(2H,s), 7.03–7.67(4H,AB), 7.97(H,bt); m/z 318 (M+H).

EXAMPLE 122

In a similar manner to Example 121, but using 4-iodophenylacetamide in place of N-(1-butyl)-4-iodophenylacetamide, there was obtained 3-[(E)-2-(4-carboxamidomethylphenyl)vinyl]quinuclidin-3-ol as a solid, m.p. 180–184° C., (after recrystallisation from a mixture of ethyl acetate/hexane), microanalysis, Found: C, 69.7; H: 8.1; N, 9.5%; C$_{17}$H$_{22}$N$_2$O$_2$ 0.5 H$_2$O requires: C, 69.3; H:7.8; N:9.5% m/z 287 (M+H); NMR: 1.17–1.53(2H, m), 1.60–1.75(2H,m), 1.92–2.08(H,m), 2.55–2.82(5H,m), 2.85–2.90(1H,d), 3.33(2H,s), 4.72(H,s), 6.50–6.63(2H,AB) and 6.82(H,b).

The 4-iodophenylacetamide used as starting material was obtained as follows.

Thionyl chloride (39.53) and DMF (2 drops) were added to a solution of 4-iodophenylacetic acid (26.2 g), in dichloromethane (150 ml). The reaction mixture was stirred at ambient temperature for 18 hours and the solvent removed by evaporation to give 4-iodophenylacetyl chloride as an oil (23 g) which was purified by vacuum distillation; b.p. 118–119° C. (0.35 mmMg)

Concentrated aqueous ammonia (density, 0.88 g/cm$^3$) was added to a solution of 4-iodophenylacetyl chloride (2.80 g) in ether (30 ml) and the mixture was stirred at ambient temperature for 15 minutes. The product, 4-iodophenylacetamide, was obtained as a colourless crystalline solid (2.36 g), m.p: 200–204° C.; NMR: 3.34(2H,s), 6.87(H,bs), 7.44(2H,bs), 7.04–7.68(4H,AB); m/z 262(M+H).

EXAMPLE 123

In a similar manner to Example 121, but using methyl (4-iodophenyl)acetate in place of N-(1-butyl)-4-iodophenylacetamide, there was obtained 3-[(E)-2-(4-methoxycarbonylmethylphenyl)vinyl]quinuclidin-3-ol as a solid (135 mg), mp 133–136° C. (after recrystallisation from ethyl acetate), NMR: 1.12–1.55(2H,m), 1.67(2H,m), 2.00 (H,bm), 2.58–2.90(6H,m), 3.30(2H,s), 3.60(H,s), 3.64(2H, s), 4.73(H,s), 6.57(2H,s), 7.17–7.40(4H,AB).

The methyl 4-iodophenylacetate used as starting material was prepared as follows.

4-iodophenylacetyl chloride (2.80 g) was added to methanol (10 ml) and the mixture stirred at ambient temperature for 15 minutes. The solvent was removed by evaporation to give methyl 4-iodophenylacetate as a red oil (2.73 g) which was used without further purification; NMR: 3.62(s,3H), 3.67(s,2H), 7.05–7.70(AB,4H). m/z277(M+H)

EXAMPLE 124

The procedure used in Example 93 was repeated using 3-[4-(3-hydroxypropyl)phenoxymethyl]quinuclidin-3-ol borane complex (0.24 g) instead of 3-(4-cyanomethylphenoxymethyl)quinuclidin-3-ol borane complex, except that the reaction mixture was diluted with an equal volume of diethyl ether and stirred for 16 hours to give 3-[4-(3-hydroxypropyl)phenoxymethyl]quinuclidin-3-ol hydrochloride (0.17 g) as a colourless solid, m.p. 143–146° C.; microanalysis, found: C, 62.4; H, 8.0; N, 4.4%; C$_{17}$H$_{25}$NO$_3$ HCl requires: C, 62.3; H, 8.0; N, 4.3%; NMR: 1.5–2.0(5H,m), 2.1–2.3(2H,m), 2.4–2.6(2H,t), 2.9–3.4(6H, m), 3.35–3.5(2H,t), 3.9–4.1(2H,s), 4.2–4.6(1H, br), 5.4–5.6(1H,s), 6.8–6.95(2H,d), 7.05–7.2(2H,d)and 10.4–10.8(1H,s); m/z 292 (M+H).

The 3-[4-(3-hydroxypropyl)phenoxymethyl]quinuclidin-3-ol borane complex used as starting material was prepared from 3-(4-hydroxyphenyl)-1-propanol using an analogous procedure to that described in Example 93 for the preparation of the borane starting material. Thus, the procedure described in Example 93 was repeated using 3-(4-hydroxyphenyl)-1-propanol (0.30 g) instead of 4-hydroxybenzyl cyanide. There was thus obtained 3-[4-(3-hydroxypropyl)phenoxymethyl]quinuclidin-3-ol borane complex (0.25 g) as a solid.

EXAMPLE 125

Using the method described in Example 1, but with methyl 3-(3-allyl-4-trifluromethylsulphonyloxyphenyl)-2,2-dimethylpropionate in place of ethyl 3-(3-allyl-4-trifluromethylsulphonyloxyphenyl) propionate, there was thus obtained 3-[2-(2-allyl-4-(2-methoxycarbonyl-2,2-dimethylethyl)phenyl)ethynyl]quinuclidin-3-ol as an oil; NMR (CDCl$_3$): 1.15(6H,s), 1.32–1.50(1H,m), 1.57–1.77 (1H,m), 1.90–2.10(3H,m), 2.30(1H,m), 2.70–3.00(6H,m), 3.05(1H,d), 3.31(1H,dd), 3.50(2H,d), 3.62(3H,s), 4.97–5.12 (2H,m), 5.88–6.03(1H,m), 6.90(2H,m) and 7.30(1H,d); m/z 482(M+H).

The methyl 3-(3-allyl-4-trifluoromethylsulphonyloxyphenyl)-2,2-dimethylpropionate used as starting material was obtained as follows.

Allyl bromide (0.66 ml) was added to a stirred suspension of methyl 2,2-dimethyl-3-(4-hydroxyphenyl)propionate (1.41 g) and potassium carbonate (1.08 g) in butan-2-one (12 ml). The reaction mixture was heated at reflux for 19 hours, cooled, and filtered. The filtrate was evaporated to give methyl 2,2-dimethyl-3-(4-allyloxyphenyl)propionate (1.59 g) as an oil; NMR(CDCl$_3$): 1.17(6H,s), 2.78(2H,s), 3.65(3H, s), 4.50(2H,m), 5.33(2H,m), 6.02(1H,m), 6.70(2H,m) and 7.00(2H,m); m/z 248(M+).

A solution of methyl 2,2-dimethyl-3-(4-allyloxyphenyl) propionate (1.56 g) in diphenyl ether was heated at reflux for 15 minutes. The reaction mixture was cooled to ambient temperature and the reaction mixture was filtered through a silica gel pad. Elution with a 4:1 (v/v) mixture of hexane and ethyl acetate gave methyl 2,2-dimethyl-3-(3-allyl-4-hydroxyphenyl)propionate (1.53 g) as a yellow oil; microanalysis, found: C, 72.2; H, 7.80%; $C_{15}H_{20}O_3$ requires: C, 72.6; H, 8.12%; NMR(CDCl$_3$): 1.15(6H,s), 2.73(2H,s), 3.35(2H,m), 3.63(3H,s), 4.87(1H,s), 5.10(2H, m), 5.95(1H,m), 6.67(1H,m) and 6.83(2H,m); m/z 249 (M+H).

Trifluoromethane sulphonic anhydride (1.25 ml) was added to a stirred solution of methyl 2,2-dimethyl-3-(3-allyl-4-hydroxyphenyl)propionate (1.51 g) in pyridine (6.0 ml) at 0° under an atmosphere of argon. After 16 hours 1M hydrochloric acid (100 ml) was added to the reaction mixture and the mixture was extracted with ether. The ether phase was washed with brine, dried and evaporated to give an oil. Purification of the oil by chromatography on silica gel using a 9:1 (v/v) mixture of hexane/ethyl acetate mixture as eluent give methyl 2,2-dimethyl-3-(3-allyl-4-trifluoromethylsulphonyloxy)phenyl)propionate (2.18 g) as an oil; NMR(CDCl$_3$) 1.18(6H,s), 2.82(2H,s), 3.42(2H,d), 3.63(3H,s), 5.10(2H,m), 5.92(1H,m), 7.02(2H,m) and 7.13 (1H,d).

EXAMPLE 126

Using the method described in Example 1, but with methoxyethyl 2-methyl-3-(3-allyl-4-trifluoromethylsulphonyloxyphenyl)propionate in place of ethyl 3-(3-allyl-4-trifluoromethylsulphonyloxyphenyl) propionate and (−)-3-ethynyl-3-hydroxy-quinuclidine in place of (±)-3-ethynyl-3-hydroxyquinuclidine there was thus obtained (−) 3-[2-(2-allyl-4-methoxyethoxycarbonyl-1-methylethylphenyl)ethynyl]quinculidin-3-ol (as a diastereoisomic pair) as a yellow oil; microanalysis, found: C, 71.0; H, 8.20; N, 3.10%; $C_{25}H_{33}NO_4$. 0.5 $H_2O$ requires C, 71.3; H, 8.10; N, 3.30%; NMR(CDCl$_3$) 1.13(3H,d), 1.41(1H,m), 1.64(1H,m), 2.06(3H,m), 2.75(8H,m), 3.30(4H,m), 3.52 (4H,m), 4.18(2H,m), 5.06(2H,m), 5.94(1H,m), 6.98(2H,m) and 7.31(1H,d); m/z 412(M+H).

The methoxyethyl 2-methyl-3-(3-allyl-4-trifluromethylsulphonyloxyphenyl)propionate used as starting material was prepared as follows.

Concentrated sulphuric acid (0.2 ml) was added to a stirred suspension of 4-oxypropionyl-2-methylcinnamic acid (2.78 g) in 2-methoxyethanol (20 ml) and the reaction mixture was heated at 100° C. for 16 hours. The 2-methoxyethanol was removed by evaporation and saturated sodium bicarbonate solution (20 ml) was added. The mixture was extracted with ether. The ether phase was dried (MgSO$_4$) and evaporated to give methoxyethyl 3-(4-hydroxyphenyl)-2-methyl cinnamate (2.60 g) as a colourless solid m.p.101.8° C.; NMR(CDCl$_3$): 2.12(3H,d), 3.44(3H,s), 3.72(2H,t), 4.38(2H,t), 5.82(1H,m), 6.82(2H,d), 7.28(2H,d) and 7.6(1H,s).

A solution of methoxyethyl 2-methyl 4-hydroxycinnamate (2.56 g) in ethyl acetate (75 ml) was hydrogenated at atmospheric pressure and ambient temperature over a 10% Pd-C catalyst (180 mg). The catalyst was removed by filtration and the filtrate was evaporated to give methoxyethyl 2-methyl-3-(4-hydroxyphenyl)propionate (2.56 g) as an oil; NMR(CDCl$_3$): 1.17(3H,d), 2.70(2H,m), 2.92(1H,q), 3.36(3H,s), 3.55(2H,m), 4.21(2H,m), 5.16(1H, bs), 6.72(2H,m) and 7.01(2H,m).

Methoxyethyl 2-methyl-3-(4-allyloxyphenyl)propionate was prepared using the procedure used to prepare ethyl 3-(4-allyloxyphenyl)propionate (see Example 1). Methoxyethyl 2-methyl-3-(3-allyl-4-hydroxyphenyl)propionate was prepared from methoxyethyl 2-methyl-3-(4-allyloxyphenyl) propionate using the method described in Example 1 for the preparation of ethyl 3-(3-allyl-4-hydroxyphenyl)propionate. The product was isolated as a yellow oil; microanalysis; found: C, 69.0 H, 7.70%; $C_{16}H_{22}O_4$ requires C, 69.0 H. 7.97%; m/z 279 (M+H).

The method described in Example 1 for the preparation of ethyl 3-(3-allyl-4-trifluoromethylsulphonyloxyphenyl) propionate was used to convert methoxyethyl 2-methyl-3-(3-allyl-4-hydroxyphenyl)propionate to methoxyethyl 2-methyl-3-(3-allyl-4-trifluoromethylsulphonyloxyphenyl) propionate; NMR(CDCl$_3$): 1.18(3H,d), 2.73(2H,m), 3.00 (1H,q), 3.36(3H,s), 3.42(2H,d), 3.51(2H,m), 4.18(2H,m), 5.09(2H,m), 5.90(1H,m) and 7.13(3H,m); m/z 411 (M+H).

EXAMPLE 127

Using the method described in Example 1 but using (+) 3-ethynyl-3-hydroxy quinuclidine in place of (±)$_3$-ethynyl-3-hydroxy quinuclidine and methoxyethyl 2-methyl-3-(3-allyl-4-trifluoromethyl sulphonyloxyphenyl)propionate in place of ethyl 3-(3-allyl-4-trifluoromethylsulphonyloxyphenyl)propionate there was thus obtained (as a diastereomeric pair) (+) 3-[2-(2-allyl-4-methoxy ethoxycarbonyl-1-methylethylphenyl)ethynyl] quinuclidin-3-ol as an oil; NMR(CDCl$_3$): 1.16(3H,d), 1.44 (1H,m), 1.64(1H,m), 2.05(3H,m), 2.87(8H,m), 3.38(4H,m), 3.52(4H,m), 4.18(2H,m), 5.05(2H,m), 5.94(1H,m), 6.98 (2H,m) and 7.31(1H,d); m/z 412 (M+H).

EXAMPLE 128

Using the method described in Example 1 but using ethyl 3-(3-allyl-4-trifluoromethylsulphonyloxyphenyl)-1-methyl propionate in place of ethyl 3-(3-allyl-4-trifluoromethylsulphonyloxyphenyl)propionate, there was thus obtained 3-[2-(2-allyl-4-(2-ethoxycarbonyl-1-methylethyl)phenyl)ethynyl]quinuclidin-3-ol as a gum, NMR(CDCl$_3$): 1.18(3H,t), 1.30(2H,d), 1.45(1H,m), 1.65 (1H,m), 2.02(3H,m), 2.20(1H,m), 2.53(2H,m), 2.87(4H,m), 3.06(1H,d), 3.22(1H,m), 3.30(1H,d.d), 3.50(2H,d), 4.07(2H, q), 5.05(2H,m), 5.95(1H,m), 7.02(2H,m) and 7.33(1H,d); m/z 382(M+H).

The compound of formula 2 (Z=OSO$_2$CF$_3$) used as starting material was prepared as follows.

Triethyl phosphonacetate (5.0 g) was added to a stirred suspension of sodium hydride (0.95 g; 60% dispersion in oil) in THF (35 ml) at ambient temperature under an atmosphere of argon. After 1 hour, a solution of 4-benzyloxyacetophenone (5.0 g) in tetrahydrofuran (35 ml) was added. The reaction mixture was heated at reflux for 16 hours. The reaction mixture was cooled to ambient temperature and water (200 ml) was added. The aqueous mixture was extracted with ether. The ether phase was washed with water, brine, dried (MgSO$_4$) and evaporated. The residue was purified on silica gel using a 19:1 (v/v) mixture as eluent to give ethyl 3-methyl-3-(4-benzyloxy)phenyl cinnamate (3.44 g) as a colourless solid; NMR (CDCl$_3$): 1.31(3H,t), 2.52(3H,s), 4.20(2H,q), 5.08(2H,s), 5.95(1H,m), 6.93(2H, m) and 7.40(7H,m); m/z 297(M+H).

Ethyl 3-(4-benzyloxyphenyl)but-2-enoate (3.4 g) in ethyl acetate (100 ml) was hydrogenated over a 10% palladium-on-carbon catalyst (250 mg) at atmospheric pressure/ambient temperature. The catalyst was removed by filtration and the filtrate evaporated to give an oil. The oil was purified by chromatography on silica gel using a 4/1 (v/v) mixture of hexane and ethyl acetate as eluent to give ethyl 3-(4-hydroxyphenyl)butanoate (1.51 g) as a pale yellow oil; NMR(CDCl$_3$): 1.20(3H,t), 1.27(3H,d), 2.52(2H,q), 3.22(1H, m), 4.08(2H,q), 4.84(1H,s), 6.71(2H,m) and 7.08(2H,m); m/z 208(M). Ethyl 3-(4-allyloxyphenyl)butanoate was prepared using the procedue used to prepare ethyl 3-(4-allyloxyphenyl)propionate (see Example 1) but using ethyl 3-(4-hydroxyphenyl)butanoate in place of ethyl 3-(4-hydroxyphenyl)propionate; NMR(CDCl$_3$) 1.17(3H,t), 1.25 (3H,d), 2.51(2H,m), 3.22(1H,m), 4.05(2H,q), 4.50(2H,m), 5.33(2H,m), 6.06(1H,m), 6.82(2H,m) and 7.11(2H,m); m/z 249 (M+H).

Ethyl 3-(3-allyl-4-hydroxyphenyl)butanoate was prepared as for ethyl 3-(3-allyl-4-hydroxyphenyl)propionate as in Example 1 but using ethyl 3-(4-allyloxyphenyl)butanoate in place of ethyl 3-(4-allyloxyphenyl)propionate; microanalysis: found: C, 72.6; H, 7.80%; C$_{15}$H$_{20}$O$_3$ requires C, 72.6; H, 8.12%; m/z 249(M+H).

The compound of formula 2 (Z=O.SO$_2$CF$_3$) was prepared as for ethyl 3-(3-allyl-4-trifluorosulphonyloxyphenyl) propionate in Example 1 using ethyl 3-(3-allyl-4-hydroxyphenyl)butanoate in place of ethyl 3-(3-allyl-4-hydroxyphenyl)propionate. There was thus obtained an oil; NMR(CDCl$_3$): 1.17(3H,t), 1.41(3H,d), 2.55(2H,m), 3.30 (1H,m), 3.46(2H,d), 4.08(2H,q), 5.12(2H,m), 5.90(1H,m) and 7.13(3H,m).

EXAMPLE 129

In a similar manner to that described in Example 97, but using isobutyryl chloride in place of pivaloyl chloride, there was obtained 3-[2-(4-dimethylacetyloxymethyl-2-allylphenyl)ethynyl]quinuclidin-3-ol as a solid, m.p. 68° C.; microanalysis, found: C, 75.5; H, 8.0; N, 4.0%; C$_{23}$H$_{29}$NO$_3$ requires: C, 75.2; H, 8.0; N, 3.8%; NMR (CDCl$_3$): 1.2 (6H, d), 1.4 (1H, m), 1.65 (1H, m), 2.1 (3H, m), 2.6 (1H, m), 2.8 (4H, t), 3.1 (1H, d), 3.3 (1H, dd), 3.5 (2H, d), 5.1 (4H, m), 5.9 (1H, m), 7.1 (2H, m) and 7.4 (11H, d), m/z 368 (M+H).

EXAMPLE 130

In a similar manner to that described in Example 97, but using ethyl malonyl chloride in place of pivaloyl chloride, there was obtained 3-[2-(4-carbethoxyacetyloxymethyl-2-allylphenyl)ethynyl]quinuclidin-3-ol as an oil, NMR (CDCl$_3$): 1.2 (3H, t), 1.4 (1H, m), 1.65 (1H, m), 2.1 (3H, m), 2.8 (4H, m), 3.1 (1H, d), 3.3 (1H, dd), 3.4 (2H, s), 3.5 (2H, s), 3.5 (2H, d), 4.2 (2H, q), 5.1 (4H, m), 5.9 (1H, m), 7.1 (2H, m) and 7.4 (1H, d), m/z 412 (M+H).

EXAMPLE 131

Sodium borohydride (33 mg) was added to a solution of 3-[2-(4-(2-dicarbethoxyethylenyl)-2-allylphenyl)ethynyl] quinuclidin-3-ol (306 mg) in ethanol (7 ml) whilst maintaining the temperature at 5° C. The resulting mixture was stirred at 25° C. for 12 hours, filtered, and the ethanol was then evaporated. The residue was stirred with acetone (5 ml) and 1 h aqueous hydrochloric acid (2.75 ml) was then added. The resulting mixture was stirred at 25° C. for 3 hours and sodium hydrogen carbonate (250 mg) was then added. The mixture was extracted with ethyl acetate (3×15 ml). The ethyl acetate extracts were combined, washed with brine (15 ml), dried (Na$_2$SO$_4$) and evaporated to give a residue which was purified by medium pressure column chromatography on alumina (N32-63) using a 49:1 (v/v) mixture of ethyl acetate and methanol as eluent to give 3-[2-(4-(2-dicarbethoxyethyl)-2-allylphenyl)ethynyl]quinuclidin-3-ol as a solid, m.p. 89° C.; microanalysis, found: C, 70.8; H, 7.8; N, 3.1%; C$_{26}$H$_{33}$NO$_5$ requires: C, 71.0; H, 7.6; N, 3.2%; NMR (CDCl$_3$): 1.2 (6H, t), 1.4 (1H, m), 1.65 (1H, m), 2.1 (3H, m), 2.8 (4H, t), 3.0 (1H, d), 3.1 (2H, d), 3.3 (1H, dd), 3.4 (2H, d), 3.6 (1H, t), 4.1 (4H, q), 5.1 (2H, m), 5.9 (1H, m), 7.0 (2H, m) and 7.2 (1H, d). m/z 440 (M+H).

EXAMPLE 132

Butyl Lithium in hexane (1.6M, 3.4 ml) was added slowly to a stirred solution of trimethylsilylacetylene (1.0 g) in tetrahydrofuran (20 ml) at −70° C. under an atmosphere of argon. The reaction mixture was stirred at −70° C. for a further 60 minutes. A solution of 3-[2-(2-formylphenyl) ethynyl]-3-trimethylsilyloxyquinuclidine (1.3 g) in tetrahydrofuran (10 ml) was added slowly to the reaction mixture whilst maintaining the temperature at −70° C. The reaction mixture was allowed to warm to ambient temperature and then stirred for 20 hours. The reaction mixture was evaporated, potassium carbonate (4 g) and methanol (50 ml) added and the mixture was stirred vigorously at ambient temperature for 60 minutes. The inorganic salts were removed by filtration and the filtrate was evaporated to give a residue which was dissolved in ethyl acetate (150 ml). The solution was extracted with 2M hydrochloric acid (2×100 ml). The aqueous extracts were combined, washed with ether (2×200 ml) and then basified to pH 9 by addition of 5N sodium hydroxide solution. The aqueous mixture was extracted with ethyl acetate (2×100 ml), the ethyl acetate extracts combined, washed with water (100 ml), brine (100 ml), dried (MgSO$_4$) and evaporated. The residue was purified by column chromatography on alumina (Alumina N 32-63) using a gradient of 2:98 to 5:95 (v/v) methanol in ethyl acetate as eluent to give a solid which was recrystallised from a mixture of tetrahydrofuran/hexane to give 3-[2-{2-(1-hydroxy-1-ethynylmethyl)phenyl}ethynyl] quinuclidin-3-ol (110 mg), m.p. 217° C.; microanalysis; found: C, 74.6; H, 7.2; N, 4.6%, C$_{18}$H$_{19}$NO$_2$.0.5 H$_2$O requires: C, 74.5; H, 6.9; N, 4.8%; NMR: 1.2–1.4 (1H, m), 1.45–1.7 (1H, m), 1.8–2.05 (3H, m), 2.55–2.8 (4H, m), 2.85 (1H, d), 3.15 (1H, d), 3.38 (1H, dd), 5.58 (1H, s), 5.6–5.7 (1H, m), 6.08 (1H, d), 7.25–7.46 (3H, m), 7.65 (1H, d), m/z 282 (M+H).

The 3-[2-{2-formylphenyl}ethynyl]-3-trimethylsilyloxy quinuclidine used as starting material was obtained as follows.

Bis(triphenylphosphine)-palladium(II) chloride (175 mg) and copper(I) iodide (85 mg) were added to a solution of 2-bromobenzaldehyde (2.03 g) and 3-ethynyl-3-trimethylsilyloxyquinuclidine (2.23 g) in dimethyl formamide (25 ml) and triethylamine (5 ml) at ambient temperature under an atmosphere of argon. The reaction mixture was stirred at ambient temperature for 21 hours. The reaction mixture was poured into water (150 ml) and extracted with ethyl acetate (2×100 ml). The ethyl acetate extracts were combined, filtered, washed with water (2×100 ml), brine (100 ml), dried (MgSO$_4$) and evaporated. The residue was purified by column chromatography on alumina (Alumina N 32-63) using a 40:60 (v/v) mixture of ethyl acetate and isohexane as eluent to give 3-[2-{2-formylphenyl}ethynyl]-3-trimethylsilyloxyquinuclidine as an oil (2.1 g), NMR: 0.00 (9H, s), 1.1–1.3 (1H, m), 1.35–1.54 (1H, m), 1.82–1.90 (1H, m), 2.5 (4H, t), 2.73 (1H, d), 3.07 (1H,d), 7.38–7.48 (2H, m), 7.5–7.6 (1H, m), 7.68–7.75 (1H, m), 10.2 (1H, s), m/z 328 (M+H).

The 3-ethynyl-3-trimethylsilyloxyquinuclidine used as starting material was obtained as follows.

3-Ethynyl-3-hydroxyquinuclidine (1.5 g) and imidazole (1.7 g) were stirred in dimethyl formamide (25 ml). Trimethylsilylchloride (1.35 g) was added slowly to the solution and the mixture was stirred at ambient temperature for 20 hours. The reaction mixture was poured into water (150 ml) and the aqueous phase extracted with ethyl acetate (2×100 ml). The ethyl acetate extracts were combined, washed with water (2×100 ml), brine (100 ml), dried (MgSO$_4$) and evaporated to give 3-ethynyl-3-trimethylsilyloxyquinuclidine as an oil (1.8 g), NMR: 0.15 (9H, s), 1.2–1.38 (1H, m), 1.42–1.6 (1H, m), 1.65–1.9 (3H, m), 2.55–2.7 (4H, m), 2.76 (1H, d), 3.02 (1H, d), 3.55 (1H, s), m/z 224 (M+H).

A solution of 3-[2-{formylphenyl}ethynyl]-3-trimethylsilyloxyquinuclidine (0.815 g) in tetrahydrofuran (5 ml) was added slowly to a stirred solution of vinyl magnesium bromide (1.0M in tetrahydrofuran; 5 ml) in tetrahydrofuran (50 ml) at ambient temperature. The reaction mixture was stirred and heated at reflux for 3 hours. The reaction mixture was evaporated and the residue dissolved in 2M hydrochloric acid (50 ml). The aqueous phase was washed with ether (2×100 ml) and then basified to pH 9 by cautious addition of solid potassium carbonate. The mixture was extracted with ethyl acetate (2×100 ml). The ethyl acetate extracts were combined, washed with water (100 ml), brine (100 ml), dried (MgSO$_4$) and evaporated. The residue was purified by column chromatography on alumina (Alumina N 32-63) using a 5:95 (v/v) mixture of methanol in ethyl acetate as eluent to give a solid which was recrystallised from acetonitrile to give 3-[2-{-(1-hydroxy-1-ethenylmethyl)phenyl}ethynyl-3-hydroxy quinuclidine (117 mg), m.p. 148–149.5° C.; microanalysis, found: C, 75.9; H, 7.5; N, 4.9%; C$_{18}$H$_{21}$NO$_2$ requires: C, 76.3; H, 7.5; N, 4.9%; NMR: 1.2–1.4 (1H, m), 1.42–1.68 (1H, m), 1.7–2.0 (3H, m), 2.62 (4H, t), 2.85 (1H, d), 3.07 (1H, d), 4.95–5.07 (1H, m), 5.16–5.3 (1H, m), 5.45–5.56 (2H, m), 5.58 (1H, s), 5.86–6.08 (1H, m), 7.17–7.27 (1H, m), 7.3–7.4 (2H, m), 7.46–7.52 (1H, m), m/z 284 (M+H).

EXAMPLE 133

The β-ketoester prepared in Example 51 (0.22 g) was converted to its hydrochloride salt by dissolving in ethanol, and acidifying the resulting solution by adding ethanolic hydrogen chloride until the solution was pH 1. The solvent was removed immediately and the residue was dissolved in anhydrous dimethylformamide (5 ml) whilst under an atmosphere of argon. Sodium borohydride (0.044 g) was added to the mixture and the mixture was stirred for 1 day. An excess of sodium borohydride was added to the reaction mixture followed by anhydrous ethanol (5 ml). The reaction mixture was stirred overnight.

The reaction mixture was cooled with an ice-bath and quenched by careful addition of saturated ammonium chloride solution, whilst under an atmosphere of argon. The aqueous mixture was extracted with ethyl acetate (3×50 ml). The ethyl acetate extracts were combined, washed with brine (50 ml), dried (MgSO$_4$) and evaporated to give a colourless oil (0.2 g); m/z 354 (M–H). This oil was dissolved in acetone (5 ml) and treated with ethanolic HCl, until the pH>1. The mixture was stirred for a few hours at room temperature. The solvent was removed by evaporation and the residue was partitioned between saturated sodium carbonate solution (20 ml) and ethyl acetate (20 ml). The aqueous layer was further extracted with ethyl acetate (2×20cm$^3$). The ethyl acetate extracts were combined, washed with brine, dried (MgSO$_4$) and evaporated to produce a crude oil. The oil was purified by chromatography on silica gel (Varian Bond Elut S1 silica gel) using a 80:20:3 (v/v/v) mixture of ethyl acetate/ethanol/triethylamine as eluent to give 3-[2-(2-allyl-4-(1,2-dihydroxyethyl)phenyl)ethynyl]quinuclidin-3-ol as a gum (0.05 g); m/z 342(M+H).

EXAMPLE 134

The procedure described in Example 97 was repeated using benzyl alchol (0.4 g) and ethyl chloroformate as starting materials to give 3-[2-(2-allyl-4-ethoxycarbonyloxymethylphenyl)ethynyl (0.04 g); m/z370 (M+H).

EXAMPLE 135

A solution of hydrogen chloride dissolved in ethanol was added to a solution of 3-[2-(2-allyl-4-(ethoxycarbonylethylcarbonyl)phenyl)ethynyl]quinuclidin-3-ol (0.36 g) in ethanol (5 ml) to give a pH of 1. The mixture was evaporated and the residue was dissolved in ethanol (5 ml). Sodium borohydride (0.3 g) was added over a period of 4 hours. The reaction mixture was stirred overnight. The mixture was acidified with 2M aqueous hydrochloric acid. The mixture was filtered and the filtrate was evaporated. The residue was treated with acetone/ethereal hydrogen chloride mixture and then evaporated.

The residue was purified by chromatography on silica gel (Varian Bond Elut S1 silica gel) using an 80:20:3 mixture of ethyl acetate/ethanol/triethylamine as eluent to give 3-[2-(2-allyl-4-(1,4-dihydroxybutyl)phenyl)ethynyl]quinuclidin-3-ol (24 mg) as a gum; m/z 355(M+H).

EXAMPLE 136

The procedure described in Example 1 was repeated using 1-(methoxymethyl)-2-(trifluoromethylsulphonyloxy) benzene in place of ethyl 3-(3-allyl-4-trifluoromethylsulphonyloxyphenyl)propionate. There was thus obtained 3-[2-(2-methoxymethyphenyl)ethynyl] quinuclidin-3-ol as an oil; NMR(CDCl$_3$): 1.2–1.4(1H,m), 1.5–1.7(1H,m), 1.8–2.02(3H,m), 2.6–2.8(4H,m), 2.82–2.92 (1H,d), 3.05–3.15(1H,d), 3.4(3H,s), 4.62(2H,s) and 7.4(4H, m).

EXAMPLE 137

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |

| (b) Tablet II | mg/tablet |
|---|---|
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| (c) Tablet III | mg/tablet |
|---|---|
| compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| (d) Capsule | mg/capsule |
|---|---|
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compostions (a)–(c) may be enteric coated by conventional means, for example, with cellulose acetate phthalate

SCHEME 1

(a)

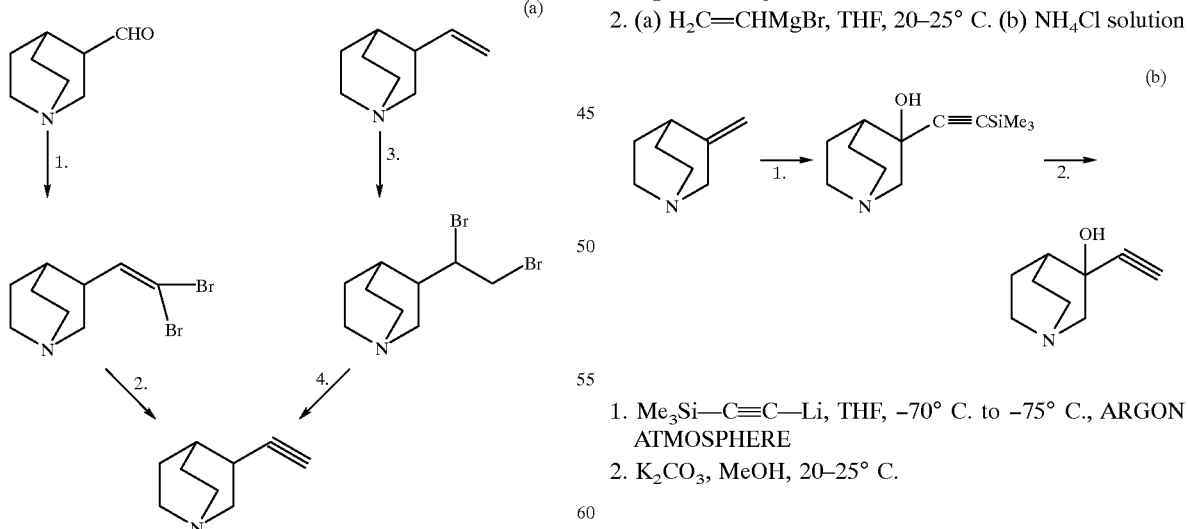

1. CBr$_4$/PPh$_3$/Zn, CH$_2$Cl$_2$, ROOM TEMPERATURE
2. (a) n.BuLi (2 equiv), THF, −60° C., ARGON ATMOSPHERE (b) H$_2$O
3. Br$_2$/H$_2$O
4. t. BuOK, t-BuOH, REFLUX (b)

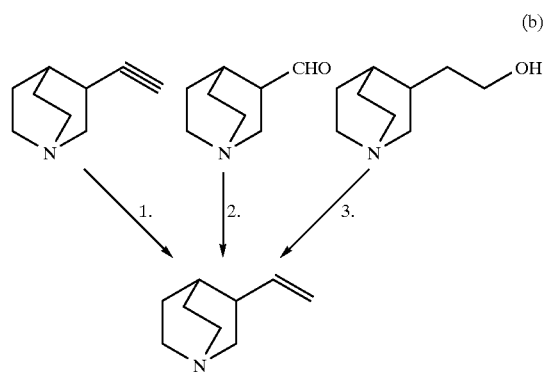

1. H$_2$/Pd. —C≡CO$_3$, EtOH
2. Ph$_3$$^+$PCH$_3$Br$^-$, KOBu$^t$, THF
3. PHTHALIC ANHYDRIDE, BENZENE SULPHONIC ACID. 280° C.

SCHEME 2

(a)

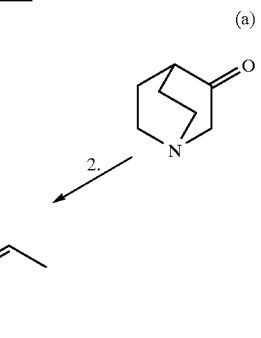

1. H$_2$/Pd-CaCO$_3$, ETOH
2. (a) H$_2$C=CHMgBr, THF, 20–25° C. (b) NH$_4$Cl solution (b)

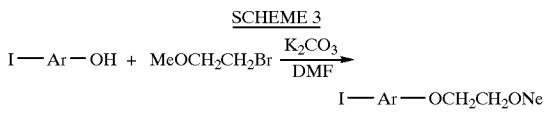

1. Me$_3$Si—C≡C—Li, THF, −70° C. to −75° C., ARGON ATMOSPHERE
2. K$_2$CO$_3$, MeOH, 20–25° C.

SCHEME 3

I—Ar—OH + MeOCH$_2$CH$_2$Br $\xrightarrow{\text{K}_2\text{CO}_3}{\text{DMF}}$ I—Ar—OCH$_2$CH$_2$ONe Br—Ar—OH +

-continued

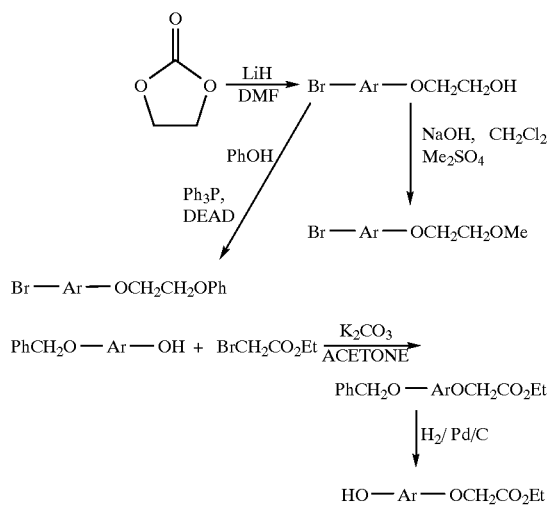

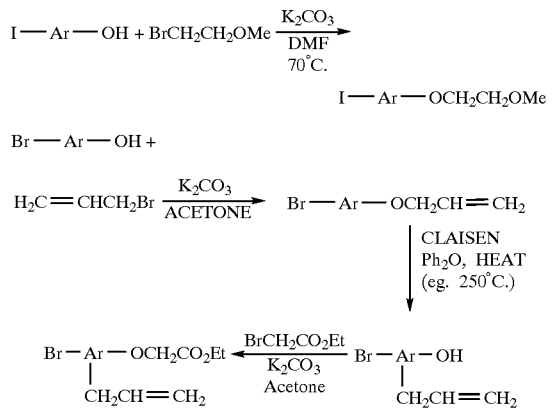

SCHEME 4

Ar(CH$_2$)mCHO + H$_2$C(CO$_2$H)$_2$ $\xrightarrow{1.}{2.}$ Ar(CH$_2$)mCH$_2$CO$_2$H 1. base, eg. NaOH or pyrollidine
2. H$_2$, Pd/C Ar(CH$_2$)mCOR$^{11}$ $\xrightarrow{1.}$ Ar(CH$_2$)mC(R$^{11}$) = CHCO$_2$R$^1$ $\xrightarrow{2.}$ Ar(CH$_2$)$_m$CH(R$^{11}$)CH$_2$CO$_2$R$^1$ 1. Ph$_3$P$^+$CH$_2$ = CO$_2$R$^1$Br$^-$, KOBu$^t$/THF
2. H$_2$, Pd/C

CHEMICAL FORMULAE

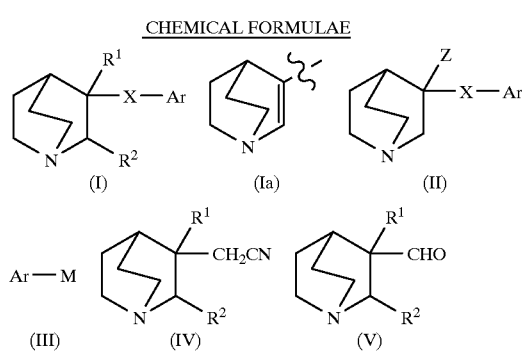

-continued

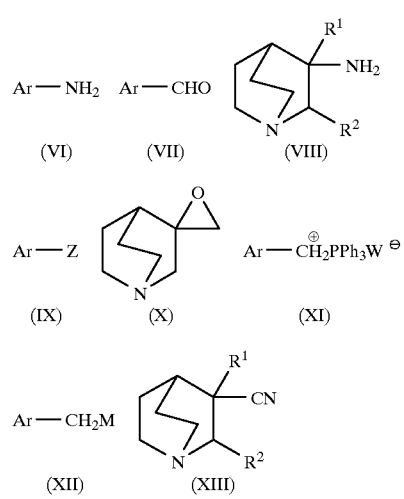

CHEMICAL FORMULAE

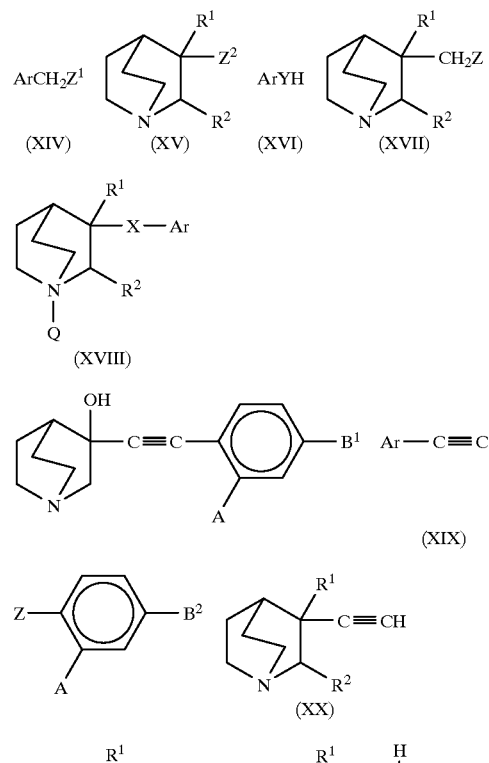

We claim:

1. A compound of formula I, or a pharmaceutically acceptable salt thereof,

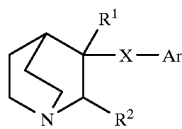

(I)

wherein:
$R^1$ is hydrogen or hydroxy;
$R^2$ is hydrogen; or
$R^1$ and $R^2$ are joined together so that $CR^1$–$CR^2$ is a double bond;
X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —CH$_2$S(O)$_n$— and —S(O)$_n$—CH$_2$— (wherein n is 0,1 or 2);
Ar is phenyl which bears one or more substituents independently selected from the groups (1-6C)alkyl, (2-6C)alkenyl, (2-6C)alkynyl, (1-6C)alkoxy, (1-6C)alkoxycarbonyl, (1-6C)alkoxycarbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkanoyl, (1-6C)alkanoyl oxime, O-(1-6C)alkyl ethers of a (1-6C)alkanoyl oxime, (1-6C)alkylthio, (1-6C)alkylsulphinyl and (1-6C)alkylsulphonyl, which substituent is itself substituted by one or more groups selected from (1-6C)alkoxycarbonyl, (1-6C)alkanoyl, (1-6C)alkanoyl oxime, O-(1-6C)alkyl ethers of a (1-6C)alkanoyl oxime, (1-6C)alkanoylamino, (1-6C)alkanoyloxy, (1-6C)alkanoyloxy(1-6C)alkyl, carbomoyl, N-(1-6C)alkylcarboamoyl, N,N-di[(1-6C)alkylcarbamoyl, amino, (1-6C)alkylamino, di-[(1-6C)alkyl]amino, (1-6C)alkoxy, (2-6C)alkenyloxy, (1-6C)alkylthio, (1-6C)alkylsulphinyl, (1-6C)alkylsulphonyl, halogeno (1-6C)alkyl, (2-6C)alkenyl, (2-6C)alkynyl, cyano, nitro and carboxy; and wherein Ar may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl] amino N-(1-6C)alkylcarboamoyl, di-N,N-[(l1-6C)alkyl]carbamoyl, (1-6C)alkoxycarbonyl, (1-6C)alkylthio, (1-6C)alkylsulphinyl, (1-6C)alkylsulphonyl, halogeno(1-6C)alkyl, (1-6C)alkanoylamino, (1-4C)alkylenedioxy, (1-6C)alkanoyl, (1-6C)alkanoyl oxime, and O-(1-6C)alkyl ethers of a (1-6C)alkanoyl oxime, provided that when
X is —OCH$_2$—, —NHCH$_2$— or —S(O)$_n$CH$_2$— (wherein n is 0,1 or 2), then $R^1$ is not hydroxy.

2. A compound of formula I, or a pharmaceutically acceptable salt thereof,

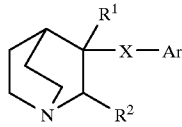

(I)

wherein:
$R^1$ is hydroxy;
$R^2$ is hydrogen;
X is selected from —CH$_2$CH$_2$—, —CH=CH—, —C≡C—, —CH$_2$O—, —CH$_2$NH—, —CH$_2$CO—, —COCH$_2$—, and —CH$_2$S(O)$_n$— (wherein n is 0,1 or 2);

Ar is phenyl which bears one or more substituents independently selected from the groups (1-6C)alkyl, (2-6C)alkenyl, (2-6C)alkynyl, (1-6C)akoxy, (1-6C)alkoxycarbonyl, (1-6C)alkoxyearbonyl(1-6C)alkyl, (1-6C)alkoxy(1-6C)alkyl, (1-6C)alkylamino, di-[(1-6C)alkyl]amino, carbamoyl, (1-6C)alkylcarbamoyl, di-[(1-6C)alkyl]carbamoyl, (1-6C)alkanoyl, (1-6C)alkanoyl oxime, O-(1-6C)alkyl ethers of a (1-6C)alkanoyl oxime, (1-6C)alkylthio, (1-6C)alkylsulphinyl and (1-6C)alkylsulphonly, which substituent is itself substituted by one or more groups seected from (1-6C)alkoxycarbonyl, (1-6C)alkanoyl, (1-6C)alkanoyl oxime, O-(1-6C)alkyl ethers of a (1-6C)alkanoyl oxime, (1-6C)alkanoylamino, (1-6C)alkanoyloxy, (1-6C)alkanoyloxy(1-6C)alkyl, carbamoyl, N-(1-6C)alkylcarbamoyl, N,N-di[(1-6C)alkylcarbamoyl, amino, (1-6C)alkylamino, di-[(1-6C)alkyl]amino, (1-6C)alkoxy, (2-6C)alkenyloxy, (1-6C)alkylthio, (1-6C)alkylsulphinyl, (1-6C)alkylsulphonyl, halogeno(1-6C)alkyl, (2-6C)alkenyl, (2-6C)alkynyl, cyano, nitro, hydroxy and carboxy; and wherein Ar may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl] amino N-(1-6C)alkylcarbomoyl, di-N,N-[(1-6C)alkyl]carbamoyl, (1-6C)alkoxycarbonyl, (1- 6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl, (1-6C)alkanoyl oxime, and O-(1-6C)alkyl ethers of a (1-6C)alkanoyl oxime.

3. A compound of formula I, or a pharmaceutically acceptable salt thereof,

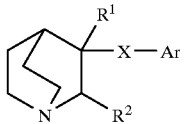

(I)

wherein;
$R^1$ is hydrogen or hydroxy;
$R^2$ is hydrogen; or
$R^1$ and $R^2$ are joined together so that $CR^1$–$CR^2$ is a double bond;
X is selected from —CH$_2$CH$_2$—, —CH=CH—, —C≡C—, —CH$_2$O—, —OCH$_2$—, —CH$_2$NH—, —NHCH$_2$—, —CH$_2$CO—, —COCH$_2$—, —CH$_2$S(O)$_n$— and —S(O)$_n$CH$_2$— (wherein n is 0,1 or 2);
Ar is phenyl which bears one or more substituents independently selected from the groups (1-6C)alkyl, (2-6C)alkenyl, (2-6C)alkynyl, (1-6C)alkoxy, (1-6C)alkoxy(1-6C)alkyl, (1-6C)alkylamino, di-[(1-6C)alkyl]amino, (1-6C)alkylthio, (1-6C)alkylsulphinyl and (1-6C)alkylsulphonyl, which substituent is itself substituted by one or sore groups selected from (1-6C)alkoxycarbonyl, (1-6C)alkanoyl, (1-6C)alkanoylamino, (1-6C)alkanoyloxy, N-(1-6C)alkylcarbamoyl, N,N-di[(1-6C)alkylcarbamoyl, (1-6C)alkoxy, (2-6C)alkenyloxy, (1-6C)alkylthio, (1-6C)alkylsulphinyl, (1-6C)alkylsulphonyl, halogeno(1-6C)alkyl, cyano and nitro; and wherein Ar may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbarmoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl, (1-6C)alkanoyl oxime, and O-(1-6C)alkyl ethers of a (1-6C)alkanoyl oxime; provided that when X is —OCH$_2$, —NHCH$_2$— or —S(O)$_n$CH$_2$— (wherein n is 0,1 or 2), then R$^1$ is not hydroxy.

4. A compound of formula I, or a pharmaceutically acceptable salt thereof,

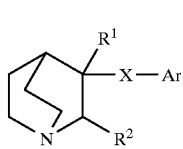

(I)

wherein:
R$^1$ is hydroxy;
R$^2$ is hydrogen;
X is selected from —CH$_2$CH$_2$—, —CH═CH—, —C≡C—, —CH$_2$O—, —CH$_2$NH—, —CH$_2$CO—, —COCH$_2$— and —CH$_2$S(O)$_n$— (wherein n is 0,1 or 2);
Ar is phenyl which bears one or more substituents independently selected from the groups (1-6C)alkyl, (2-6C)alkenyl, (2-6C)alkynyl, (1-6C)alkoxy, (1-6C)alkoxy(1-6C)alkyl, (1-6C)alkylamino, di-[(1-6C)alkyl]amino, (1-6C)alkylthio, (1-6C)alkylsulphinyl and (1-6C)alkylsulphonyl, which substituent is itself substituted by one or more groups selected from (1-6C)alkoxycarbonyl, (1-6C)alkanoyl, (1-6C)alkanoylamnino, (1-6C)alkanoyloxy, N-(1-6C)alkylcarbamoyl, N,N-di[(1-6C)alkylcarbamoyl, (1-6C)alkoxy, (2-6C)alkenyloxy, (1-6C)alkylthio, (1-6C)alkylsulphinyl, (1-6C)alkylsulphonyl, halogeno(1-6C)alkyl, cyano, nitro, and hydroxy;
and wherein Ar may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl, (1-6C)alkanoyl oxime, and O-(1-6C)alkyl ethers of a (1-6C)alkanoyl oxime.

5. A compound as claimed in claim 1 wherein Ar is phenyl which bears one or more substituents selected from (1-6C)alkoxycarbonyl(1-6C)alkyl, (1-6C)alkoxy(1-6C)alkoxy, (1-6C)alkoxy(1-6C)alkoxy(1-6C)alkyl, (1-6C)alkylthio(1-6C)alkoxy, (1-6C)alkoxy(1-6C)alkyl, (1-6C)alkoxy(1 6C)alkoxycarbonyl(1-6C)alkyl, (1-6C)alkoxycarbonyl(1-6C)alkoxy, (1-6C)alkanoyl(1-6C)alkyl, (1-6C)alkoxyoarbonyl(1-6C)alkanoyl and carboxy(1-6C)alkyl; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl, (1-6C)alkanoyl oxime, and O-(1-6C)alkyl ethers of a (1-6C)alkanoyl oxime.

6. A compound as claimed in claim 2 wherein Ar is phenyl which bears one or more substituents selected from (1-6C)alkoxycarbonyl(1-6C)alkyl, (1-6C)alkoxy(1-6C)alkoxy, (1-6C)alkoxy(1-6C)alkoxy(1-6C)alkyl, (1-6C)alkylthio(1-6C)alkoxy, (1-6C)alkoxy(1-6C)alkyl, (1-6C)alkoxy(1-6C)alkoxycarbonyl(1-6C)alkyl, (1-6C)alkoxycarbonyl(1-6C)alkoxy, hydroxy(1-6C)alkyl, (1-6C)alkanoyl(1-6C)alkyl, (1-6C)alkoxycarbonyl(1-6C)alkanoyl and carboxy(1-6C)alkyl; and optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino (1-4C)alkylenedioxy, (1-6C)alkanoyl, (1-6C)alkanoyl oxime, and O-(1-6C)alkyl ethers of a (1-6C)alkanoyl oxime.

7. A compound as claimed in claim 2 wherein R$^1$ is hydroxy, R$^2$ is hydrogen, X is selected from —CH$_2$CH$_2$—, —CH═CH—, —C≡C— and —CH$_2$O—; Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl, di-(1-6C)alkoxy, (1-6C)alkoxycarbonyl(2-6C)alkenyl, (1-6C)alkoxycarbonyl (1-6C)alkoxycarbonyl(1-6C)alkyl, (1-6C)alkoxy(1-6C)alkoxycarbonyl(1-6C)alkyl, (1-6C)alkoxy(1-6C)alkoxycarbonyl, (1-6C)alkylthio(1-6C)alkoxy, (1-6C)alkoxy(1-6C)alkyl, (1-6C)alkoxycarbonyl(1-6C)alkylcarbamoyl, (1-6C)alkoxy(1-6C)alkylcarbamoyl, (1-6C)alkanoyloxy(1-6C)alkyl, cyano(1-6C)alkoxy, carboxy(1-6C)alkyl, cyano(1-6C)alkyl, hydroxy(1-6C)alkyl, (1-6C)alkoxycarbonyl(1-6C)alkanoyl, (1-6C)alkylthio(1-6C)alkyl, (2-6C)alkenyl(1-6C)alkoxy(1-6C)alkyl, and (1-6C)alkanoyl(1-6C)alkyl, (1-6C)alkanoyl(1-6C)alkyl oxime and O-(1-6C)alkyl ethers of (1-6C)alkanoyl (1-6C)alkyl oxime; and wherein Ar may optionally bear one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno(1-6C)alkyl, (1-6C)alkanoylamino, (1-4C)alkylenedioxy, (1-6C)alkanoyl, (1-6C)alkanoyl oxime and O-(1-6C)alkyl ethers of (1-6C)alkanoyl oxime.

8. A compound as claimed in claim 2 wherein R$^1$ is hydroxy, R$^2$ is hydrogen, X is —C≡C—, Ar is phenyl which bears a substituent selected from methoxyethoxycarbonylethyl, methoxypropyl, ethoxycarbonylethyl, methoxycarbonylethyl, methoxycarbonylpropyl, methoxycarbonylbutyl, iso-butoxycarbonylethyl, hexyloxycarbonylethyl, methoxycarbonylpropyl, methoxycarbonylpentyl, methoxycarbonylmethoxy, methoxyethoxy, methoxyethoxymethyl, methoxyethoxyethyl, carboxyethyl, carboxypropyl, hydroxymethyl, ethanoylethyl, ethoxycarbonylethanoyl, ethoxycarbonylpropanoyl; and optionally one or more substituents selected from (1-6C)alkyl, (2-6C)alkenyl, halogeno, (1-6C)alkoxy and (1-6C)alkanoyl.

9. A compound as claimed in claim 1 wherein Ar is phenyl which bears a substituent selected from (1-6C)

alkoxycarbonyl(1-6C)alkyl and carboxy(1-6C)alkyl, and which optionally bears one or more substituents selected from the optional substituents defined in claim 1.

10. A compound as claimed in claim 9 wherein $R^1$ is hydroxy, $R^2$ is hydrogen, X is —C≡C—, Ar is phenyl which bears a substituent selected from (1-6C) alkoxycarbonyl(1-6C)alkyl and carboxy(1-6C)alkyl, and optionally bears a (2-6C)alkenyl group.

11. A compound as claimed in claim 2 wherein $R^1$ is hydroxy, $R^2$ is hydrogen, X is selected from —CH$_2$CH$_2$—, —CH═CH—, —C≡C— and —CH$_2$O—; Ar is phenyl which bears one or more substituents independently selected from (1-6C)alkoxycarbonyl(1-6C)alkyl, (1-6C)alkoxycarbonyl(1-6C)alkoxy, (1-6C)alkoxy(1-6C)alkoxy, (1-6C)alkoxy(1-6C)alkoxy(1-6C)alkyl and (1-6C)alkoxy(1-6C)alkoxycarbonyl; and Ar optionally bears one or more further substituents selected from halogeno, hydroxy, amino, nitro, cyano, carboxy, carbamoyl, (1-6C)alkyl, (2-6C)alkenyl, (2-6C)alkynyl, (1-6C)alkoxy, (1-6C)alkylamino, di-[(1-6C)alkyl]amino N-(1-6C)alkylcarbamoyl, di-N,N-[(1-6C)alkyl]carbamoyl, (1-6C)alkoxycarbonyl, (1-6C)alkylthio, (1-6C)alkylsulphinyl, (1-6C)alkylsulphonyl, halogeno (1-6C)alkyl, (1-6C)alkanoylamino, (1-4C)alkylenedioxy, (1-6C)alkanoyl, (1-6C)alkanoyl oxime and O-(1-6C)alkyl ethers of (1-6C)alkanoyl oxime.

12. A compound as claimed in any one of claims 1 or 2 wherein X is selected from —C≡C—, —CH$_2$CH$_2$—, —CH$_2$O— and —CH═CH—.

13. A compound as claimed in claim 2 wherein X is —C≡C—.

14. A compound selected from:
3-[2-(2-allyl-4-(2-ethoxycarbonylethyl)phenyl)ethynyl] quinuclidin-3-ol;
3-[2-(2-allyl-4-(2-methoxycarbonylethyl)phenyl)ethynyl] quinuclidin-3-ol;
3-[2-(2-allyl-4-(3-methoxycarbonylpropyl)phenyl)ethynyl] quinuclidin-3-ol;
3-[2-(2-allyl-4-(4-methoxycarbonylbutyl)phenyl)ethynyl] quinuclidin-3-ol;
3-[2-(2-allyl-4-(2-iso-butoxycarbonylethyl)phenyl)ethynyl] quinuclidin-3-ol;
3-[2-(2-allyl-4-(2-(2-methoxyethoxycarbonyl)ethyl)phenyl) ethynyl]quinuclidin-3-ol;
3-[2-(2-allyl-4-(3-methoxypropyl)phenyl)ethynyl] quinuclidin-3-ol;
3-[2-(2-allyl-4-(2-hexyloxycarbonylethyl) phenyl)ethynyl] quinuclidin-3-ol.
3-[2-(2-allyl-4-(2-methoxycarbonyl-2-methylethyl)phenyl) ethynyl]quinuclidin-3-ol;
3-[2-(2-allyl-4-(2-carboxyethyl)phenyl)ethynyl] quinuclidin-3-ol;
3-[2-(2-allyl-4-(5-methoxycarbonylpentyl)phenyl)ethynyl] quinuclidin-3-ol; and
3-[2-(2-allyl-4-(2-carboxypropyl)phenyl)ethynyl] quinuclidin-3-ol;
and pharmaceutically acceptable salts thereof.

15. A process for preparing a compound of formula I or a pharmaceutically acceptable salt thereof, as claimed in claim 1 or 2, wherein Ar, $R^1$ and $R^2$ are defined therein, which process comprises:

(a) for these compounds of formula I in which $R^1$ and $R^2$ are both hydrogen, reducing a compound of formula I in which $R^1$ and $R^2$ are joined together so that $CR^1$–$CR^2$ is a double bond;

(b) for compounds of formula I in which $R^1$ and $R^2$ are joined together so that $CR^1$–$CR^2$ is a double bond, dehydrating a compound of formula I in which $R^1$ is hydroxy and $R^2$ is hydrogen;

(c) for compounds of formula I in which $R^1$ and $R^2$ are joined together so that $CR^1$–$CR^2$ is a double bond, treating a compound of formula II

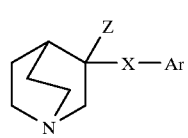
(II)

in which Z is a leaving group with a base;

(d) for those compounds of formula I in which X is —CH$_2$CO—, reacting an organometallic compound of formula III:

Ar—M (III)

in which M is a metal atom or a derivative thereof, with a compound of formula IV:

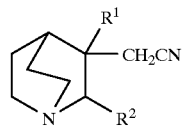
(IV)

e) for those compounds of formula I in which X is —CH$_2$—NH— or —NHCH$_2$—, reducing a compound of formula I in which X is —CH═N— or —N═CH—;

f) for those compounds of formula I in which X is —CH$_2$NH—, —CH$_2$O—, —CH$_2$S—, $R^1$ is hydroxy and $R^2$ is hydrogen, reacting a compound of formula IX:

Ar—Z (IM)

in which Z is —NH$_2$, —OH or SH with a compound of formula X:

(X)

g) for compounds of formula I in which X is —CH═CH—, reacting the reaction product of a compound of formula ArCH$_2$-halogen with triphenylphosphine with a compound of formula V:

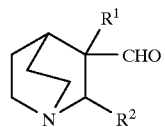
(XII)

in the presence of a base;

h) for those compounds of formula I in which X is —CH$_2$CH$_2$—, reducing a compound of formula I in which X is —CH═CH— or in which X is —C≡C—;

i) for compounds of formula I in which X is —COCH$_2$—, reacting a compound of formula XII:

 Ar—CH$_2$M (XII)

in which M is a metal atom or a derivative thereof, with a compound of formula XIII:

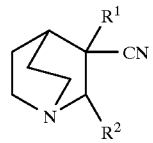 (XIII)

j) for those compounds of formula I in which X is —CH$_2$O— or —CH$_2$S—, reacting a compound of formula XIV

 ArCH$_2$Z$^1$ (XIV)

with a compound of formula XV

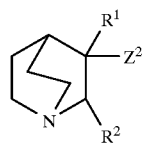 (XV)

in which Z$^1$ is a leaving group and Z$^2$ is —YM, or Z$^1$is —YM and Z$^2$ is a leaving group, and wherein Y is oxygen or sulphur and M is a metal atom;

k) for those compounds of formula I in which X is —OCH$_2$— or —SCH$_2$— and R$^1$ and R$^2$ are both hydrogen, reacting a compound of formula XVI:

 ArYH (XVI)

in which Y is oxygen or sulphur as appropriate with a compound of formula XVII

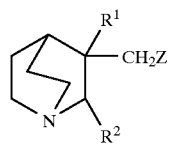 (XVII)

in which Z is a leaving group;

l) for compounds of formula I in which X is —OCH$_2$—, —SCH$_2$—, —CH2O—, or —CH$_2$S—, deprotecting a compound of formula XVIII

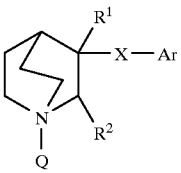 (XVIII)

in which Q is a protecting group;

m) for those compounds of formula I in which X is —C≡C—, reacting a compound of formula I in which X is —CH═CH— with a halogen, followed by treatment with a base;

n) for those compounds of formula I in which R$^1$ is hydroxy, R$^2$ is hydrogen and X is —C≡C—, reacting a compound of formula XIX:

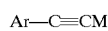 Ar—C≡CM (XIM)

in which M is a metal atom, with quinuclidin-3-one;

o) for those compounds in which R$^1$ and R$^2$ are hydrogen and X is —C≡C—, reacting a compound of formula XIX

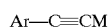 Ar—C≡CM (XIM)

in which M is a metal atom with a compound of formula XV

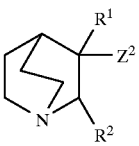 (XV)

in which Z is a leaving group;

p) for those compounds in which X is —C≡C— and R$^1$ is hydrogen or hydroxy and R$^2$ is hydrogen, reacting a compound of formula XX:

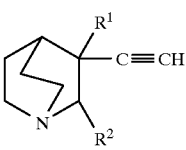 (XX)

with a compound of formula IX:

 Ar—Z (IX)

in which Z is a leaving group in the presence of a catalyst;

q) for those compounds in which X is —C═C— and R$^1$ is hydrogen or hydroxy and R$^2$ is hydrogen, reacting a compound of formula XXI:

(XXI)

with a compound of formula IX:

Ar—Z    (IX)

in which Z is a leacing group in the presence of a catalyst;
r) for those compounds in which X is —CH=CH—, reducing a compound of formula I in which X is —C≡C—;
s) for those compounds of formula I in which X is —CH=CH—, reacting a compound of formula XXII:

(XXII)

in which L is a (1-6)alkyl with a compound of formula IX:

Ar—Z    (IX)

in which Z is a leacing group in the presence of a catalyst;
and whereafter, when a pharmaceutically-acceptable salt is required, reacting the compound of formula I with an acid which affords a pysiologically acceptable anion or a base which affords a pysiologically acceptable cation.

16. A pharmaceutical composition which comprises a compound of formula I, or a pharmaceutically acceptable salt thereof, as claimed in claim 1 or 2 together with, or in admixture with, a pharmaceutically acceptable diluent or carrier.

17. A compound of formula I, or a pharmaceutically acceptable salt thereof, (I)

wherein:
$R^1$ is hydrogen or hydroxy;
$R^2$ is hydrogen; or
$R^1$ and $R^2$ are joined together so that $CR^1$–$CR^2$ is a double bond;
X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —$CH_2S(O)_n$— and —$S(O)_nCH_2$— (wherein n is 0,1 or 2);
Ar is phenyl which bears one or more substituents independently selected from (1-6C)alkoxycarbonyl(1-6C) alkyl, (1-6C)alkoxycarbonyl(1-6C)alkoxy, (1-6C) alkoxy(1-6C)alkoxy, (1-6C)alkoxy(1-6C)alkoxy(1-6C) alkyl, di-[(1-6C)alkoxy(1-6C)alkyl] (1-6C)alkoxy, (1-6C)alkoxy(1-6C)alkoxycarbonyl, di-[(1-6C)alkoxy] (1-6C)alkyl, (1-6C)alkylamino(1-6C)alkyl, di-[(1-6C) alkyl]amino(1-6C)alkyl, (1-6C)alkylcarbonylamino(1-6C)alkyl, (3-6C)cycloalkyl(1-6C)alkoxy, (2-6C) alkenyloxy(1-6C)alkyl, carbamoyl(1-6C)alkyl, N-(1-6C)alkylcarbamoyl(1-6C)alkyl, N,N-di-[(1-6C)alkyl] carbamoyl(1-6C)alkyl; (1-6C)alkoxycarbonyl(2-6C) alkenyl, (1-6C)alkoxycarbonyl(2-6C)alkynyl, cyano(1-6C)alkoxy, cyano(1-6C)alkoxy(1-6C)alkyl, nitro(1-6C)alkoxy, nitro(1-6C)alkoxy(1-6C)alkyl, (1-6C) alkoxycarbonyl(1-6C)alkylthio, (1-6C)alkoxycarbonyl (1-6C)alkoxycarbonyl(1-6C)alkyl, (1-6C)alkoxy(1-6C)alkoxycarbonyl(1-6C)alkyl, (1-6C)alkylthio(1-6C) alkoxy, (1-6C)alkoxy(1-6C)alkyl, (1-6C) alkoxycarbonyl(1-6C)alkylcarbamoyl, (1-6C)alkoxy (1-6C)-alkylcarbamoyl, (1-6C)alkanoyloxy(1-6C) alkyl, cyano(1-6C)alkyl, carboxy(1-6C)alkyl, hydroxy (1-6C)alkyl (1-6C)alkylamino(1-6C)alkyl, di-[(1-6C) alkyl]amino(1-6C)alkyl, (1-6C)alkylamino(1-6C) alkoxycarbonyl(1-6C)alkyl, di-[(1-6C)alkyl]amino(1-6C)alkoxycarbonyl(1-6C)alkyl, (1-6C)alkylcarbamoyl (1-6C)alkoxycarbonyl, di-[(1-6C)alkyl]carbamoyl(1-6C)alkoxycarbonyl, carbamoyl(1-6C)alkoxycarbonyl, (1-6C)alkoxycarbonyl(1-6C)alkoxy(1-6C)alkyl, di-[(1-6C)alkyl]amino(1-6C)alkoxycarbonyl, (1-6C) alkoxycarbonyl(1-6C)alkanoyl, (1-6C)alkoxy(1-6C) alkoxy(1-6C)alkanoyl, (1-6C)alkylthio(1-6C)alkyl, (2-6C)alkenyl(1-6C)alkoxy(1-6C)alkyl, (2-6C)alkynyl (1-6C)alkoxy(1-6C)alkyl, halogeno(1-6C)alkyl(1-6C) alkoxycarbonyl, di-[(1-6C)alkoxycarbonyl]alkyl, (1-6C)alkoxycarbonyl(1-6C)alkanoyloxy(1-6C)alkyl, (1-6C)alkoxy(1-6C)alkanoyloxy(1-6C)alkyl, (1-6C) alkoxy(1-6C)alkoxycarbonyl(1-6C)alkyl, hydroxy(1-6C)alkoxy, di-hydroxy(1-6C)alkyl, hydroxy(2-6C) alkenyl, hydroxy(2-6C)alkynyl, (1-6C)alkanoyl(1-6C) alkyl, (1-6C)alkanoyl (1-6C)alkyl oxime and O-(1-6C) alkyl ethers of (1-6C)alkanoyl(1-6C)alkyl oxime; and, in addition, optionally bears one or more substituents independently selected from halogeno, hydroxy, amino, nitro, cyano, carboxy, carbamoyl, (1-6C)alkyl, (2-6C)alkenyl, (2-6C)alkynyl, (1-6C)alkoxy, (1-6C) alkylamino, di-[(1-6C)alkyl]amino N-(1-6C) alkylcarbamoyl, di-N,N-[(1-6C)alkyl]carbamoyl, (1-6C)alkoxycarbonyl, (1-6C)alkylthio, (1-6C) alkylsulphinyl, (1-6C)alkylsulphonyl, halogeno (1-6C) alkyl, (1-6C)alkanoylamino, (1-4C)alkylenedioxy, (1-6C)alkanoyl (1-6C)alkanoyl oxime and O-(1-6C) alkyl ethers of (1-6C)alkanoyl oxime;
provided that when X is —$OCH_2$—, —$NHCH_2$— or —$S(O)_nCH_2$— (wherein n is 0,1 or 2), then $R^1$ is not hydroxy.

18. A compound as claimed in claim 3 or 4, respectively wherein Ar is phenyl which bears a substituent selected from (1-6C)alkoxycarbonyl(1-6C)alkyl and carboxy(1-6C)alkyl, and which optionally bears one or more substituents selected from the optional substituents defined in claim 3 or 4.

19. A compound as claimed in claim 17 wherein $R^1$ is hydroxy, $R^2$ is hydrogen, X is —C≡C—, Ar is phenyl which bears a substituent selected from (1-6C) alkoxycarbonyl(1-6C)alkyl and carboxy(1-6C)alkyl, and optionally bears a (2-6C)alkenyl group.

20. A pharmaceutical composition which comprises a compound of formula I, or a pharmaceutically acceptable salt thereof, as claimed in claim 3 or 4 together with, or in admixture with, a pharmaceutically acceptable diluent or carrier.

* * * * *